(12) United States Patent
Cheng

(10) Patent No.: US 7,732,166 B2
(45) Date of Patent: Jun. 8, 2010

(54) DETECTION METHOD FOR HUMAN PAPPILOMAVIRUS (HPV) AND ITS APPLICATION IN CERVICAL CANCER

(75) Inventor: Shu-Ling Cheng, Fremont, CA (US)

(73) Assignee: OncoHealth Corporation, Fremont, CA (US)

( * ) Notice: Subject to any disclaimer, the term of this patent is extended or adjusted under 35 U.S.C. 154(b) by 195 days.

(21) Appl. No.: 11/559,366

(22) Filed: Nov. 13, 2006

(65) Prior Publication Data

US 2008/0044809 A1 Feb. 21, 2008

Related U.S. Application Data

(60) Provisional application No. 60/737,152, filed on Nov. 15, 2005.

(51) Int. Cl.
C12P 21/06 (2006.01)
(52) U.S. Cl. .......................................... 435/69.1; 435/5
(58) Field of Classification Search ............... 435/6, 435/69.1
See application file for complete search history.

(56) References Cited

U.S. PATENT DOCUMENTS

| | | |
|---|---|---|
| 3,633,999 A | 1/1972 | Buckles |
| 4,511,220 A | 4/1985 | Scully |
| 4,619,508 A | 10/1986 | Shibuya et al. |
| 4,744,615 A | 5/1988 | Fan et al. |
| 4,851,978 A | 7/1989 | Ichihara |
| 5,061,025 A | 10/1991 | Debesis |
| 5,109,465 A | 4/1992 | Klopotek |
| 5,224,200 A | 6/1993 | Rasmussen et al. |
| 5,233,460 A | 8/1993 | Partlo et al. |
| 5,307,207 A | 4/1994 | Ichihara |
| 5,315,427 A | 5/1994 | Rauch et al. |
| 5,328,785 A | 7/1994 | Smith et al. |
| 5,357,365 A | 10/1994 | Ipposhi et al. |
| 5,401,627 A | 3/1995 | Dillner et al. |
| 5,415,995 A | 5/1995 | Schoolnik et al. |
| 5,453,814 A | 9/1995 | Aiyer |
| 5,561,081 A | 10/1996 | Takenouchi et al. |
| 5,610,733 A | 3/1997 | Feldman et al. |
| 5,621,529 A | 4/1997 | Gordon et al. |
| 5,629,161 A | 5/1997 | Muller et al. |
| 5,662,410 A | 9/1997 | Suganuma |
| 5,665,535 A * | 9/1997 | Orth et al. ............... 435/5 |
| 5,679,509 A | 10/1997 | Wheeler et al. |
| 5,699,191 A | 12/1997 | Fork |
| 5,754,278 A | 5/1998 | Kurtz |
| 5,876,723 A | 3/1999 | Cole et al. |
| 5,888,888 A | 3/1999 | Talwar et al. |
| 5,914,389 A | 6/1999 | Huibregtse et al. |
| 6,013,262 A | 1/2000 | Frazer et al. |
| 6,228,578 B1 | 5/2001 | Impraim et al. |
| 6,355,424 B1 | 3/2002 | Lorinez et al. |
| 6,420,106 B1 | 7/2002 | Gyllensten et al. |
| 6,524,825 B1 | 2/2003 | Mizzen et al. |
| 6,743,593 B2 | 6/2004 | Hu |
| 6,827,933 B2 | 12/2004 | Orth et al. |
| 6,884,786 B1 | 4/2005 | Kieny et al. |
| 6,890,514 B2 | 5/2005 | Mathur et al. |
| 6,900,035 B2 | 5/2005 | Mizzen et al. |
| 6,933,123 B2 | 8/2005 | Hu et al. |
| 2005/0037017 A1 | 2/2005 | Mizzen et al. |
| 2005/0037342 A1 | 2/2005 | Mathur et al. |
| 2005/0142541 A1 | 6/2005 | Lu et al. |
| 2005/0147621 A1 | 7/2005 | Higgins et al. |
| 2005/0255460 A1 | 11/2005 | Lu et al. |
| 2005/0255468 A1 | 11/2005 | Ridder et al. |
| 2005/0260566 A1 | 11/2005 | Fischer et al. |
| 2006/0029943 A1 | 2/2006 | Hermonat et al. |
| 2006/0039919 A1 | 2/2006 | Chang et al. |
| 2006/0121516 A1 | 6/2006 | Norman et al. |
| 2006/0153864 A1 | 7/2006 | Gissmann et al. |
| 2006/0172285 A1 | 8/2006 | Patterson |

OTHER PUBLICATIONS

Christensen et al, Virology, 1996, vol. 223, pp. 174-184.*
Nomine et al, Protein Engineering, 2001, vol. 14, No. 4, pp. 297-305.*
Bjorndal et al, Protein Expression and Purification, 203, vol. 31, pp. 47-55.*
Miraka et al, Protein Expression and Purification, 2006, vol. 48, 281-291.*
Bosch, et al 1995. Prevalence of human papillomavirus in cervical cancer: a worldwide perspective. J Natl Cancer Inst 87:796-802.
Doeberitz, Magnus Von Knebel "New Molecular tools for efficient screening of cervical cancer", Disease Markers 17 (2001) 123-128.

(Continued)

*Primary Examiner*—Ali R. Salimi
(74) *Attorney, Agent, or Firm*—Fenwick & West LLP

(57) ABSTRACT

Embodiments of the invention provide methods, assays, and kits for detecting HPV infection and HPV associated epithelial cell abnormalities, most notably those associated with pre-malignant and malignant epithelial cell lesions. Detection of HPV DNAs, genomes, and/or oncoproteins by nucleic acid hybridization assays and immunological assays can be used in early clinical screening for HPV infection and diagnosis for cervical cancer. The polypeptides, recombinant proteins, antibodies, nucleic acids, and various detection methods thereof are particularly useful for diagnosing carcinomas of the uterine cervix and those at risk of developing cervical cancer.

6 Claims, 18 Drawing Sheets

OTHER PUBLICATIONS

Fisher, et al. "The Association of Human Papillomavirus Type 16 E6 and E7 Antibodies with stage of Cervical Cancer", Gynecologic Oncology 61, 73-78 (1996) Article No. 0099.

Guimaraes, et al. 2005. "Immunohistochemical expression of p16INK4a and bcl-2 according to HPV type and to the progression of cervical squamous intraepithelial lesions". J Histochem Cytochem. 53: 509-16).

Hagensee, et al. "Detection of Cervical Antibodies to Human Papillomavirus Type 16 (HPV-16) Capsid Antigens in Relation to Detection of HPV-16 DNA and Cervcal Lesions", The Jourrnal of Infectious Diseases 2000; 181:1234-9.

Kiviat, et al. 1993. Specific human papillomavirus types as the causal agents of most cervical intraepithelial neoplasia: implications for current views and treatment. J Natl Cancer Inst 85: 934-35.

Koutsky, et al. 1992. A cohort study of the risk of cervical intraepithelial neoplasia grade 2 or 3 in relation to papillomavirus infection. N. Engl J Med 327:1272-1278. Abstract Only.

Kuroda, et al. 2005. The human papillomavirus E6 and E7 inducible oncogene, hWAPL, exhibits potential as a therapeutic target. Br J Cancer 92:290-3.

Li, et al. 2005. Regulation of apoptosis by papillomavirus E6 oncogene. World J Gastroenterol 11:931-37.

Longworth, et al., 2004. Pathogenesis of human papillomavirus in differentiating epithelia. Microbiol Mol Biol Rev 68: 362-72.

Madrigal, et al. 1997. In vitro antigene therapy targeting HPV-16 E6 and E7 in cervical carcinoma. Gynecol Oncol 64: 18-25.

Meschede, et al. "Antibodies agains Early Proteins of Human Papillomaviruses as Diagnostic Markers for Invasive Cervical Cancer" Journal of Clinical Microbiology Feb 1998, pp. 475-480.

Munoz, et al. 2003. Epidemiologic classification of human papillomavirus types associated with cervical cancer. N. Engl J Med 348:518-27.

Park, et al. 1995. Molecular biology of cervical cancer and its precursors. Cancer 76: 1902-13.

Park, et al. "HPV-16-Related Proteins as the Serolgic Markers in Cervical Neoplasia", Gynecologic Oncology 69, 47-55 (1998).

Parkin, et al. 1993. Estimates of the worldwide incidence of eighteen major cancers in 1985. Int J Cancer 54:594-606.

Sehr, et al. "A generic capture ELISA for recombinant proteins fused to glutathione S-transferase: validation for HPV serology" Journal of Immunological Methods 253 (2001) 153-162.

Solomon, et al. 2002. The 2001 Bethesda Systems. Terminology for reporting results of cervical cytology. JAMA 287:2114-19.

Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.

Sun, et al., "Comparison of Peptide Enzyme-Linked Immunosorbent Assay and Radioimmunoprecipitation Assay with in Vitro-Translated Proteins for Detection of Serum Antibodies to Human Papillomavirus Type 16 E6 and #7 Proteins" Journal of Clinical Microbiology Sep. 1994 pp. 2216-2230.

Tjiong, et al. "Antibodies agains Human Papillomavirus Type 16 and 18 E6 and E7 Proteins in Cervicovaginal Washings and Serum of Patients with Cervical Neoplasia" Viral Imjmunolgy vol. 14, No. 4, 2001 pp. 415-424.

Veress, et al. "Human Papillomavirus DNA and Anti-HPV Secretory IgA Antibodies in Cytologically Normal Cervical Specimens" Journal of Medical Virology 43:201-207 (1994).

Viscidi, et al. 1993. Serologic response in human papillomavirus-associated invasive cervical cancer. Int. J. Cancer 55:780-784.

Walboomers, et al. "Human Papillomavirus is a Necessary Cause of Invasive Cervical Cancer Worldwide", Jouranl of Pathology 189:12-19 (1999).

Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.

Zumbach, et al "Antibodies Against Oncoproteins E6 and E7 of Human Papillomavirus Types 16 and 18 in Cervical-Carcinoma Patents from Russia", Int. J. Cancer 85, 313-318 (2000) [Publication of the International Union Against Cancer].

International Search Report dated Jul. 18, 2007.

Berumen, et al. 2001 Asian-American Variants of Human Papillomavirus 16 and Risk for Cervical Cancer: a CaseControl Study Journal of the National Cancer Institute, vol. 93, No. 17.

Bleul, et al., "Human Papillomavirus Type 18 E6 and E7 Antibodies in Human Sera: Increased Anti-E7 Prevalence in Cervical Cancer Patients" Journal of Clinical Microbiology, Aug. 1991 pp. 1579-1588.

Bosch et al. 2002 The causal relation between human papillomavirus and cervical cancer. J. Clin. Pathol; 55; 244-265.

de Villiers 1997. Papillomavirus and HPV typing. Clin. Dermatol 15:199-206.

Hausen 2002. Papillomavirus and cancer: from basic studies to clinical application. Nat. rev. Cancer 2: 342-350.

Kreimer, et al. 2005. HPV 16 semiquantitative viral load and serological biomarkers in oral and oropharyngeal squamous cell carcinomas. Int J Cancer 115: 329-32.

Nair, Pillai 2005 Human papillomavirus and disease mechanisms: relevance to oral and cervical cancers Oral Diseases 11, 350-359.

Nindl, et al. 1994. Antibodies against linear and conformational epitopes of the human papillomavirus (HPV) type 16 E6 and E7 oncoproteins in sera of cervical cancer patients. Arch. Virol. 137:341-353.

Sasagawa, et al. 2003. Mucosal immunoglobulin-A and -G responses to oncogenic human papilloma virus capsids.Int J Cancer. Apr. 10, 2003; 104(d): 328-35.

Snijders, et al. 2006 HPV-mediated cervical carcinogenesis: concepts and clinical implications J Pathol 2006; 208: 152-164.

Stacey, et al. "Expression of human papillomavirus type 16 E6 protein by recombinant baculovirus and use for detection of anti-E6 antibodies in human sera", Jouranl of General Virology vol. 73, pp. 2337-2345.

Stoppler, et al. 1996 Natural Variants of the Human Papillomavirus Type 16 E6 Protein Differ in Their Abilities To Alter Keratinocyte Differentiation and To Induce p53 Degradation. Journal of Virology, p. 6987-6993 vol. 70, No. 10.

Tornesello, et al. 2004 Analysis of human papillomavirus type-16 variants in Italian women with cervical intraepithelial neoplasia and cervical cancer J Med Virol.; 74(1): 117-26.

Viscidi, et al. 1993. Serologic response in human papillomavirus-associated invasive cervical cancer. Int. J. Cancer 55:780-784.

Lehtinen, et al.2001. Human papillomavirus infection, risk for subsequent development of cervical neoplasia and associated population attributable fraction. J Clin Virolo 22:117-124.

Mougin, et al. 2001. Epidemiology of cervical papillomavirus infections. Recent knowledge. Press Med 30: 1017-23.

* cited by examiner

A). SDS-PAGE and B). western blot demonstrating the full length E6 recombinant protein stained with commassie blue, then probed with anti-E6 monclonal antibody, respectively.
Lane1:Protein marker (14.4,20.1, 31, 43, 66.2 , 96.7KD upward)
Lane2:HPV16E6 recombinant protein

| Subject# | Pap Smear | PCR | HPV-16 E6 Ab test | HPV-16 E7 Ab test |
|---|---|---|---|---|
| 12 | Abnormal | negative | positive | positive |
| 1 | Abnormal | negative | positive | positive |
| 20 | Abnormal | negative | positive | positive |
| 3 | Normal | positive | positive | positive |
| 57 | Normal | positive | | positive |
| 40 | Normal | positive | | positive |

Figure 14

| Subject# | Pap Smear | PCR test | HPV-16 E6 Ab test | HPV-16 E7 Ab test | HPV-16 E6 Ag test |
|---|---|---|---|---|---|
| 4 | *Abnormal* | *negative* | *positive* | *positive* | *positive* |
| 34 | Normal | positive | positive | positive | positive |
| 195 | Normal | negative | positive | positive | negative |
| 196 | Normal | positive | positive | positive | positive |
| 197 | Normal | negative | negative | negative | negative |
| 103 | Normal | negative | positive | positive | positive |
| 105 | Normal | negative | negative | negative | negative |
| 107 | Normal | negative | positive | positive | positive |
| 108 | Normal | negative | positive | positive | positive |
| 109 | Normal | negative | negative | negative | negative |
| 119 | Normal | negative | negative | negative | negative |

Figure 15

|  | Pap smear normal | | Total 173 subjects |
| --- | --- | --- | --- |
|  | E6 Ab Positive | E6 Ab Negative |  |
| L1 Ab Positive | 46 (PCR⁺, 26.6 %) + 7 (PCR⁻, 4 %)<br><br>53 subjects<br>(30.6 %) | 18 (PCR⁺, 10.4 %) + 13 (PCR⁻, 7.5 %)<br><br>31 subjects<br>(17.9 %) | 84 subjects<br><br>(48.6%) |
| L1 Ab Negative | 4 (PCR⁺, 2.4 %) + 8 (PCR⁻, 4.6 %)<br><br>12 subjects<br>(7.0 %) | 11 (PCR⁺, 6.3 %) + 66 (PCR⁻, 38.2 %)<br><br>77 subjects<br>(44.5 %) | 89 subjects<br><br>(51.4%) |
| Total | 50 (PCR⁺, 29 %) + 15 (PCR⁻, 8.6 %)<br><br>65 subjects<br>(37.6%) | 29 (PCR⁺, 16.7 %) + 79 (PCR⁻, 45.7 %)<br><br>108 subjects<br>(62.4%) | 173 subjects<br>(100%) |

Figure 16

| Sub. # | Pap score 1st and 2nd tests | Cytological Status | Histological or Biopsy follow up analysis | sample from pap test | PCR | HPV16 E6 Ab test | HPV16 E7 Ab test | HPV16 E6 Ag test |
|---|---|---|---|---|---|---|---|---|
| 15 | 4 (1st), 7 (2nd), 17 (3rd) | ASCUS (1st test), LSIL (2nd and 3rd time), possible HPV | Biopsy-HPV w/ atypical change and focal CIN 1 | 1st | Positive | Positive | | Positive |
| 8 | 4, 7 | ASCUS (1st), LSIL(2nd) | CIN 1, possible HPV | 2nd | Positive | Positive | | Positive |
| 7 | 4, 7 | ASCUS (1st), LSIL(2nd) | CIN 1, possible HPV | 2nd | Negative | Positive | | Negative |
| 13 | 4, 7 | ASCUS (1st), LSIL(2nd) | possible HPV infection | 1st | Negative | Positive | | Positive |
| 14 | 4 | ASCUS | | 1st | negative | Positive | | negative |
| 20 | 4 | ASCUS | | 1st | negative | negative | Positive | |
| 19 | 4 | ASCUS | | 1st | negative | negative | | Positive |
| 17 | 4 | ASCUS | | 1st | negative | Positive | | negative |
| 16 | 4 | ASCUS | | 1st | negative | negative | | negative |
| 18 | 4 | ASCUS | | 1st | negative | negative | | negative |
| 12 | 4, 5 | AGUS (1st), LSIL(2nd) | | 2nd | negative | Positive | Positive | negative |
| 11 | 5 | AGUS | | 1st | Positive | negative | | negative |
| 10 | 7 | LSIL, possible HPV | CIN 1, Biopsy-HPV w/ atypical change | 1st | Negative | Positive | | negative |
| 9 | 7, 7 | LSIL, possible HPV | Biopsy-HPV w/ focal CIN 1 | 2nd | Negative | Negative | | Positive |
| 6 | 7 | LSIL, possible HPV | CIN 1 | 1st | negative | negative | | negative |
| 4 | 14 | Sample with blood | | 1st | negative | Positive | Positive | Positive |
| 5 | 14 | Sample with blood | | 1st | negative | negative | Positive | negative |
| 3 | 16 | ASCUS, may be HSIL | Biopsy-HPV w/ focal CIN 1 | 1st | Positive | Positive | Positive | |
| 2 | 7, 16 | LSIL(1st), ASCUS(2nd HSIL?) | Biopsy-HPV w/ CIN 1 | 2nd | Negative | Positive | | negative |
| 1 | 17, 10 | LSIL(1st), probably progress into invasive cancer (2nd) | Biopsy w/ CIN 3 | 1st | Negative | Positive | Positive | Negative |

Figure 17

SEQUENCE LISTING

<160> NUMBER OF SEQ ID NOS: 27

<210> SEQ ID NO 1
<211> LENGTH: 474
<212> TYPE: DNA
<213> ORGANISM: pappilomavirus

<400> SEQUENCE: 1

```
caccaaaaga gaactgcaat gtttcaggac ccacaggagc gacccagaaa gttaccacag      60
ttatgcacag agctgcaaac aactatacat gatataaat tagaatgtgt gtactgcaag     120
caacagttac tgcgacgtga ggtatatgac tttgcttttc gggatttatg catagtatat     180
agagatggga atccatatgc tgtatgtgat aaatgtttaa agttttattc taaaattagt     240
gagtatagac attattgtta tagtttgtat ggaacaacat tagaacagca atacaacaaa     300
ccgttgtgtg atttgttaat taggtgtatt aactgtcaaa agccactgtg tcctgaagaa     360
aagcaaagac atctggacaa aaagcaaaga ttccataata taaggggtcg gtggaccggt     420
cgatgtatgt cttgttgcag atcatcaaga acacgtagag aaacccagct gtaa           474
```

<210> SEQ ID NO 2
<211> LENGTH: 157
<212> TYPE: PRT
<213> ORGANISM: pappilomavirus

<400> SEQUENCE: 2

```
His Gln Lys Arg Thr Ala Met Phe Gln Asp Pro Gln Glu Arg Pro Arg
1               5                   10                  15
Lys Leu Pro Gln Leu Cys Thr Glu Leu Gln Thr Thr Ile His Asp Ile
            20                  25                  30
Ile Leu Glu Cys Val Tyr Cys Lys Gln Gln Leu Leu Arg Arg Glu Val
        35                  40                  45
Tyr Asp Phe Ala Phe Arg Asp Leu Cys Ile Val Tyr Arg Asp Gly Asn
    50                  55                  60
Pro Tyr Ala Val Cys Asp Lys Cys Leu Lys Phe Tyr Ser Lys Ile Ser
65                  70                  75                  80
Glu Tyr Arg His Tyr Cys Tyr Ser Leu Tyr Gly Thr Thr Leu Glu Gln
                85                  90                  95
Gln Tyr Asn Lys Pro Leu Cys Asp Leu Leu Ile Arg Cys Ile Asn Cys
            100                 105                 110
Gln Lys Pro Leu Cys Pro Glu Glu Lys Gln Arg His Leu Asp Lys Lys
        115                 120                 125
Gln Arg Phe His Asn Ile Arg Gly Arg Trp Thr Gly Arg Cys Met Ser
    130                 135                 140
Cys Cys Arg Ser Ser Arg Thr Arg Arg Glu Thr Gln Leu
145                 150                 155
```

<210> SEQ ID NO 3
<211> LENGTH: 34
<212> TYPE: DNA
<213> ORGANISM: pappilomavirus

<400> SEQUENCE: 3

```
cgcggatccc accaaaagag aactgcaatg tttc                                  34
```

<210> SEQ ID NO 4
<211> LENGTH: 32

<212> TYPE: DNA
<213> ORGANISM: pappilomavirus

<400> SEQUENCE: 4
cccaagcttt tacagctggg tttctctacg tg    32

<210> SEQ ID NO 5
<211> LENGTH: 510
<212> TYPE: DNA
<213> ORGANISM: pappilomavirus

<400> SEQUENCE: 5
atgagaggat cgcatcacca tcaccatcac ggatcccacc aaaagagaac tgcaatgttt    60
caggacccac aggagcgacc cagaaagtta ccacagttat gcacagagct gcaaacaact    120
atacatgata taatattaga atgtgtgtac tgcaagcaac agttactgcg acgtgaggta    180
tatgactttg cttttcggga tttatgcata gtatatagag atgggaatcc atatgctgta    240
tgtgataaat gtttaaagtt ttattctaaa attagtgagt atagacatta ttgttatagt    300
ttgtatggaa caacattaga acagcaatac aacaaaccgt tgtgtgattt gttaattagg    360
tgtattaact gtcaaaagcc actgtgtcct gaagaaaagc aaagacatct ggacaaaaag    420
caaagattcc ataatataag gggtcggtgg accggtcgat gtatgtcttg ttgcagatca    480
tcaagaacac gtagagaaac ccagctgtaa    510

<210> SEQ ID NO 6
<211> LENGTH: 169
<212> TYPE: PRT
<213> ORGANISM: pappilomavirus

<400> SEQUENCE: 6

Met Arg Gly Ser His His His His His His Gly Ser His Gln Lys Arg
1               5                   10                  15
Thr Ala Met Phe Gln Asp Pro Gln Glu Arg Pro Arg Lys Leu Pro Gln
            20                  25                  30
Leu Cys Thr Glu Leu Gln Thr Thr Ile His Asp Ile Ile Leu Glu Cys
        35                  40                  45
Val Tyr Cys Lys Gln Gln Leu Leu Arg Arg Glu Val Tyr Asp Phe Ala
    50                  55                  60
Phe Arg Asp Leu Cys Ile Val Tyr Arg Asp Gly Asn Pro Tyr Ala Val
65                  70                  75                  80
Cys Asp Lys Cys Leu Lys Phe Tyr Ser Lys Ile Ser Glu Tyr Arg His
                85                  90                  95
Tyr Cys Tyr Ser Leu Tyr Gly Thr Thr Leu Glu Gln Gln Tyr Asn Lys
            100                 105                 110
Pro Leu Cys Asp Leu Leu Ile Arg Cys Ile Asn Cys Gln Lys Pro Leu
        115                 120                 125
Cys Pro Glu Glu Lys Gln Arg His Leu Asp Lys Lys Gln Arg Phe His
    130                 135                 140
Asn Ile Arg Gly Arg Trp Thr Gly Arg Cys Met Ser Cys Cys Arg Ser
145                 150                 155                 160
Ser Arg Thr Arg Arg Glu Thr Gln Leu
                165

<210> SEQ ID NO 7
<211> LENGTH: 300
<212> TYPE: DNA
<213> ORGANISM: Papillomavirus sylvilagi -continued

<400> SEQUENCE: 7

```
gatcccatgg agatacacct acattgcatg aatatatgtt agatttgcaa ccagagacaa    60
ctgatctcta ctgttatgag caattaaatg acagctcaga ggaggaggat gaaatagatg   120
gtccagctgg acaagcagaa ccggacagag cccattacaa tattgtaacc ttttgttgca   180
agtgtgactc tacgcttcgg ttgtgcgtac aaagcacaca cgtagacatt cgtactttgg   240
aagacctgtt aatgggcaca ctaggaattg tgtgccccat ctgttctcag aaaccataag   300
```

<210> SEQ ID NO 8
<211> LENGTH: 97
<212> TYPE: PRT
<213> ORGANISM: pappilomavirus

<400> SEQUENCE: 8

```
His Gly Asp Thr Pro Thr Leu His Glu Tyr Met Leu Asp Leu Gln Pro
 1               5                  10                  15
Glu Thr Thr Asp Leu Tyr Cys Tyr Glu Gln Leu Asn Asp Ser Ser Glu
            20                  25                  30
Glu Glu Asp Glu Ile Asp Gly Pro Ala Gly Gln Ala Glu Pro Asp Arg
        35                  40                  45
Ala His Tyr Asn Ile Val Thr Phe Cys Cys Lys Cys Asp Ser Thr Leu
    50                  55                  60
Arg Leu Cys Val Gln Ser Thr His Val Asp Ile Arg Thr Leu Glu Asp
65                  70                  75                  80
Leu Leu Met Gly Thr Leu Gly Ile Val Cys Pro Ile Cys Ser Gln Lys
                85                  90                  95
Pro
```

<210> SEQ ID NO 9
<211> LENGTH: 31
<212> TYPE: DNA
<213> ORGANISM: pappilomavirus

<400> SEQUENCE: 9

```
cgcggatccc atggagatac acctacattg c                                   31
```

<210> SEQ ID NO 10
<211> LENGTH: 32
<212> TYPE: DNA
<213> ORGANISM: pappilomavirus

<400> SEQUENCE: 10

```
ccggaattct tatggtttct gagaacagat gg                                  32
```

<210> SEQ ID NO 11
<211> LENGTH: 972
<212> TYPE: DNA
<213> ORGANISM: pappilomavirus

<400> SEQUENCE: 11

```
atgtccccta ctaggttta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg agtttcccca tcttccctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
```

```
gatattagat acggtgtttc gagaattgca tatagtaaag actttgaaac tctcaaagtt      360
gattttctta gcaagctacc tgaaatgctg aaaatgttcg aagatcgttt atgtcataaa      420
acatatttaa atggtgatca tgtaacccat cctgacttca tgttgtatga cgctcttgat      480
gttgttttat acatggaccc aatgtgcctg gatgcgttcc caaaattagt ttgttttaaa      540
aaacgtattg aagctatccc acaaattgat aagtacttga atccagcaa gtatatagca      600 tggcctttgc agggctggca agccacgttt ggtggtggcg accatcctcc aaaatcggat      660
ctggttccgc gtggatccca tggagataca cctacattgc atgaatatat gttagatttg      720
caaccagaga caactgatct ctactgttat gagcaattaa atgacagctc agaggaggag      780
gatgaaatag atggtccagc tggacaagca gaaccggaca gagcccatta caatattgta      840 acctttgtt gcaagtgtga ctctacgctt cggttgtgcg tacaaagcac acacgtagac      900
attcgtactt tggaagacct gttaatgggc acactaggaa ttgtgtgccc catctgttct      960
cagaaaccat aa                                                         972
```

<210> SEQ ID NO 12
<211> LENGTH: 323
<212> TYPE: PRT
<213> ORGANISM: pappilomavirus

<400> SEQUENCE: 12

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser His Gly Asp Thr Pro Thr Leu His Glu Tyr Met Leu Asp Leu
225                 230                 235                 240

Gln Pro Glu Thr Thr Asp Leu Tyr Cys Tyr Glu Gln Leu Asn Asp Ser
                245                 250                 255
```

```
Ser Glu Glu Glu Asp Glu Ile Asp Gly Pro Ala Gly Gln Ala Glu Pro
            260                 265                 270

Asp Arg Ala His Tyr Asn Ile Val Thr Phe Cys Cys Lys Cys Asp Ser
        275                 280                 285

Thr Leu Arg Leu Cys Val Gln Ser Thr His Val Asp Ile Arg Thr Leu
    290                 295                 300

Glu Asp Leu Leu Met Gly Thr Leu Gly Ile Val Cys Pro Ile Cys Ser
305                 310                 315                 320

Gln Lys Pro

<210> SEQ ID NO 13
<211> LENGTH: 1602
<212> TYPE: DNA
<213> ORGANISM: pappilomavirus

<400> SEQUENCE: 13
```

| | | | | | |
|---|---|---|---|---|---|
| tcgagatgca | ggtgactttt | atttacatcc | tagttattac | atgttacgaa | aacgacgtaa | 60 |
| acgtttacca | tatttttttt | cagatgtctc | tttggctgcc | tagtgaggcc | actgtctact | 120 |
| tgcctcctgt | cccagtatct | aaggttgtaa | gcacggatga | atatgttgca | cgcacaaaca | 180 |
| tatattatca | tgcaggaaca | tccagactac | ttgcagttgg | acatccctat | tttcctatta | 240 |
| aaaaacctaa | caataacaaa | atattagttc | ctaaagtatc | aggattacaa | tacagggtat | 300 |
| ttagaataca | tttacctgac | cccaataagt | ttggttttcc | tgacacctca | ttttataatc | 360 |
| cagatacaca | gcggctggtt | tgggcctgtg | taggtgttga | ggtaggtcgt | ggtcagccat | 420 |
| taggtgtggg | cattagtggc | catcctttat | taaataaatt | ggatgacaca | gaaaatgcta | 480 |
| gtgcttatgc | agcaaatgca | ggtgtggata | atagagaatg | tatatctatg | gattacaaac | 540 |
| aaacacaatt | gtgtttaatt | ggttgcaaac | cacctatagg | gaacactggg | gcaaaggat | 600 |
| ccccatgtac | caatgttgca | gtaaatccag | gtgattgtcc | accattagag | ttaataaaca | 660 |
| cagttattca | ggatggtgat | atggttcata | ctggctttgg | tgctatggac | tttactacat | 720 |
| tacaggctaa | caaagtgaa | gttccactgg | atatttgtac | atctatttgc | aaatatccag | 780 |
| attatattaa | aatggtgtca | gaaccatatg | gcgacagctt | attttttat | ttacgaaggg | 840 |
| aacaaatgtt | tgttagacat | ttatttaata | gggctgtac | tgttggtgaa | aatgtaccag | 900 |
| acgatttata | cattaaaggc | tctgggtcta | ctgcaaattt | agccagttca | aattattttc | 960 |
| ctacacctag | tggttctatg | gttacctctg | atgcccaaat | attcaataaa | ccttattggt | 1020 |
| tacaacgagc | acagggccac | aataatggca | tttgttgggg | taaccaacta | tttgttactg | 1080 |
| ttgttgatac | tacacgcagt | acaaatatgt | cattatgtgc | tgccatatct | acttcagaaa | 1140 |
| ctacatataa | aaatactaac | tttaaggagt | acctacgaca | tggggaggaa | tatgatttac | 1200 |
| agttttatttt | tcaactgtgc | aaaataacct | taactgcaga | cgttatgaca | tacatacatt | 1260 |
| ctatgaattc | cactattttg | gaggactgga | attttggtct | acaacctccc | ccaggaggca | 1320 |
| cactagaaga | tacttatagg | tttgtaaccc | aggcaattgc | ttgtcaaaaa | catacacctc | 1380 |
| cagcacctaa | agaagatgat | ccccttaaaa | aatacacttt | tgggaagta | aatttaaagg | 1440 |
| aaaagttttc | tgcagaccta | gatcagtttc | ctttaggacg | caaattttta | ctacaagcag | 1500 |
| gattgaaggc | caaaccaaaa | tttacattag | gaaaacgaaa | agctcacccc | accacctcat | 1560 |
| ctacctctac | aactgctaaa | cgcaaaaaac | gtaagctgta | aa | | 1602 |

```
<210> SEQ ID NO 14
```

```
<211> LENGTH: 531
<212> TYPE: PRT
<213> ORGANISM: pappilomavirus

<400> SEQUENCE: 14
```

| | | | | | | | | | | | | | | | |
|---|---|---|---|---|---|---|---|---|---|---|---|---|---|---|---|
| Met | Gln | Val | Thr | Phe | Ile | Tyr | Ile | Leu | Val | Ile | Thr | Cys | Tyr | Glu | Asn |
| 1 | | | | 5 | | | | | 10 | | | | | 15 | |
| Asp | Val | Asn | Val | Tyr | His | Ile | Phe | Phe | Gln | Met | Ser | Leu | Trp | Leu | Pro |
| | | | 20 | | | | | 25 | | | | | 30 | | |
| Ser | Glu | Ala | Thr | Val | Tyr | Leu | Pro | Pro | Val | Pro | Val | Ser | Lys | Val | Val |
| | | | | 35 | | | | | 40 | | | | | 45 | |
| Ser | Thr | Asp | Glu | Tyr | Val | Ala | Arg | Thr | Asn | Ile | Tyr | Tyr | His | Ala | Gly |
| | 50 | | | | | 55 | | | | | 60 | | | | |
| Thr | Ser | Arg | Leu | Leu | Ala | Val | Gly | His | Pro | Tyr | Phe | Pro | Ile | Lys | Lys |
| 65 | | | | | 70 | | | | | 75 | | | | | 80 |
| Pro | Asn | Asn | Asn | Lys | Ile | Leu | Val | Pro | Lys | Val | Ser | Gly | Leu | Gln | Tyr |
| | | | | 85 | | | | | 90 | | | | | 95 | |
| Arg | Val | Phe | Arg | Ile | His | Leu | Pro | Asp | Pro | Asn | Lys | Phe | Gly | Phe | Pro |
| | | | 100 | | | | | 105 | | | | | 110 | | |
| Asp | Thr | Ser | Phe | Tyr | Asn | Pro | Asp | Thr | Gln | Arg | Leu | Val | Trp | Ala | Cys |
| | | | | 115 | | | | | 120 | | | | | 125 | |
| Val | Gly | Val | Glu | Val | Gly | Arg | Gly | Gln | Pro | Leu | Gly | Val | Gly | Ile | Ser |
| | 130 | | | | | 135 | | | | | 140 | | | | |
| Gly | His | Pro | Leu | Leu | Asn | Lys | Leu | Asp | Asp | Thr | Glu | Asn | Ala | Ser | Ala |
| 145 | | | | | 150 | | | | | 155 | | | | | 160 |
| Tyr | Ala | Ala | Asn | Ala | Gly | Val | Asp | Asn | Arg | Glu | Cys | Ile | Ser | Met | Asp |
| | | | | 165 | | | | | 170 | | | | | 175 | |
| Tyr | Lys | Gln | Thr | Gln | Leu | Cys | Leu | Ile | Gly | Cys | Lys | Pro | Pro | Ile | Gly |
| | | | 180 | | | | | 185 | | | | | 190 | | |
| Glu | His | Trp | Gly | Lys | Gly | Ser | Pro | Cys | Thr | Asn | Val | Ala | Val | Asn | Pro |
| | | | | 195 | | | | | 200 | | | | | 205 | |
| Gly | Asp | Cys | Pro | Pro | Leu | Glu | Leu | Ile | Asn | Thr | Val | Ile | Gln | Asp | Gly |
| | 210 | | | | | 215 | | | | | 220 | | | | |
| Asp | Met | Val | His | Thr | Gly | Phe | Gly | Ala | Met | Asp | Phe | Thr | Thr | Leu | Gln |
| 225 | | | | | 230 | | | | | 235 | | | | | 240 |
| Ala | Asn | Lys | Ser | Glu | Val | Pro | Leu | Asp | Ile | Cys | Thr | Ser | Ile | Cys | Lys |
| | | | | 245 | | | | | 250 | | | | | 255 | |
| Tyr | Pro | Asp | Tyr | Ile | Lys | Met | Val | Ser | Glu | Pro | Tyr | Gly | Asp | Ser | Leu |
| | | | 260 | | | | | 265 | | | | | 270 | | |
| Phe | Phe | Tyr | Leu | Arg | Arg | Glu | Gln | Met | Phe | Val | Arg | His | Leu | Phe | Asn |
| | | | | 275 | | | | | 280 | | | | | 285 | |
| Arg | Ala | Gly | Thr | Val | Gly | Glu | Asn | Val | Pro | Asp | Asp | Leu | Tyr | Ile | Lys |
| | 290 | | | | | 295 | | | | | 300 | | | | |
| Gly | Ser | Gly | Ser | Thr | Ala | Asn | Leu | Ala | Ser | Ser | Asn | Tyr | Phe | Pro | Thr |
| 305 | | | | | 310 | | | | | 315 | | | | | 320 |
| Pro | Ser | Gly | Ser | Met | Val | Thr | Ser | Asp | Ala | Gln | Ile | Phe | Asn | Lys | Pro |
| | | | | 325 | | | | | 330 | | | | | 335 | |
| Tyr | Trp | Leu | Gln | Arg | Ala | Gln | Gly | His | Asn | Asn | Gly | Ile | Cys | Trp | Gly |
| | | | 340 | | | | | 345 | | | | | 350 | | |
| Asn | Gln | Leu | Phe | Val | Thr | Val | Val | Asp | Thr | Thr | Arg | Ser | Thr | Asn | Met |
| | | | | 355 | | | | | 360 | | | | | 365 | |
| Ser | Leu | Cys | Ala | Ala | Ile | Ser | Thr | Ser | Glu | Thr | Thr | Tyr | Lys | Asn | Thr |
| | 370 | | | | | 375 | | | | | 380 | | | | |
| Asn | Phe | Lys | Glu | Tyr | Leu | Arg | His | Gly | Glu | Glu | Tyr | Asp | Leu | Gln | Phe |

```
                385                 390                 395                 400
Ile Phe Gln Leu Cys Lys Ile Thr Leu Thr Ala Asp Val Met Thr Tyr
                405                 410                 415
Ile His Ser Met Asn Ser Thr Ile Leu Glu Asp Trp Asn Phe Gly Leu
            420                 425                 430
Gln Pro Pro Gly Gly Thr Leu Glu Asp Thr Tyr Arg Phe Val Thr
        435                 440                 445
Gln Ala Ile Ala Cys Gln Lys His Thr Pro Ala Pro Lys Glu Asp
    450                 455                 460
Asp Pro Leu Lys Lys Tyr Thr Phe Trp Glu Val Asn Leu Lys Glu Lys
465                 470                 475                 480
Phe Ser Ala Asp Leu Asp Gln Phe Pro Leu Gly Arg Lys Phe Leu Leu
                485                 490                 495
Gln Ala Gly Leu Lys Ala Lys Pro Lys Phe Thr Leu Gly Lys Arg Lys
                500                 505                 510
Ala Thr Pro Thr Thr Ser Ser Thr Ser Thr Thr Ala Lys Arg Lys Lys
            515                 520                 525
Arg Lys Leu
    530

<210> SEQ ID NO 15
<211> LENGTH: 34
<212> TYPE: DNA
<213> ORGANISM: pappilomavirus

<400> SEQUENCE: 15
ccgctcgaga tgcaggtgac ttttatttac atcc                                    34

<210> SEQ ID NO 16
<211> LENGTH: 34
<212> TYPE: DNA
<213> ORGANISM: pappilomavirus

<400> SEQUENCE: 16
cccaagcttt tacagcttac gttttttgcg ttta                                    34

<210> SEQ ID NO 17
<211> LENGTH: 1716
<212> TYPE: DNA
<213> ORGANISM: pappilomavirus

<400> SEQUENCE: 17
atgccgcggg gttctcatca tcatcatcat catggtatgg ctagcatgac tggtggacag        60
caaatgggtc gggatctgta cgacgatgac gataaggatc gatggggatc cgagctcgag       120
atgcaggtga cttttattta catcctagtt attacatgtt acgaaaacga cgtaaacgtt       180
taccatattt ttttcagat gtctctttgg ctgcctagtg aggccactgt ctacttgcct       240
cctgtcccag tatctaaggt tgtaagcacg gatgaatatg ttgcacgcac aaacatatat       300
tatcatgcag gaacatccag actacttgca gttggacatc cctatttttcc tattaaaaaa       360 cctaacaata caaaatatt agttcctaaa gtatcaggat acaatacag ggtatttaga        420 atacatttac ctgacccca taagtttggt tttcctgaca cctcatttta taatccagat       480
acacagcggc tggtttgggc ctgtgtaggt gttgaggtag tcgtggtca gccattaggt       540 gtgggcatta gtggccatcc tttattaaat aaattggatg acacagaaaa tgctagtgct       600
tatgcagcaa atgcaggtgt ggataataga gaatgtatat ctatggatta caaacaaaca       660
```

-continued

```
caattgtgtt taattggttg caaaccacct ataggggaac actggggcaa aggatcccca      720
tgtaccaatg ttgcagtaaa tccaggtgat tgtccaccat tagagttaat aaacacagtt      780
attcaggatg gtgatatggt tcatactggc tttggtgcta tggactttac tacattacag      840
gctaacaaaa gtgaagttcc actggatatt tgtacatcta tttgcaaata tccagattat      900
attaaaatgg tgtcagaacc atatggcgac agcttatttt tttatttacg aagggaacaa      960
atgtttgtta gacatttatt taatagggct ggtactgttg gtgaaaatgt accagacgat     1020
ttatacatta aaggctctgg gtctactgca aatttagcca gttcaaatta ttttcctaca     1080
cctagtggtt ctatggttac ctctgatgcc caaatattca ataaaccta ttggttacaa      1140
cgagcacagg gccacaataa tggcatttgt tggggtaacc aactattgt tactgttgtt      1200
gatactacac gcagtacaaa tatgtcatta tgtgctgcca tatctacttc agaaactaca     1260
tataaaaata ctaactttaa ggagtaccta cgacatgggg aggaatatga tttacagttt     1320
atttttcaac tgtgcaaaat aaccttaact gcagacgtta tgacatacat acattctatg     1380
aattccacta ttttggagga ctggaatttt ggtctacaac tcccccagg aggcacacta     1440
gaagatactt ataggtttgt aacccaggca attgcttgtc aaaaacatac acctccagca     1500
cctaagaag atgatcccct aaaaaatac acttttggg aagtaaattt aaggaaaag         1560
ttttctgcag acctagatca gtttccttta ggacgcaaat ttttactaca agcaggattg     1620
aaggccaaac caaatttac attaggaaaa cgaaaagcta cacccaccac ctcatctacc     1680
tctacaactg ctaaacgcaa aaaacgtaag ctgtaa                               1716
```

<210> SEQ ID NO 18
<211> LENGTH: 571
<212> TYPE: PRT
<213> ORGANISM: pappilomavirus

<400> SEQUENCE: 18

```
Met Pro Arg Gly Ser His His His His His Gly Met Ala Ser Met
1               5                   10                  15

Thr Gly Gly Gln Gln Met Gly Arg Asp Leu Tyr Asp Asp Asp Lys
            20                  25                  30

Asp Arg Trp Gly Ser Glu Leu Glu Met Gln Val Thr Phe Ile Tyr Ile
        35                  40                  45

Leu Val Ile Thr Cys Tyr Glu Asn Asp Val Asn Val Tyr His Ile Phe
    50                  55                  60

Phe Gln Met Ser Leu Trp Leu Pro Ser Glu Ala Thr Val Tyr Leu Pro
65                  70                  75                  80

Pro Val Pro Val Ser Lys Val Val Ser Thr Asp Glu Tyr Val Ala Arg
                85                  90                  95

Thr Asn Ile Tyr Tyr His Ala Gly Thr Ser Arg Leu Leu Ala Val Gly
            100                 105                 110

His Pro Tyr Phe Pro Ile Lys Lys Pro Asn Asn Lys Ile Leu Val
        115                 120                 125

Pro Lys Val Ser Gly Leu Gln Tyr Arg Val Phe Arg Ile His Leu Pro
    130                 135                 140

Asp Pro Asn Lys Phe Gly Phe Pro Asp Thr Ser Phe Tyr Asn Pro Asp
145                 150                 155                 160

Thr Gln Arg Leu Val Trp Ala Cys Val Gly Val Glu Val Gly Arg Gly
                165                 170                 175

Gln Pro Leu Gly Val Gly Ile Ser Gly His Pro Leu Leu Asn Lys Leu
            180                 185                 190
```

```
Asp Asp Thr Glu Asn Ala Ser Ala Tyr Ala Asn Ala Gly Val Asp
            195                 200                 205

Asn Arg Glu Cys Ile Ser Met Asp Tyr Lys Gln Thr Gln Leu Cys Leu
            210                 215                 220

Ile Gly Cys Lys Pro Pro Ile Gly Glu His Trp Gly Lys Gly Ser Pro
225                 230                 235                 240

Cys Thr Asn Val Ala Val Asn Pro Gly Asp Cys Pro Pro Leu Glu Leu
                245                 250                 255

Ile Asn Thr Val Ile Gln Asp Gly Asp Met Val His Thr Gly Phe Gly
            260                 265                 270

Ala Met Asp Phe Thr Thr Leu Gln Ala Asn Lys Ser Glu Val Pro Leu
            275                 280                 285

Asp Ile Cys Thr Ser Ile Cys Lys Tyr Pro Asp Tyr Ile Lys Met Val
            290                 295                 300

Ser Glu Pro Tyr Gly Asp Ser Leu Phe Phe Tyr Leu Arg Arg Glu Gln
305                 310                 315                 320

Met Phe Val Arg His Leu Phe Asn Arg Ala Gly Thr Val Gly Glu Asn
                325                 330                 335

Val Pro Asp Asp Leu Tyr Ile Lys Gly Ser Gly Ser Thr Ala Asn Leu
            340                 345                 350

Ala Ser Ser Asn Tyr Phe Pro Thr Pro Ser Gly Ser Met Val Thr Ser
            355                 360                 365

Asp Ala Gln Ile Phe Asn Lys Pro Tyr Trp Leu Gln Arg Ala Gln Gly
            370                 375                 380

His Asn Asn Gly Ile Cys Trp Gly Asn Gln Leu Phe Val Thr Val Val
385                 390                 395                 400

Asp Thr Thr Arg Ser Thr Asn Met Ser Leu Cys Ala Ala Ile Ser Thr
                405                 410                 415

Ser Glu Thr Thr Tyr Lys Asn Thr Asn Phe Lys Glu Tyr Leu Arg His
            420                 425                 430

Gly Glu Glu Tyr Asp Leu Gln Phe Ile Phe Gln Leu Cys Lys Ile Thr
            435                 440                 445

Leu Thr Ala Asp Val Met Thr Tyr Ile His Ser Met Asn Ser Thr Ile
450                 455                 460

Leu Glu Asp Trp Asn Phe Gly Leu Gln Pro Pro Pro Gly Gly Thr Leu
465                 470                 475                 480

Glu Asp Thr Tyr Arg Phe Val Thr Gln Ala Ile Ala Cys Gln Lys His
                485                 490                 495

Thr Pro Pro Ala Pro Lys Glu Asp Asp Pro Leu Lys Lys Tyr Thr Phe
            500                 505                 510

Trp Glu Val Asn Leu Lys Glu Lys Phe Ser Ala Asp Leu Asp Gln Phe
            515                 520                 525

Pro Leu Gly Arg Lys Phe Leu Leu Gln Ala Gly Leu Lys Ala Lys Pro
            530                 535                 540

Lys Phe Thr Leu Gly Lys Arg Lys Ala Thr Pro Thr Thr Ser Ser Thr
545                 550                 555                 560

Ser Thr Thr Ala Lys Arg Lys Arg Lys Leu
                565                 570

<210> SEQ ID NO 19
<211> LENGTH: 322
<212> TYPE: PRT
<213> ORGANISM: pappilomavirus
```

<400> SEQUENCE: 19

```
Met Ala Ser Met Thr Gly Gly Gln Gln Met Gly Arg Gly Ser Gln Val
1               5                   10                  15
Thr Phe Ile Tyr Ile Leu Val Ile Thr Cys Tyr Glu Asn Asp Val Asn
            20                  25                  30
Val Tyr His Ile Phe Phe Gln Met Ser Leu Trp Leu Pro Ser Glu Ala
        35                  40                  45
Thr Val Tyr Leu Pro Pro Val Pro Val Ser Lys Val Val Ser Thr Asp
    50                  55                  60
Glu Tyr Val Ala Arg Thr Asn Ile Tyr Tyr His Ala Gly Thr Ser Arg
65                  70                  75                  80
Leu Leu Ala Val Gly His Pro Tyr Phe Pro Ile Lys Lys Pro Asn Asn
                85                  90                  95
Asn Lys Ile Leu Val Pro Lys Val Ser Gly Leu Gln Tyr Arg Val Phe
            100                 105                 110
Arg Ile His Leu Pro Asp Pro Asn Lys Phe Gly Phe Pro Asp Thr Ser
        115                 120                 125
Phe Tyr Asn Pro Asp Thr Gln Arg Leu Val Trp Ala Cys Val Gly Val
130                 135                 140
Glu Val Gly Arg Gly Gln Pro Leu Gly Val Gly Ile Ser Gly His Pro
145                 150                 155                 160
Leu Leu Asn Lys Leu Asp Asp Thr Glu Asn Ala Ser Ala Tyr Ala Ala
                165                 170                 175
Asn Ala Gly Val Asp Asn Arg Glu Cys Ile Ser Met Asp Tyr Lys Gln
            180                 185                 190
Thr Gln Leu Cys Leu Ile Gly Cys Lys Pro Pro Ile Gly Glu His Trp
        195                 200                 205
Gly Lys Gly Ser Pro Cys Thr Asn Val Ala Val Asn Pro Gly Asp Cys
210                 215                 220
Pro Pro Leu Glu Leu Ile Asn Thr Val Ile Gln Asp Gly Asp Met Val
225                 230                 235                 240
His Thr Gly Phe Gly Ala Met Asp Phe Thr Thr Leu Gln Ala Asn Lys
                245                 250                 255
Ser Glu Val Pro Leu Asp Ile Cys Thr Ser Ile Cys Lys Tyr Pro Asp
            260                 265                 270
Tyr Ile Lys Met Val Ser Glu Pro Tyr Gly Asp Ser Leu Phe Phe Tyr
        275                 280                 285
Leu Arg Arg Glu Gln Met Phe Val Arg His Leu Phe Asn Arg Ala Gly
290                 295                 300
Thr Val Gly Glu Asn Val Pro Asp Asp Leu Val Glu His His His His
305                 310                 315                 320
His His
```

<210> SEQ ID NO 20
<211> LENGTH: 20
<212> TYPE: DNA
<213> ORGANISM: pappilomavirus
<220> FEATURE:
<221> NAME/KEY: misc_feature
<222> LOCATION: (3)..(3)
<223> OTHER INFORMATION: n is a, c, g, or t

<400> SEQUENCE: 20
gcncargghc ayaayaatgg                                              20

<210> SEQ ID NO 21
<211> LENGTH: 23
<212> TYPE: DNA
<213> ORGANISM: pappilomavirus

<400> SEQUENCE: 21
gtdgtatcha cmhcagtaac aaa                                            23

<210> SEQ ID NO 22
<211> LENGTH: 64
<212> TYPE: DNA
<213> ORGANISM: pappilomavirus

<400> SEQUENCE: 22
cvcaggghca yaayaatggc atttgttggg gtaaccaact atttgttact gttgtdgaya    60 cyac                                                                 64

<210> SEQ ID NO 23
<211> LENGTH: 20
<212> TYPE: DNA
<213> ORGANISM: pappilomavirus

<400> SEQUENCE: 23
gttactgcga cgtgaggtat                                                20

<210> SEQ ID NO 24
<211> LENGTH: 20
<212> TYPE: DNA
<213> ORGANISM: pappilomavirus

<400> SEQUENCE: 24
gtttcaggac ccacaggagc                                                20

<210> SEQ ID NO 25
<211> LENGTH: 20
<212> TYPE: DNA
<213> ORGANISM: pappilomavirus

<400> SEQUENCE: 25
caacggtttg ttgtattgct                                                20

<210> SEQ ID NO 26
<211> LENGTH: 181
<212> TYPE: DNA
<213> ORGANISM: pappilomavirus

<400> SEQUENCE: 26
gttactgcga cgtgaggtat atgactttgc ttttcgggat ttatgcatag tatatagaga    60
tgggaatcca tatgctgtat gtgataaatg tttaaagttt tattctaaaa ttagtgagta   120
tagacattat tgtttatagtt tgtatggaac aacattagaa cagcaataca acaaaccgtt   180
g                                                                   181

<210> SEQ ID NO 27
<211> LENGTH: 286
<212> TYPE: DNA
<213> ORGANISM: pappilomavirus

<400> SEQUENCE: 27
gtttcaggac ccacaggagc gacccagaaa gttaccacag ttatgcacag agctgcaaac    60
aactatacat gatataatat tagaatgtgt gtactgcaag caacagttac tgcgacgtga   120

-continued

```
ggtatatgac tttgcttttc gggatttatg catagtatat agagatggga atccatatgc      180
tgtatgtgat aaatgtttaa agttttattc taaaattagt gagtatagac attattgtta      240
tagtttgtat ggaacaacat tagaacagca atacaacaaa ccgttg                    286
```

DETECTION METHOD FOR HUMAN PAPPILOMAVIRUS (HPV) AND ITS APPLICATION IN CERVICAL CANCER

CROSS-REFERENCE TO RELATED APPLICATIONS

This application claims benefit of U.S. provisional patent application Ser. No. 60/737,152, filed Nov. 15, 2005, which is herein incorporated by reference.

BACKGROUND OF THE INVENTION

Cancer of the uterine cervix or cervical cancer is the second most common cancer in women worldwide. Although screening programs to identify precursor lesions of cervical cancer have contributed to a reduction in mortality and morbidity, 500,000 new cases of invasive cervical cancer are diagnosed worldwide and 230,000 women die of cervical cancer annually. Early detection and diagnosis is critical for survival of cervical cancer.

Infection by human papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is highest among young women and about 20 millions of sexually active men and women worldwide are currently infected. Approximately 1% of the population has genital warts and 4% of women have cervical precancerous lesions, such as low grade of squamous intraepithelial lesion (LGSIL) or high grade of squamous intraepithelial lesion (HSIL). The presence of these lesions, preferentially observed in women aged 35-40 yrs, are at high risk of progression toward invasive cancer.

There are more than one hundred genetic types of human papillomaviruses identified so far and only a relative few types of HPV, such as HPV-16, -18, -31, -33, -35, -45, -51, -52 and -56, etc., involve high risk of progression from HPV infected genital tissue lesions to invasive cervical cancer. Infection with the vast majority of HPV types, such as HPV-6 and -11, etc., are transient with no permanent changes in genital tissues and are at low risk for developing into invasive cervical cancer. However, the development of cervical cancer is a multiple step process that cannot be explained simply by infection with specific types of HPV. Persistent infections with HPVs in high risk group are essential but not exclusively required for the initiation of cervical carcinogenesis. It is found that younger age group women are often infected with HPV; however, clinical information reveals that most latent or asymptomatic infections with high risk HPV types as well as early dysplastic lesions (CIN 1) are usually self-limited and regress spontaneously. There is a high level of correlation between long term persistent infections with only few high-risk HPV types and the induction of advanced CIN 2/CIN 3 lesions and/or the progression to invasive cancer.

One additional event that appears to play a role in tumor progression is the integration of HPV DNA genome into host genome, which frequently disrupts the open reading frame for an early viral gene, E2, resulting in over-expression of two important viral E6 and E7 oncoproteins and transformation of the host cells. Since almost all cervical cancer cases harbor high risk-HPV genomes, screening with HPV infection is important, especially long term infection with high risk HPV types. Other factors and mutational or secondary genetic events may also be important in the progression and pathogenesis of invasive cervical cancers, including recombination, integration of viral genes to host cell chromosomes, chromosomal rearrangements, loss of constitutional heterozygosity, and proto-oncogene activation.

In the past, screening for cervical cancer is based on conventional cytology by papanicolaou (Pap) smear and suspicious smears are followed up with colposcopy, and/or histological biopsy. The use of cytological screening lead to a remarkable reduction in the mortality of cervical cancer. However, due to subjective test criteria, drawbacks of pap smear tests include difficulty in obtaining samples, poor inter- and intra-observer agreement, a high rate of false negatives (up to 20%) and false positive, the requirements for specialized labs staffed with highly trained personnel, and inability to identify a large proportion of HPV-infected persons. More reproducible assays are needed to improve the current screening method and avoid unnecessary medical intervention and psychological distress for the affected women. Nucleic acid methods, such as "DNA Hybrid Capture", have been developed, but are not ideal primarily due to their high cost, assay operation procedures, and the requirements for facility, equipment, and highly trained personnel. What is needed is a low cost, simple, sensitive and specific assay that can be performed on routine practice of a clinical lab or doctor office.

Attempts to detect the presence of HPV related antibodies in a human subject by ELISA (enzyme linked immunoabsorbant assays) generally lead to extremely low assay sensitivity and thus can not be developed into a commercially suitable diagnostic test. Most of these ELISA assays target a single viral protein or short peptide fragments, which were not able to interact well or bind strongly and specifically to antibodies from the human subject. The assay specificity and sensitivity are so low such that even using samples from patients confirmed with HPV associated invasive cervical cancer, only 53% of the patient samples were found positive for HPV infection. Thus, there is no successful ELISA assay available as a diagnostic tool for clinical samples.

Therefore, there is a need to develop methods and assays for early detection of HPV infection and assisting in diagnosis of cervical cancer.

SUMMARY OF THE INVENTION

Embodiments of the invention generally relate to various methods, detection assays, kits, polypeptides, recombinant proteins, antibodies, and nucleic acids useful for detecting general HPV infection as well as high risk HPV infection. In one embodiment, a method of screening a human subject of papillomavirus infection includes obtaining a clinical sample from the human subject, obtaining a first recombinant protein encoded by an early gene of a papillomavirus, and obtaining a second recombinant protein encoded by a late gene of the papillomavirus. The method further includes conducting one or more immunological assays on the clinical sample from the human subject, detecting the presence of an antibody to the first recombinant protein in the human subject using the first recombinant protein, and detecting the presence of an antibody to the second recombinant protein in the human subject using the second recombinant protein.

In another embodiment, a method of screening a human subject infected with a human papillomavirus includes obtaining a clinical sample from the human subject, conducting a nucleic acid hybridization assay on the clinical sample, detecting the presence of a papillomavirus genome in the clinical sample from the human subject, and conducting one or more immunological assays on the clinical sample. The one or more immunological assays can be performed independently or concurrently of the nucleic acid hybridization assay using the same or different clinical sample but from the same human subject. The one or more immunological assays are performed to detect the presence of an antibody to an early papillomavirus viral protein or the presence of the early papillomavirus viral protein in the clinical sample using a first recombinant protein of the early papillomavirus viral protein. Further, the presence of an antibody to a late papillomavirus viral protein or the presence of the papillomavirus late viral protein in the clinical sample is detected using a second recombinant protein of the late papillomavirus viral protein in the same or different immunological assays as the immunological assay performed using the first recombinant protein independently or concurrently.

In still another embodiment, a method of screening a human subject of high risk human papillomavirus infection is provided. The method includes obtaining a clinical sample from the human subject, obtaining a first recombinant protein purified from a first protein expression system with a first expression vector having a portion of nucleic acid sequence corresponding to the full length nucleic acid sequence of an early papillomavirus gene, and obtaining a second recombinant protein purified from a second protein expression system with a second expression vector having a portion of nucleic acid sequence corresponding to the full length nucleic acid sequence of a late papillomavirus gene. Further, one or more immunological assays are conducted on the clinical sample to detect the presence of an antibody to a viral oncoprotein or the presence of the viral oncoprotein in the clinical sample using the first recombinant protein, and the presence of an antibody to a viral capsid protein or the presence of the viral capsid protein in the clinical sample using the second recombinant protein.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 14 illustrates a comparison of the results from E6 antibody test with E7 antibody test using cervical samples from human subjects according to one or more embodiments of the invention.

FIG. 15 illustrates a comparison of the results from antibody tests with antigen test using cervical samples from human subjects according to one or more embodiments of the invention.

FIG. 16 illustrates the results from E6 Ab tests, L1 Ab tests, and PCR tests using cervical samples from human subjects according to one or more embodiments of the invention for 173 subjects with normal pap smear scores.

FIG. 17 illustrates the results of the E6 Ab tests, L1 Ab tests, and PCR L1 tests using cervical samples from human subjects according to one or more embodiments of the invention for 20 subjects with abnormal pap smear scores.

DETAILED DESCRIPTION

Embodiments of the invention provide various methods, detection assays, and kits, polypeptides, recombinant proteins, antibodies, and nucleic acids useful for detecting general HPV infection as well as infection with high risk HPV types. For example, detection of HPV DNAs, genomes, early viral proteins, late viral proteins, oncoproteins, and/or capsid proteins by nucleic acid hybridization assays and immunological assays as described herein can be used in early clinical screening for HPV infection. It can also be used in diagnosing HPV-associated carcinomas of the uterine cervix, as well as those cases associated with epithelial cell abnormalities induced by HPV infection, pre-malignant and malignant HPV-associated epithelial cell lesions, and those at risk of developing HPV-associated cervical carcinoma and adenocarcinoma. The methods as described herein can be used independently or as an adjunct screening tool to convention cytological papanicolaou smear tests or histological tests and the results thereof can be compared fro follow-up patient management.

Figure 1:
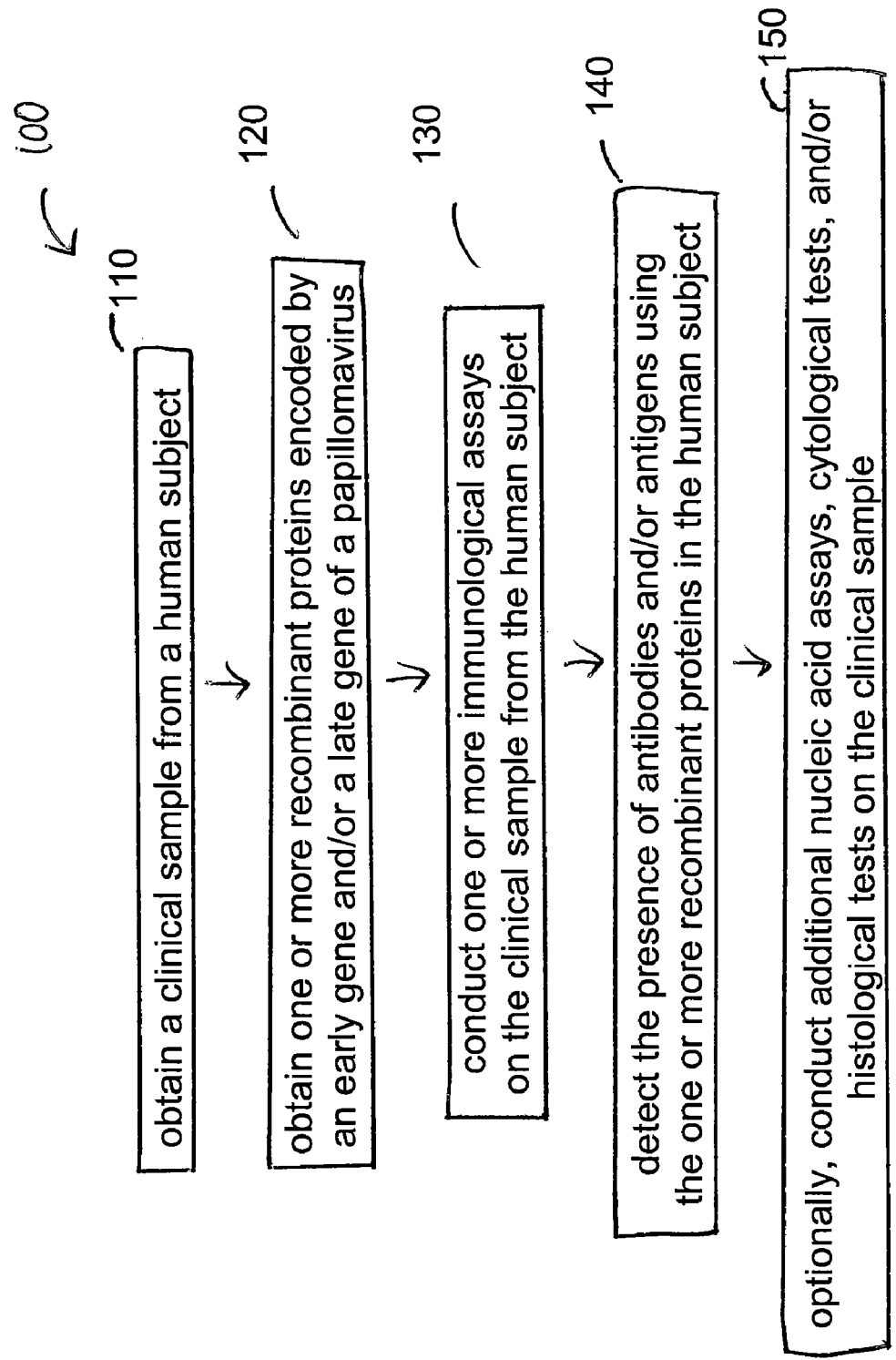
FIG. 1 illustrates an example of a method according to one or more embodiments of the invention.

FIG. 1 illustrates a method 100 of screening a human subject of papillomavirus infection. At step 110, a clinical sample from a human subject is obtained. The clinical sample may include, but are not limited to, genital swabs, general fluid, cervical cells, cervical tissues, cervical swabs, body fluids, serum, blood, urine, lesion sites, and tumors, among others. The clinical sample may be obtained by various methods known in the art. For example, genital swabs from clinical hospitals can be provided, together with pap smear scores, cytological results, and demographic history of the clinical samples from human subjects, either normal subjects or patients.

At step 120, one or more recombinant proteins encoded by an early gene and/or a late gene of a papillomavirus are obtained. The human papillomavirus may be, for example, high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, etc. High risk human papillomaviruses include, but not limited to, HPV-16, HPV-18, HPV-31, HPV-33, HPV-35, HPV-39, HPV-45, HPV-51, HPV-52, HPV-56, HPV-58, HPV-59, and HPV-68, among others. Low risk human papillomaviruses include, but not limited to, HPV-6, HPV-11, HPV-42, HPV-43, HPV-44, HPV-53, HPV-54, HPV-55, and HPV-56, among others.

Papillomaviruses are DNA viruses with a DNA genome, a non-enveloped viron, and an icosahedral capsid. The double-stranded, circular HPV DNA genome contains one coding region for late genes, one coding region for early genes, and a non-coding upstream regulatory region with binding sites for the various transcription factors controlling expression of early and late genes. Two separate open reading frames in the late gene coding region encode viral capsid proteins L1 and L2. Capsid protein L1 is the major capsid protein that is highly conserved among different HPV types. Eight open reading frames in the early gene coding region, encode eight viral early proteins, designated E1, E2, E3, E4, E5, E6, E7, and E8. Early proteins E6 and E7 are oncoproteins critical for host cell immortalization and transformation as well as for long term viral replication and survival.

Infection by high risk HPVs requires two early viral proteins, E6 and E7, which are oncoproteins because they transform cells in vitro and their presence is needed to maintain malignancy. Inhibition of E6 and E7 expression in precancerous or cancer cervical tissue blocks invasive cancer progression. Inside host tissues, E6 and E7 oncoproteins work by negatively blocking the activities of endogenous host cellular regulatory proteins, p53 and retinoblastoma (Rb) tumor suppression proteins, respectively, to cause inhibition of apoptosis and deregulation of cell cycle, leading to development of cervical cancers. E6 oncoprotein binds to p53, a cellular factor that protects against DNA damage and regulates apoptosis, to induce degradation of p53. By reducing the levels of p53 protein, E6 oncoprotein prevents tumor cell death. E7 oncoprotein binds to Rb to induce degradation of Rb, disrupt normal cell cycle, and cause cellular proliferation. The E7 oncoprotein further destabilizes cell control through its interaction with the cyclin-dependent kinase inhibitor protein, p21. HPV E6 and E7 oncoproteins are found to be continuously produced in transformed genital tissues. These interactions set the stage for controlling host cell proliferation and differentiation (i.e., transformation), a first step in the conversion of normal cells to pre-neoplastic cells and ultimately to the full expression of cancer malignancy.

One additional event that appears to play a role in tumor progression is integration of HPV DNA into host genome, which frequently disrupts the open reading frame for E2, resulting in over-expression of the E6 and E7 oncoproteins and possibly causing instability of host genome. Additional cofactors and mutational events may be important in the pathogenesis of invasive cervical cancers and may include chromosomal rearrangements, loss of constitutional heterozygosity, and proto-oncogene activation.

Both HPV-16 and HPV-18 are shown to immortalize human keratinocytes in culture and are by far the most common high risk HPV types that induce invasive cervical cancer. Infection by HPV-16 type alone is associated with over 50% of cervical cancer cases, mostly resulting in squamous cell carcinoma. HPV-18 infection is more likely to induce adenocarciomas. Some studies have indicated that adenocarcinomas in cervical tissues produce more aggressive forms of cancer with a less favorable outcome than cancers resulting from squamous cell carcinomas. This suggests that individuals with HPV-18 infection may have a much poorer prognosis than those with any other form of HPV infection.

To test the hypothesis that E6 and E7 play an active role in the maintenance of the malignant phenotype and may be ideal targets for anti-gene therapy, studies showed antiproliferative effects of phosphorothioate oligodeoxynucleotides (oligos) targeting HPV-16 E6 and E7 in cervical cancer cell lines and primary tumor explants. These specific antiproliferative effects suggest that HPV-16 E6 and E7 sequences play an active role in the malignant growth properties of cervical cancer cells and may be ideal targets for anti-gene therapy. Expression of two viral oncogenes, E6 and E7, in epithelial stem cells is required to initiate and maintain cervical carcinogenesis and results in significant over-expression of the cellular p16INK4a protein.

Variants of HPV-16 have also been found to produce differences in the aggressiveness of the forms of cervical cancer they induce. For example, Asian-American HPV-16 variants are more oncogenic than European HPV-16 variants. It has also been shown that Asian-American and African HPV-16 variants are more likely to produce invasive cervical cancer than European HPV-16 variants. The more aggressive nature of some of these variants may be related to variations in the amino acid sequences of the oncoproteins produced by the viruses. E6 protein from Asian-American HPV-16 variants are shown to be stronger in transforming keratinocytes and in suppressing p53 expression than E6 protein from European HPV-16 variants and these E6 proteins differ only in several amino acids in their sequences. Thus, in diagnosing high risk patients for invasive cervical cancer progression, it is important to identify not only the specific HPV type infecting the patient, but also the variant type of the infecting HPV.

In one embodiment, the early gene that can be used herein may include papillomavirus E6 genes, papillomavirus E7 genes, among others. In another embodiment, the late gene that can be used herein may include papillomavirus L1 genes, papillomavirus L2 genes, among others.

One aspect of the invention provides recombinant proteins, such as a recombinant hybrid protein containing a full length sequence of HPV oncogenic proteins, e.g., full-length E6, E7, and/or L1 polypeptide sequence, which have been found very difficult to obtain and purify due to undesirable aggregation during protein purification, protein instability, low levels of expression, low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus unsuitable as commercialized diagnostic tools.

The one or more recombinant proteins as described herein can be expressed in various suitable systems, such as bacterial expression systems, viral expression systems, yeast expression systems, mammalian expression systems, e.g., in *E Coli*, yeast, baculovirus, and/or mammalian cell cultures, generally known in the field. Although the polypeptides could be obtained by other means, embodiments of the invention provide one or more recombinant proteins mostly in (or close to) their native forms, which may be a much desirable conformation for binding with antibodies from tissues of human subjects with HPV infection in an immunological assay.

At step 130, one or more immunological assays are conducted on the clinical sample from the human subject. The one or more immunological assays as developed herein lend themselves to the high quality and properly purified recombinant proteins encoded by HPV early and late genes, resulting in immunological assays with very high sensitivity and specificity for screening HPV infection.

The one or more immunological assays include, but are not limited to, ELISA (enzyme linked immunoabsorbant assays), antigen assays for papillomavirus proteins, antibody assays for antibodies against papillomavirus proteins, assays for papillomavirus immunocomplexes, protein chip assays, radioimmunopercipitation assays, rapid membrane immunochromatographic assays, rapid stick immunochromatographic assays, among others. The one or more immunological assays may be non-invasive with minimal or no additional instrument required. The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989. and others books and manuals known in the art.

For example, the one or more immunological-based assays may include antibody-based assay having purified papillomarivus proteins coated on a surface, such as bottom surfaces of a microtiter plate, a membrane, and/or a chip. The surfaces that are not coated can be blocked with non-binding proteins. Then, a sample to be tested, such as a sample (samples from human subjects) likely with antibodies against HPV virus or HPV-associated proteins can bind to the surface by binding to the coated purified papillomarivus proteins. The bound antibody-purified papillomarivus protein complex can be detected by a secondary antibody and a number of commercially available detection systems using colormetric, chemilumenescent, or flourescent substrate. One example of secondary antibody is a horse radish peroxidase-conjugated secondary antibody, such as an antibody against-human immunoglobins (specific for IgG, IgA, etc.). The final results can be read by a microplate reader or visualized by eye if colormetric substrates are used.

As another example, an antigen assay involves coating of a primary antibody, such as a capture antibody having an affinity for binding to an antigen of interest, on a surface, such as bottom surfaces of a microtiter plate, a membrane, a chip, etc. The antigen of interest may be, for example, a papillomarivus protein, an oncoprotein, a capsid protein, which may be encoded by a HPV viral gene, e.g., an early gene or a late gene, etc. After blocking unbound portions on the surface, the clinical sample to be analyzed can be applied to bind with the capture antibody to form an immunocomplex, which can be detected by another primary antibody or a detection antibody by binding to the antigen of interest. Hence, the two primary antibodies or the pair of the capture antibody and the detection antibody interact with the antigen of interest, much like a sandwich. The capture antibody can be the same or different antibody as the detection antibody as long as the two antibodies can specifically bind to the antigen of interest, e.g., a HPV viral protein, a HPV oncoprotein, a capsid protein, among others.

Next, the sandwiched bound antibody-antigen complex can be detected by a secondary antibody, which have an affinity for the detection antibody and facilitate measurement by a standard immunological complex detection system using colormetric, chemilumenescent, flourescent and many different kinds of substrates. The final readouts or visualizations can be performed by an instrument with appropriate light absorbance readers or directly visualized by eye and compared the results to a control sample. Positive results indicate binding of the antigen of the interest to the primary antibodies, the capture antibody, and the detection antibody, and thus the presence of the antigen of interest in the clinical sample. In the contrary, negative results indicate no binding of the antigen of the interest to the primary antibodies and thus the absence of the antigen of interest in the clinical sample.

The one or more immunological assays can be used to detect at least three kinds of target proteins of interest, including, but not limited to, antigen, antibody, and antigen/antibody immunocomplex (also referred hereafter as antigen tests, antibody tests, and antigen/antibody immunocomplex tests, respectively), among others.

The formats of the one or more immunological assays may be a microplate format (e.g., 32 wells, 48 wells or 96 wells), a vertical or lateral membrane-based rapid test, a protein chip with multiple spot or multiplexed. The principles of the assays are the same as described above except detection systems vary depending on the substrate chosen for analyzing the results in different readouts or forms by an instrument specific designed for the assays. In addition, the procedures, conditions, binding specificity, developed in one type of immunological assay in one format can be adapted into a different format of the same or a different immunological assay, and/or a different immunological assay in the same or a different forma.

For example, in a protein chip assay, the surface for proteins to be coated/bound to may be, for example, a surface-chemistry treated glass or membrane, which can be covalently or non-covalently bind or coat with capture agents or proteins thereto. A spotting machine with fine pins dipped with capture agents, such as the recombinant proteins, antigens, antibodies, or other proteins, in suitable buffers is generally used to facilitate binding of such proteins or antibodies to the treated surface. Like other surfaces described in the microtiter plate format, the spotted and thus captured proteins or antibodies bind strongly to the surface-chemistry treated surface of a protein chip and remain on the treated surface to allow the interaction and specific binding of the captures proteins with target proteins, antibodies, or antigens, even after several washings of removing non-specific binding, to be detected with a detection system having a secondary antibody conjugated with Cy3 or Cy5. The detection of specific interaction is obtained and measured by the intensities of the spotted/dipped images via a microarray scanner.

More than one protein can be initially spotted and thus bound on the treated surface to specifically capture target proteins, antibodies, or antigens, and thus, it is possible to interact with and bind to multiple proteins or targets (multiplexed) in a single sample and binding of at least one of the multiple proteins or targets on the surface of the protein chip can be detected, performing one assay which is essentially many assays combined together. Thus, the protein chip assays, as compared to other assay formats, advantageously provides higher sensitivity and multiplex format with only very minimal amount of samples required, such as less than 50 μl or less than 10 μl. Such feature of being able to detect multiple binding activities with minimal sample requirement make it feasible to conduct many assays in one for certain disease tissues where the amount of accessible samples are very limited.

As another example, for a rapid immunological test, the surface for an antibody or a protein to be coated thereon can be membrane-based, and the binding capacity of the rapid immunological test differs, depending on the types of target proteins, antibodies, or antigens and background non-specific protein contained in the samples with the target protein, antibodies, or antigens. At least two formats of the rapid immunological test can be used, a vertical the rapid immunological test and a lateral the rapid immunological test.

The vertical the rapid immunological test is conducted in a device having a membrane as a capturing/binding surface for coating or spotting a capture agent thereon. The device further contains a pad underneath the membrane to allow the samples and assay reagent to flow through the membrane. Any target proteins, antibodies, or antigens that contained in the samples and specifically interact and bind to the capture agent will not flow through and will be captured and retain on the surface of the membrane, even after several washings to remove non-specific binding. A secondary antibody conjugate with HRP or others can be applied on the surface for detecting any protein-antibody complexes retained on the surface and being visualized by colormetric substrates.

The lateral rapid immunological test is a one-step test using a membrane strip with the capture proteins or antibodies already applied/coated to designated positions on the surface thereof. The only step the test requires is to combine obtained samples having the target proteins or antibodies with a detecting antibody conjugated with collateral gold particles and directly apply the combined mixtures to the membrane strip for the sample fluid to laterally flow through the membrane strip until the designated positions of the surface of the membrane strip. The capture-target-detecting protein-antibody immuno-complexes can be formed and retained on the designated positions where the capture proteins or antibodies are coated. Positive results can be visualized at these designated positions and no washing or separation is required, thus called one-step. The whole procedure for the test takes only minutes, for example, less than 15 minutes, and thus the test is also referred to as an one-step rapid test.

At step 140, the presence of antibodies and/or antigens against the one or more recombinant proteins in the human subject can be detected. Binding of any antibodies in the biological sample to the one or more recombinant proteins, binding of any HPV-associated proteins/antigens in a biological sample to antibodies obtained herein using the one or more recombinant proteins, and/or binding of any immuno-complexes of HPV-associated proteins in the sample to the one or more recombinant proteins and antibodies as obtained herein, indicates the presence of HPV infection protein in the sample.

The one or more immunological assays using the purified recombinants proteins derived from HPV early and/or late genes and antibodies as obtained herein serve as reliable indicators whether HPV infection has occurred. In addition, HPV associated malignancy or pre-malignant cell transformation can be assayed. One of the most useful aspects of the invention is in diagnosing cervical carcinoma, both squamous cell and adenocarcinoma as well as any epithelial cell abnormality associated with oncogenic HPV infection including koilocytosis; hyperkerotosis; precancerous conditions encompassing intraepithelial neoplasias or intraepithelial lesion; high-grade dysplasias; and invasive or malignant cancers.

The E6 and E7 oncoproteins encoded by early E6 and E7 genes are constitutively expressed in tumor cells, and silencing these genes yields reversion of the malignant phenotype. Thus, the early E6 and E7 gene products seem tumor-specific antigens, and possible targets or probes for screening these proteins/antigens or their antibodies thereof in immunological screening assay. These oncoproteins can also be targets for developing vaccines for immunotherapy to control HPV induced tumors.

For example, antibodies to the E6 and/or E7 oncoproteins have been found in those with HPV associated neoplasms. The E6 and E7 oncoproteins appear to be natural targets for antibody production due to their consistent expression in cervical cancer cells. It has been found that IgG and IgA against HPV-16 E6 and E7 oncoproteins are strongly disease associated. Antibodies against the E6 and E7 oncoproteins are at high levels in sera from cervical cancer patients as compared against non-cancer controls. Moreover, such antibodies can be detectable by immunological means even when present in lesser amounts.

Antibody tests and antigen tests for detecting antibodies against proteins encoded by early genes (e.g., E6 and E7) and late genes (e.g., L1) are performed. As an example, for detecting the presence of E6, E7, or L1 antibodies in human subjects, the concentrations of recombinant proteins, E6, E7, L1, respectively, needed to detect an anti-E6 antibody are optimized in a microtiter plate immunological assay format. Optimal reaction times, assay sensitivity and variability and conditions needed to semi-quantify the levels of E6, E7, or L1 antibodies are found and assay sensitivity and specificity can be calculated. In one embodiment, the sensitivity of the one or more immunological antibody test assays as described herein is in the range of micrograms, such as in the range of nanograms, or even picograms, etc. The specificity of the one or more immunological antibody test assays as described herein is in the range of about 50% or higher, such as about 70% or higher, about 85% or higher, about 90% or higher, about 95% or higher, or about 99% or higher.

As another example, for detecting the presence of E6, E7, or L1 antigens in human subjects, polyclonal and monoclonal antibodies against E6, E7, or L1 using the recombinant E6, E7, or L1 proteins are generated and the formation of immunocomplexes due to the binding between them are validated. Optimal reaction times, assay sensitivity and variability and conditions needed to semi-quantify the levels of E6, E7, or L1 antibodies, respectively, are found and the sensitivity and specificity for the assays can calculated. In one embodiment, the sensitivity of the one or more immunological antigen assays as described herein is between the range of micrograms, such as in the range of nanograms, or even picograms, etc. The specificity of the one or more immunological antigen test assays as described herein is in the range of aout 50% or higher, such as about 70% or higher, about 85% or higher, about 90% or higher, about 95% or higher, or about 99% or higher.

According to one or more aspects of the invention, the immunological assays for detection of HPV proteins, such as E6, E7, L1, etc., or immune response thereof due to HPV infection can be performed in high throughput ELISA screening assays, one step rapid immunological screening assays, and multiplexed protein chip assays, etc., and combinations thereof. Embodiments of the invention provides one or more assays, including an antibody, antigen, or immunocomplex assays developed to detect HPV viral proteins encoded by early genes (e.g., E6 and E7) and late genes (e.g., L1). In addition, the developed antibody, antigen, or immunocomplex assays for E6, E7, L1, protein or their antibodies thereof in one format, for example, a microplate format, can be adapted into a one-step immunochromatographic assay for the direct measurement of E6, E7, L1 proteins or antibodies induced by HPV infection.

The one-step immunochromatographic assay is a simple, fast, and easy to operate assay, which can be conveniently developed for point-of-care use. In general, there is simply mixing of a sample to be tested with a detection antibody as developed herein, the mixture can be applied onto or is already fixed on a surface (e.g., a membrane or a glass) for a pre-determined reaction time (e.g., in minutes, etc.) at optimized incubation temperature, such as at room temperature. The reaction can be optimized to be short for convenience depending on the quality of the detection antibody used and the assay reaction conditions. Thus, a rapid immunological test with short waiting time period can be performed and the assay results is generally designed to be visually scored without the need of any detection instruments.

As another example, protein chip immunological assays for detecting HPV proteins, such as E6, E7, L1, etc., or antibodies thereof can be performed for rapid detection of HPV infection. In addition, protein chip immunological assays can be designed to be multiplexed for detecting different protein or antibodies targets as well as in high throughput. The protein chip immunological assays as provided herein can be used for diagnosing HPV infection and for rapid detection of certain cervical cancer biomarkers. In general, a surface of a chip is initially covalently bound to antibodies, proteins, or antigens, which have an affinity to bind the target protein of interest in a sample, by using standard surface chemistries.

For example, purified recombinant E6, E7, and L1 proteins are shown herein to be able to attach to surfaces of a chip and selectively detect E6, E7, and L1 antisera in solution. As such, protein chip immunological assays are developed to provide a rapid readout of the presence of antibodies induced by HPV infection in a sample. Similarly, protein chip immunological assays are developed to provide a rapid readout of the presence of viral proteins in a sample due to HPV infection by attaching antisera or antibodies against HPV viral proteins encoded by early genes and/or late genes, e.g., L1, E6 and E7, etc.

As another example, to diagnose HPV infection using protein chip immunological assays, a capture agent, can be attached individually to various positions on the surface of one or more protein chips. Alternatively, the capture agent can be attached to different positions and thus in multiplexed format to detect different HPV infection related proteins simultaneously in one sample. The protein chip array of proteins or antibody from all HPV types, strains, or variants can be generated and used to screen phenotypes of HPV infection. Thus, the use of protein chip assays can be a very powerful screening tool to enable the design of one protein chip or test/assay suitable for executing many or all related immunological assays for screening or diagnosing HPV infection. The capture agent in a protein chip assay includes, but is not limited to, recombinant HPV viral proteins encoded by HPV early genes and late genes, recombinant E6, E7, and L1 proteins, antisera or antibodies against HPV viral proteins, encoded by early genes and/or late genes, e.g., L1, E6 and E7, etc. The assay conditions for the one or more protein chips are optimized/standardized and tested on clinical samples. The results from the ELISA immunological assays are also checked and correlated with the results of the protein chip immunological assays. The protein chip immunological assays may give better sensitivity over microplate immunological assays because of the use of laser as light source and better instrument designed for better detection limit. The higher assay sensitivity and better detection instrument enable the detection of detect extremely low amounts of antigens or antibody induce or developed in the body of those human subjects who are in the early stage of HPV infection or disease development to provide better prevention and disease management.

Positive results from the immunological assays confirm that the clinical sample may contain HPV associated proteins or antigens to indicate current HPV infection present in the clinical sample. It is also likely to detect past HPV infection still present in the clinical sample by detecting immune response of past or current HPV infection and/or the presence of antibodies induced recently or in the past due to HPV infection, etc. Further, the one or more immunological assays provided herein are suitable for general HPV infection as well as infection by high risk HPV types by using recombinant proteins derived from the genes of the HPV high risk types.

By obtaining the results of the immunological assays performed to detect antibodies or viral proteins derived from HPV early genes and late genes, concurring positive results further confirm HPV infection by conveniently obtaining one sample (more than one sample can also be used). It was found that concurring positive results from the one or more immunological assays performed herein correlate very well to the clinical status of the human subject where the clinical sample is obtained from. For example, concurring positive results are obtained and found in a large collection of clinical samples, to correlate well to the histological stages of cervical intraepithelial neoplasia (CIN), the stages or degrees/grades of the biopsy-confirmed squamous intraepithelial lesions (SIL), the stages of progression toward invasive cancer, carcinoma, and/or adenocarcinoma, the presence of cytological Atypical Glands of Undetermined Significance (AGUS), the presence of Atypical Squamous Cells of Undetermined Significance (ASCUS), etc.

Non-concurring positive results from the two assays for the proteins derived from HPV early genes and late genes may indicate general HPV infection, such as infection of different HPV types as well as cross reactivity with either one of the proteins in the two assays directed to early or late viral proteins. For example, it is found that there are positive results from cross reactivity to viral proteins derived from HPV early genes but negative results and no cross reactivity to viral proteins derived from HPV late genes, and vice versa.

At step 150, optionally, additional nucleic acid assays, cytological test and/or histological tests are conducted on the clinical sample. The nucleic acid hybridization assay conducted on the clinical sample to detect the presence of a papillomavirus genome in the clinical sample from the human subject may include polymerase chain reactions, nucleic acid hybridization assays, DNA chip assays, radioactive nucleic acid hybridization and detection assays, and non-radioactive nucleic acid hybridization and detection assays.

The method as described herein may also include performing a cytological papanicolaou smear assay on the clinical sample and comparing the results of the cytological papanicolaou smear assay with the results of the one or more immunological assays. Since HPV can't be cultured efficiently, and the clinical performance of serological assays is poor, diagnosis of HPV infection is almost entirely based on molecular tools. Nucleic acid amplification techniques such as PCR, nucleic acid-sequence based amplification, and advances in nucleic acid-based techniques, including hybrid capture technology (one example is a commercially available Digene hybrid capture II test from Digene Corporation, Gaithersburg, Md.), can be used in addition to the one or more immunological assays as described herein as a molecular screening tool for HPV infection.

In general, the hybrid capture II HPV DNA test is an in vitro nucleic acid hybridization assay used for detecting high-risk HPV types by employing RNA probes specific for thirteen high-risk types of HPV. The hybrid capture II HPV DNA test amplified the presence of RNA:DNA hybridized complex by coating the HPV specific DNA probes to a microtiter plate and a detection antibody (a monoclonal anti-DNA/RNA hybrid antibody) is used for detecting the amplified RNA:DNA complexes, followed by the addition of chemilumescent substrates to qualitatively detect the presence of the DNA of the thirteen high-risk HPV types in the sample.

Thus, it requires sophisticated equipments and trained personnel to perform the test and analyze the data using specific microplate reader and specific software developed for the reader. The applicability of the hybrid capture technology (Digene tests) was limited because complex execution of techniques requires sophisticated instrumentation and training and false positive and false negative on general population and early HPV infected individuals are very high, probably due to the requirements of the presence of DNA in the test sample which can be easily degraded or lost during sampling or sample-handling. However, the hybrid capture tests can be used to confirm the results of the one or more immunological assays as provided herein. Additional nucleic acid assays, cytological test and/or histological tests are known in the art can be used on the same clinical sample of the invention to further concur the results of the one or more immunological assays The one or more immunological assays as provided herein aims to employ user friendly procedures with simple instrument or no additional instrument to perform in a short period of time. Comparison of the results of the various immunological assays, nucleic acid hybridization assays with cytological and histological data for the human subjects as well as demographic information serve to validate the correlation and accuracy in diagnosing HPV infection and/or cervical cancer.

At present, there are no commercially available immunological assays to clinically measure the presence of HPV-associated proteins or antibodies. Embodiments of the invention thus provide a diagnostic tool useful for diagnosis of HPV infection and HPV related cervical cancer. In addition, the results from the immunological assays as described herein can be used to compare with other commercially available immunological assays specific designed for p53 and RB. It is known that infection high risk type HPVs, such as HPV-16 and HPV-18 may cause cervical cancer due o the expression of E6 and E7, the viral oncoproteins that induce cervical cell malignancy and alter/reduce the expression of p53 and RB endogenous proteins of the host cells, leading to cellular dysfunction and ultimately carcinoma. Thus, it is contemplated to compare the assays results on the levels of all of these proteins altered by HPV infection perform on clinical samples, e.g., cervical tissues, body fluids, serum, etc., from the same human subjects.

Changes in the expression levels of among these proteins affected by HPV infection (e.g., E6, E7, p53, Rb, among others) serve as a signature for high risk of contracting cervical cancer. Elevated levels of HPV-associated viral proteins or antigens and reduced levels of p53 and RB confirm the human subjects of not just HPV infection but also at high risk of contracting cervical cancer. On the contrary, unchanged levels of p53 and RB in the human subjects but elevated levels of HPV-associated viral proteins or antigens may indicate a general HPV infection and cervical cancer is not yet progressed.

Accordingly, one example of a method of screening a human subject of papillomavirus infection may include obtaining a clinical sample from the human subject, obtaining a first recombinant protein encoded by an early gene of a papillomavirus, obtaining a second recombinant protein encoded by an late gene of the papillomavirus; conducting one or more immunological assays on the clinical sample from the human subject, detecting the presence of an antibody to the first recombinant protein in the human subject using the first recombinant protein, and detecting the presence of an antibody to the second recombinant protein in the human subject using the second recombinant protein. The first recombinant protein may be, for example, recombinant HPV-16 E6 proteins, recombinant HPV-16 E7 proteins, recombinant HPV-18 E6 proteins, recombinant HPV-18 E7 proteins, etc. The second recombinant protein may be, for example, recombinant HPV-16 L1 proteins, recombinant HPV-18 L1 proteins, among others.

Another example of a method of screening a human subject infected with a human papillomavirus may include obtaining a clinical sample from the human subject, conducting a nucleic acid hybridization assay on the clinical sample, detecting the presence of a papillomavirus genome in the clinical sample from the human subject, conducting one or more immunological assays on the clinical sample, detecting the presence of an antibody to an early papillomavirus viral protein or the presence of the early papillomavirus viral protein in the clinical sample using a first recombinant protein of the early papillomavirus viral protein, and detecting the presence of an antibody to a late papillomavirus viral protein or the presence of the papillomavirus late viral protein in the clinical sample using a second recombinant protein of the late papillomavirus viral protein.

The early papillomavirus viral protein may include, but are not limited to, HPV-16 E6 proteins, HPV-16 E7 proteins, HPV-18 E6 proteins, HPV-18 E7 proteins, and others. The late papillomavirus viral protein may include, but are not limited to, HPV-16 L1 proteins, HPV-18 L1 proteins, and others. The presence of the papillomavirus genome can be detected, for example, using a nucleic acid probe with sequence homology to conservative DNA sequences from a papillomavirus gene, including papillomavirus late genes, L1 genes, L2 genes, papillomavirus early genes, E2 genes, E6 genes, and E7 genes, among others.

The one or more diagnostic immunological assays as described therein may include taking a sample of body fluid or tissue likely to contain antibodies against HPV associated proteins and/or HPV antigens, reacting it with one or more recombinant proteins as obtained and described herein, and assaying for the presence of any antibody-antigen complexes by suitable detection systems. Positive results confirm that the clinical sample may contain antibodies to indicate past HPV infection and concentrated levels of the antibodies in the present in the clinical sample. It is also likely to detect current HPV infection, indicating strong immune response of the human subject.

The one or more diagnostic immunological assays as described therein may also include obtaining polyclonal antibodies, monoclonal antibodies, and/or antiserum specific against the one or more recombinant proteins as obtained and described herein, taking a clinical sample likely to contain HPV associated proteins and/or antigens, reacting it with the obtained polyclonal antibodies, monoclonal antibodies, and/or antiserum specific for the one or more recombinant proteins, and assaying for the presence of any antibody-antigen complexes by suitable detection systems. Suitable detection system may employ various colormetric, chemilumenescent, flourescent substrates, etc., specific for a secondary antibody used in each immunological assay.

Still, another example of a method of screening a human subject of high risk human papillomavirus infection includes obtaining a clinical sample from the human subject, obtaining a first recombinant protein purified from a first protein expression system with a first expression vector having a portion of nucleic acid sequence corresponding to the full length nucleic acid sequence of an early papillomavirus gene and obtaining a second recombinant protein purified from a second protein expression system with a second expression vector having a portion of nucleic acid sequence corresponding to the full length nucleic acid sequence of a late papillomavirus gene. Then, one or more immunological assays can be conducted on the clinical sample to detect the presence of an antibody to a viral oncoprotein or the presence of the viral oncoprotein in the clinical sample using the first recombinant protein and the second recombinant protein. The first recombinant protein may be, for example, recombinant HPV-16 E6 proteins, recombinant HPV-16 E7 proteins, recombinant HPV-18 E6 proteins, and recombinant HPV-18 E7 proteins, etc. The second recombinant protein may be, for example, recombinant HPV-16 L1 proteins, and recombinant HPV-18 L1 proteins, etc. The early papillomavirus gene may be, for example, papillomavirus E6 genes and papillomavirus E7 genes, etc. The late papillomavirus gene may be, for example, papillomavirus L1 genes and papillomavirus L2 genes, etc. The early and late genes may be derived from high risk human papillomavirus, such as HPV-16 and HPV-18, etc.

Clinically applicable vaccination programs for cervical cancer may be available, as such, early detection to screen HPV positive and negative infected individuals is more than ever an urgent need to search for candidate subjects suitable of being vaccinated. Strategies to prevent cervical cancer may thus requires improved HPV testing/screening to cover a broad range of the worldwide population in addition to closely follow-up those subjects with past or present HPV infection and/or pre-cancerous lesions.

Screening/testing for past or present HPV infection along with a Pap smear can become the standard of care and the need is acknowledged in clinical guidelines developed by major medical groups including the American College of Obstetricians and Gynecologists (ACOG), the American Cancer Society (ACS), the Association of Reproductive Health Professionals (ARHP) and the American Society for Colposcopy and Cervical Pathology (ASCCP). Thus, the invention as described herein can be commercialized as a HPV general infection assay and/or a HPV high risk type infection assay and may play an important role as screening tests for cervical cancer. It is proposed that cervical cancer screening might become more efficient when it is based on combined cytology (results of par smear test) and high risk HPV infection screening. HPV infection screening tests may become necessary in addition to cervical cancer screening to serve as a early quick and easy screening, a quality control for false-negative smears, in triage of women with equivocal smears, in follow-up of women treated for CIN3 or cervical cancer and for the detection of cervical adenocarcinoma.

Early diagnosis of infection with high risk HPV types is important for successful prevention and treatment of cervical cancer, which is one of the more deadly forms of cancer. Importantly, it is known that infection in women for 12-15 years with HPV is required before invasive cancer to develop. It is thus important to be able to assay biomarkers of high risk HPV infection as described herein to pre-screen women early, such that it will be possible to treat HPV infection early and prevent cervical cancer development, rather than having to rely on chemotherapy or radiation to treat cancer malignancy. Developing the immunological assays as described herein to detect a series of biomarkers for general HPV infection in population as well as infection with high risk HPVs can be used for early diagnosis and therefore prevention of cervical cancer.

EXAMPLES

An object of the invention is to develop immune-responsive or antibody-reactive recombinant proteins derived from early genes and/or late genes of various HPV types and strains. It is a further object to provide these recombinant proteins in a chemically pure form. It is a still further object to provide simple, rapid, less expensive and more sensitive assays/tests for diagnosing not only HPV infection, but also most, if not all, HPV-associated neoplasm.

I. Cloning and Production of Recombinant Proteins Encoded by HPV Genes.

Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6:

GI:9627356; HPV51-E6: GI:9627155; HPV52-E6: GI:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Example 1

Cloning and Production of Various Recombinant Proteins Encoded by HPV-16 Early E6 Gene Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcac-caaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was subcloned into a histidine tag expression vector, pQE30, in order to express a his-tagged recombinant HPV-16 E6 protein. The resulting plasmid DNA is designated, pQE30/HPV16-E6 for the expression of His-tagged-HPV16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Other expression vectors which are used as recombinant protein expression systems with histidine tag (His$_6$, His$_8$, etc), glutathione-S-transferase (GST) fusion, maltose-binding-protein (MBP), among others, can also be used. in addition, the obtained HPV-16 E6 DNA fragment can be subcloned into other expression systems, including maltose-binding protein and glutathione-S-transferase-E6 fusion protein expression systems. Various expression systems can also be used to express E6 recombinant proteins from various HPV types and strains. For example, E6 recombinant protein from HPV-58 was obtained and designated as HPV-58-MBP-E6.

His tagged-HPV16-E6 and MBP-HPV-E6 recombinant proteins were expressed in *E. coli* BL21 (DE3) using IPTG driven induction. After two hour induction of protein expression at 37° C., GST-E6 or MBP-E6 recombinant proteins using standard protocols recommended by the suppliers (Amersham and New England Biolabs, respectively) were obtained and purified to a final concentration of about 1 mg/L. Longer induction time and re-flow though on protein purification column were found to generate higher protein yield, resulting in highly concentrated purified recombinant proteins at a yield of about 2-10 mg/L). The purity of the recombinant GST-E6 proteins was estimated to be >90% based on PAGE analysis. Recombinant E6 fusion proteins was used to detect the presence of E6 antibody on clinical samples and was also be used as immunogens for production of polyclonal antiserum and monoclonal antibodies.

Figure 2:
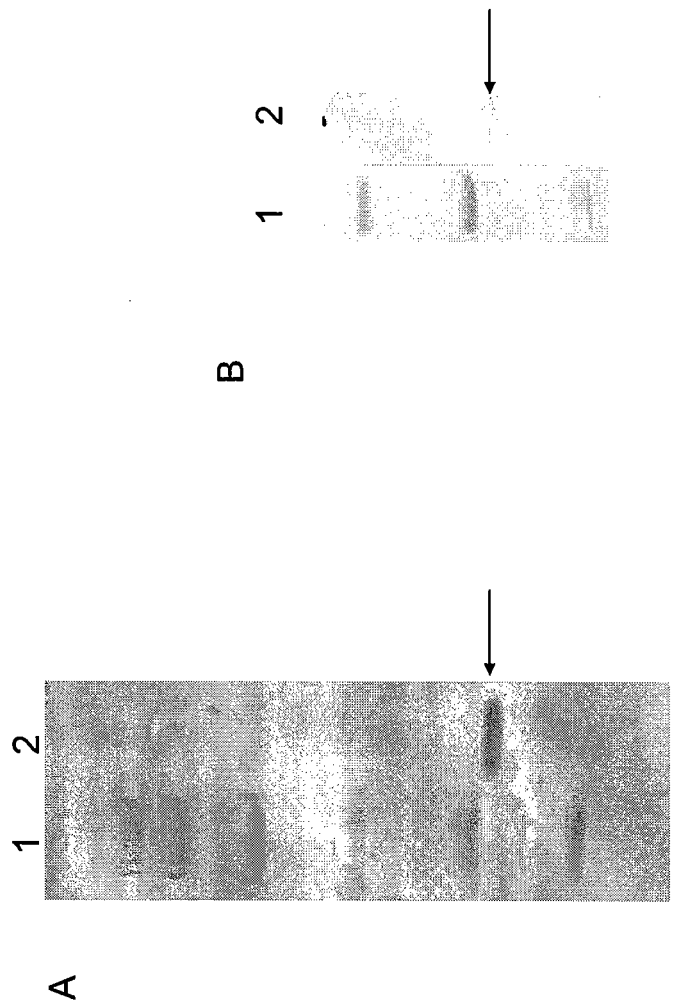
FIG. 2A demonstrates one embodiment of an exemplary purified recombinant protein encoded by an E6 early gene as visualized by SDS-PAGE by staining with commassie blue.
FIG. 2B demonstrates detection of a purified recombinant protein, HPV-16 E6 recombinant protein, by Western blot analyses according to one or more embodiments of the invention.
FIG. 2C demonstrates the result of gel filtration column chromatography of the purified recombinant E6 protein, demonstrating that the purified recombinant proteins HPV-16-E6 is a monomeric soluble protein. The purified recombinant E6 protein is eluted later than BSA.

FIGS. 2A and 2B demonstrate the expression of full-length HPV-16 E6 recombinant protein induced by IPTG analyzed by SDS-PAGE and western blot, respectively, using anti-E6 monoclonal antibody (MAb1-1). The molecular weight of the resulting His-tagged-HPV16-E6 recombinant protein is about 20.5 KD. The western blot was performed on a PVDF membrane using an anti-E6 monoclonal antibody, which is a mouse antibody, followed by a secondary antibody, an alkaline peroxidase (AP)-goat-anti-mouse IgG1, and visualized by the reaction of NBT and BCIP substrate mixture. The results showed that a single major protein band and thus pure recombinant E6 protein was purified. The purity of the recombinant E6 proteins was estimated to be about 90% or more based on PAGE analysis.

The purified recombinant E6 proteins as shown in FIG. 3A were used in one or more immunological assays, for example, to be used as a detecting antibody in antibody assays, etc. The purified recombinant E6 proteins were also used to as immunogens for generating antiserum, polyclonal antibody, and monoclonal antibodies specific against HPV-16 E6 protein.

Figure 2C:
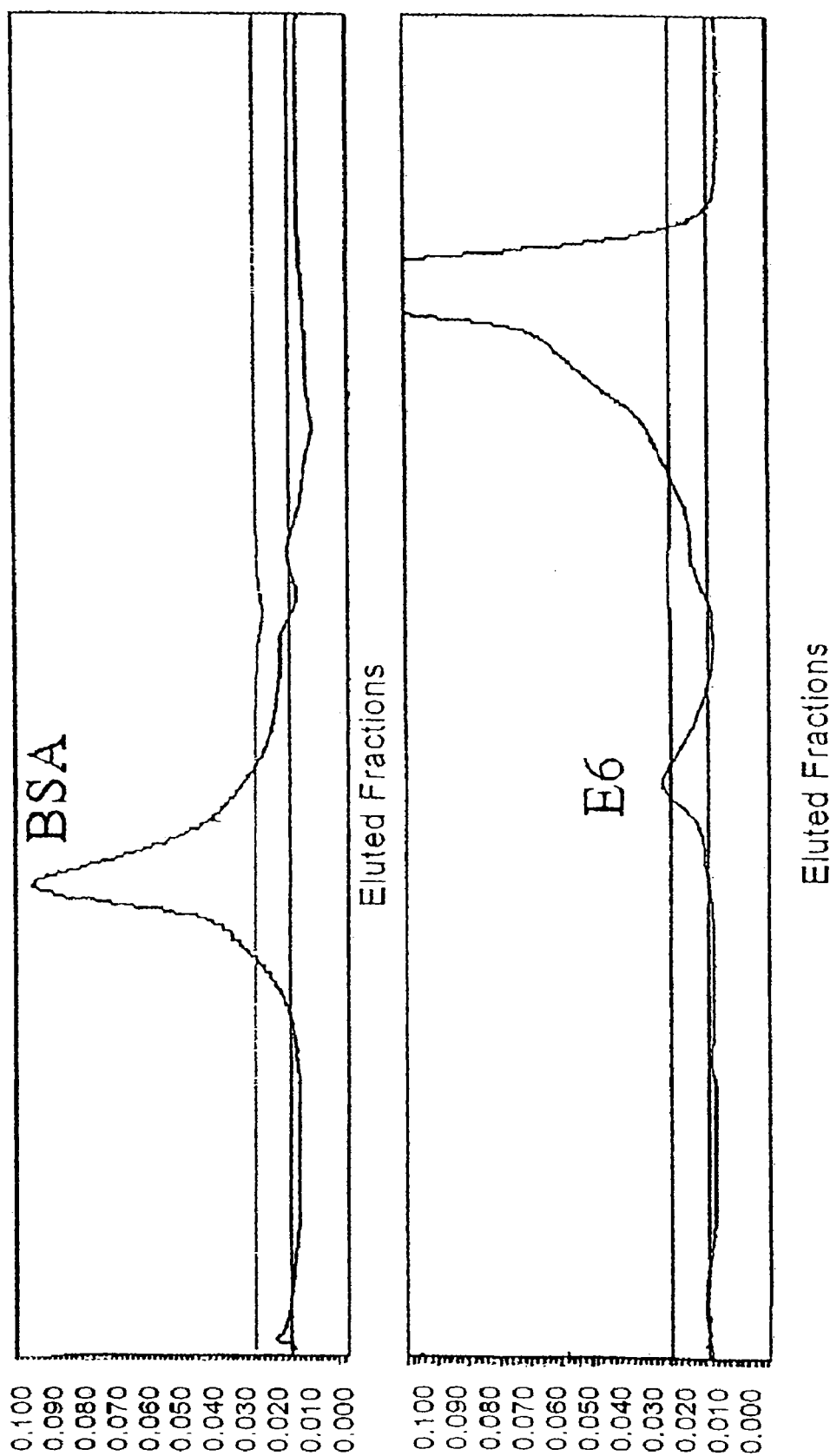

FIG. 2C demonstrates the result of gel filtration column chromatography of the purified recombinant E6 protein, demonstrating that the purified recombinant protein HPV-16-E6 is a monomeric soluble protein with molecular size about 20.5 kDa. The purified recombinant E6 protein is eluted later than BSA.

Example 2

Cloning and Production of Recombinant Proteins Encoded by HPV-16 Early E7 Gene

Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatg-gagatacacctacattgc 3' (SEQ ID NO. 9) and 5' ccgGAATTCt-tatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was subcloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

Figure 3:
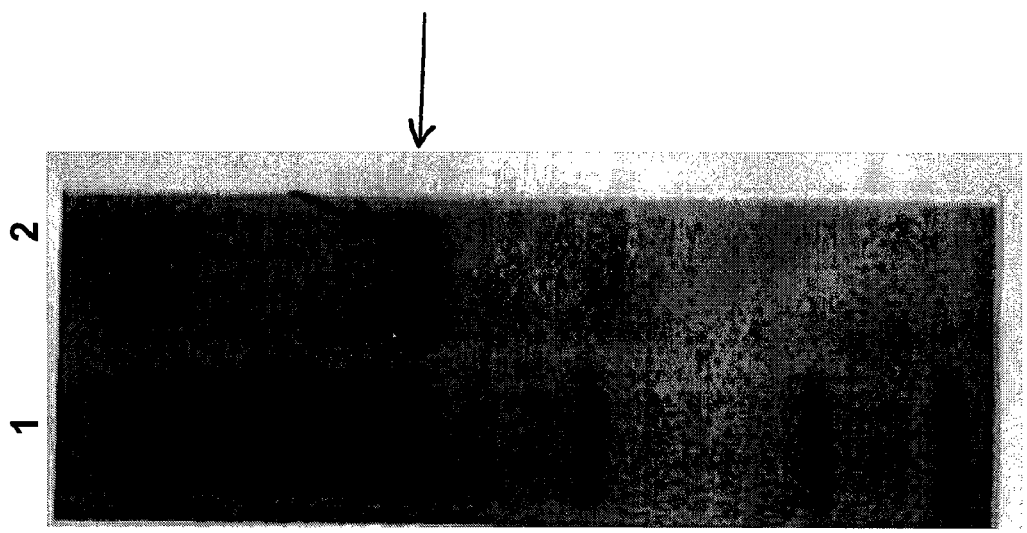
FIG. 3 is a SDS-PAGE gel, showing one exemplary purified recombinant HPV-16-E7 proteins according to one or more embodiments of the invention.

FIG. 3 is a SDS-PAGE gel, showing one exemplary purified recombinant HPV-16-E7 proteins. As shown in FIG. 3, the HPV-16-E7 recombinant proteins is purified to homogeneity as a major single band with a molecular weight of 37.2 KDa as indicated by an arrow.

Example 3

Cloning and Production of Recombinant Proteins Encoded by HPV-16 Late L1 Gene

Cloning of an exemplary late gene from an exemplary HPV type, HPV-16, is described herein. A 1596 base pair (b.p.) DNA fragment (SEQ ID NO. 13) containing the 531 amino acid coding region (SEQ ID NO. 14) of the HPV-16 L1 gene was obtained by polymerase chain reaction (PCR) amplification. Primers were used for PCR cloning, for example, a pair of forward and reverse primers, 5' ccgCTCGAGatgcaggtgactttatttacatcc 3' (SEQ ID NO. 15) and 5' cccAAGCTTttacagcttacgttttttgcgttta 3' (SEQ ID NO. 16), respectively. The DNA sequence of the isolated DNA fragment was confirmed by comparing with the sequence from Gene Bank database. In addition, L1 DNA fragments from different strains of HPV-16 can also be cloned from different clinical samples or sources.

The obtained 1596 base pair (b.p.) DNA fragment was sub-cloned into a baculovirus expression system in order to express a recombinant HPV-16 L1 protein. The DNA sequence and the amino acid sequences of the resulting recombinant HPV-16 L1 protein are shown as SEQ ID NO. 17 (a 1716 base pair (b.p.) DNA fragment) and SEQ ID NO. 18 (a 571 amino acid protein), respectively. The molecular weight of the resulting recombinant HPV-16 L1 protein is about 64.2 KD. The recombinant HPV-16 L1 proteins were obtained and purified to a final concentration of about 1 mg/L. Other expression systems can also be used to express L1 recombinant proteins from various HPV types and strains.

In general, recombinant proteins from various high risk HPV types and low risk HPV types or strains can be obtained by cloning of early and late genes by polymerase chain reaction (PCR) amplification using a pair of forward and reverse primers using procedures as described herein and in various recombinant protein expression systems. For example, a recombinant N-terminal fragment of HPV-16 L1 protein was also obtained by expression in His-tagged expression system. The amino acid sequence of the resulting recombinant HPV-16 L1N-His protein is shown as SEQ ID NO. 19 and the molecular weight of the HPV-16 L1N-terminal recombinant protein is about 34 KD. C-terminal fragments can also be obtained, Recombinant L1 proteins and/or recombinant L1 partial proteins were used to detect the presence of L1 antibody on clinical samples and were also be used as immunogens for production of polyclonal antiserum and monoclonal antibodies.

Figure 4:
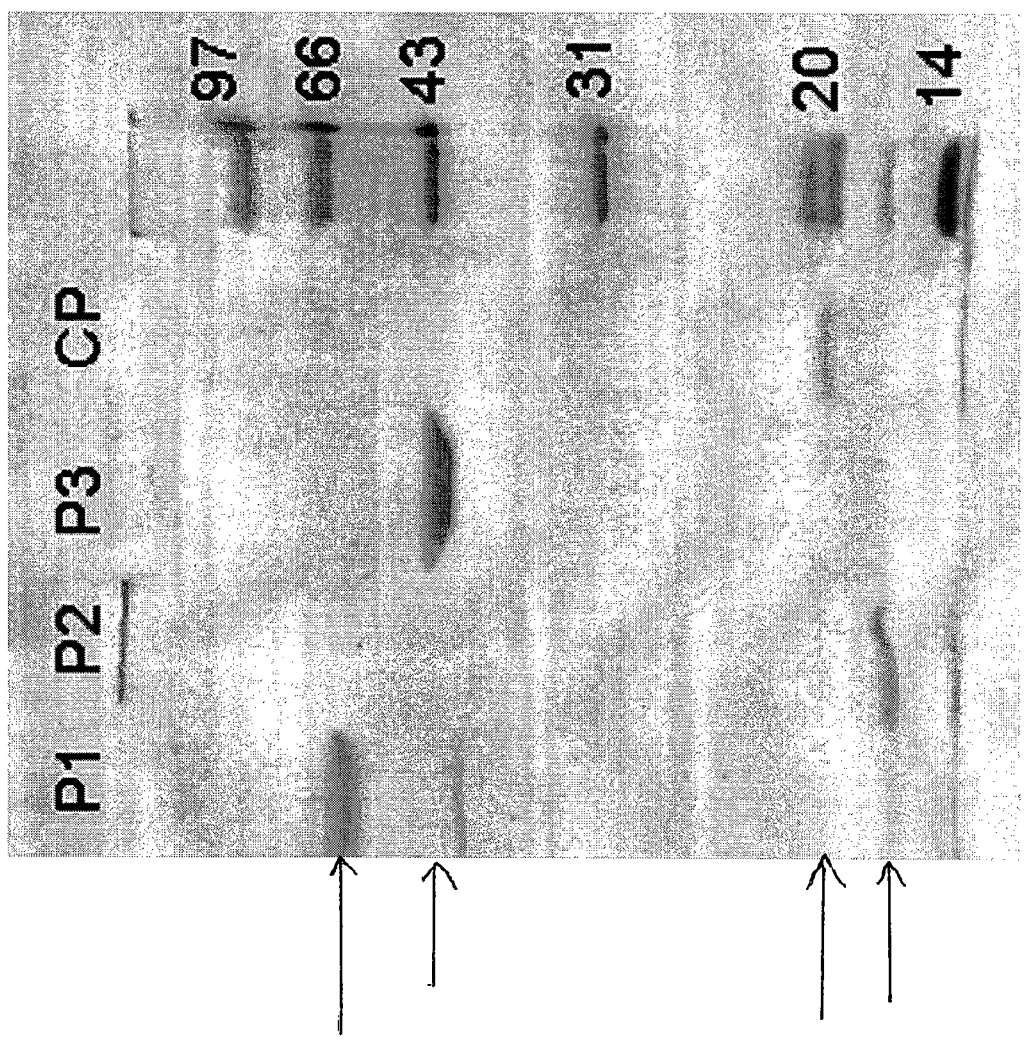
FIG. 4 demonstrates SDS-PAGE of three exemplary purified HPV early gene recombinant proteins by commassie blue staining according to one or more embodiments of the invention. P1: HPV-58-E6-MBP fusion protein; P3: MBP protein; P2: HPV-16-E7-His fusion protein; CP: HPV-16-E6-His fusion protein.

FIG. 4 demonstrates SDS-PAGE of three exemplary purified HPV recombinant proteins by commassie blue staining according to one or more embodiments of the invention. Recombinant fusion proteins were obtained for different HPV types, such as different high risk HPV types, e.g., HPV-16, HPV-18, HPV-58, etc. P1 indicates a purified recombinant HPV-58-E6-MBP fusion protein as compared to P3 for a MBP protein alone. P2 indicates a purified recombinant HPV-16-E7-His fusion protein and CP indicates a purified recombinant HPV-16-E6-His fusion protein.

II. Sample Collection

Biological samples to be analyzed using the methods of the invention may be obtained from any mammal, e.g., a human or a non-human animal model of HPV. In many embodiments, the biological sample is a clinical sample obtained from a living subject. In some embodiments, the subject from whom the sample is obtained is apparently healthy, where the analyses and/or assays are performed as a part of routine screening. In other embodiments, the subject is one who is susceptible to HPV, (e.g., as determined by family history; exposure to certain environmental factors; etc.). In other embodiments, the subject has symptoms of HPV (e.g., cervical warts, or the like). In other embodiments, the subject has been provisionally diagnosed as having HPV (e.g. as determined by other tests based on, e.g., pap smears, hybrids capture, PCR tests, etc.).

The biological sample may be derived from any cells, tissues, organs or group of cells of the subject. In some embodiments a cervical scrape, biopsy, or lavage is obtained from a subject. In other embodiments, the sample is a blood or urine sample. In some embodiments, the biological sample is processed, e.g., to remove certain components that may interfere with an assay or method of the invention, using methods that are standard in the art. In some embodiments, the biological sample is processed to enrich for proteins, e.g., by salt precipitation, and the like. In certain embodiments, the sample is processed in the presence proteasome inhibitor to inhibit degradation of antibodies, proteins, or antigens and the like.

Samples as used herein include to a material or mixture of materials, typically, although not necessarily, in fluid form, i.e., aqueous, containing one or more components of interest and may include any of the biological samples, clinical samples, etc. Samples may be derived from a variety of biological sample, liquid, or solid, such as tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

Example 4

Clinical Sample Collection Procedure

All samples were taken from female patients during their scheduled visits for gynecological examinations. After inserting a speculum to a human subject, a brush or a cotton swab was inserted in the endocervix and rotated to obtain endocervical cells. The brush or swab was then removed out to smear on a slide (pap smear). The brush or swab was then placed into about 1 ml of specimen dilution buffer (PBS+1% BSA) and vigorously shaken to remove bound material (mucus and cells). The diluted specimens are stored at a −20° or −80° C. freezer.

Venous blood was obtained by usual phlebotomy methods, with a 21- or 22-gauge double-pointed needle into a agar barrier tube for a total of 7-9 ml from each subject. The blood was allowed about 15 minutes at room temperature for clot formation and was centrifuged for 15 minutes. Serum was aspirated away from blood cells, using a disposable pipette, dispensed into Eppendorf tubes as aliquots, and stored at a −20° or −80° C. freezer. As a negative control with no HPV infection, serum can be obtained from virgin females.

III. Nucleic Acid Hybridization Assays for Screening of HPV Infection

Nucleic acid hybridization assays can be used in addition to the immunological assays provided herein.

Example 5

Isolation of DNA from Samples

To prepare DNA for nucleic acid hybridization assays, the sample of a cell suspension was vigorously shaken, and 120 µl was treated by adding 40 µl of proteinase K (200 µg/ml) in 3% Triton X-100 for 1 hour at 37° C. The proteinase was inactivated by incubation at 95° C. for 10 minutes. Subsequently, 10 µl of the solution was used in a reaction.

Example 6

Detecting the Presence of HPV Genome using PCR Analyses

Primers are designed to detect the presences of HPV early genes and late genes for various HPV types. For example, DNA forward and reverse primers (SEQ ID NO. 20 and SEQ ID NO. 21; 5'-GCNCARGGHCAYAAYAATGG-3' and 5'-GTDGTATCHACMHCAGTAACAAA-3', respectively. N: A+T+C+G; R: A+G; H:A+C+T; Y:T+C; D: T+A+G; M: A+C) can be used to detect various L1 genes from different HPV types due to the conserved sequence homology of these genes. The primers used herein are located in the L1 open reading frame. The presence of L1 gene can be used to detect various HPV-16 types due to sequence homology of various HPV L1 proteins.

About 20 pmols of forward and reverse primers and about 1 µl of isolated DNA, 10 mmol/L, from a test sample were mixed to a final reaction volume of about 10 µl, containing Tris-HCl, pH 9.0, 50 mmol/L KCl, 2.5 mmol/L $MgCl_2$, 0.1% Triton X-100, 0.01% gelatin, 200 mmol/L of each deoxynucleoside triphosphate, and 0.25 U of SuperTaq (Sphaero Q, Cambridge, UK). PCR reaction conditions were as follows: preheating for about 1 minute at about 94° C., followed by 40 cycles of about 1 minute at about 94° C., about 1 minute at about 45° C., and about 1 minute at about 72° C., and a final extension of about 5 minutes at about 72° C. The PCR products were analyzed by 3% agarose gel electrophoresis. A synthetic positive control (65 mer, SEQ ID NO. 22) for the presence of L1 gene was also synthesized and used in PCR nucleic acid assays.

As another example, designed DNA forward primers (SEQ ID NO. 23 and SEQ ID NO. 24) and reverse primers (SEQ ID NO. 25) can be used to detect the presence of HPV-16 by analyzing the presence of E6-containing DNA fragments, including a 181 b.p. E6 DNA fragment and a 286 b.p. E6 DNA fragment (SEQ ID NO. 26 and SEQ ID NO. 27, respectively). Additional DNA forward and reverse primers were also designed to detect E7 genes.

Example 7

Comparison with HPV DNA Hybrid Capture Assays

Hybrid Capture II HPV DNA Test from Digene Corporation were also performed on obtained clinical samples as a comparison. The hybrid capture II DNA test is approved by the U.S. Food and Drug Administration to test for oncogenic HPV DNA, as reflexive follow-up of an ASCUS (Atypical Squamous Cells of Undetermined Significance) or other abnormal Pap results. The test was run according to the manufacturer's protocol using the microtiter plate based format and probes for "high carcinogenic risk" HPV types at certified clinical laboratories. Samples readings of 1 fold or more than the positive control (1 pg/mL HPV DNA or 5000 HPV genome copies per test) were considered to contain DNA from a number of high risk HPV types.

The hybrid capture test involves a molecular hybridization that uses nonradioactive probes with amplification of the detection of the hybrid ones for chemoluminescence. The material for analysis is denatured and reacts with specific probes forming hybrid RNA/DNA that are captured by antibodies that cover the walls of the tube. Specific antibodies against RNA/DNA conjugated with alkaline phosphatase are reacted with the immobilized RNA/DNA hybrids. By forming a stable substrate complex for alkaline phossphatase, the RNA/DNA hybrids are capture by antibody and detected by chemoluminescence via spectrometry.

IV. Immunological Assays for Screening of HPV Infection

One of the initial reactions of a human subject to HPV infection is thought to be the generation of antibodies against the E6 and E7 oncoproteins. Presently, no immunological diagnostic assay is commercially available to detect this immune response. Because the amino acid sequences of various E6 and E7 proteins (see, Table 1) are different with various degree of amino acid sequence homology among different HPV types, host antibodies produced in response to the same early oncoprotein from one HPV type will be very different from another HPV type. For example, antibodies induced in a host against oncoproteins (e.g., E6, E7, etc.) from an oncogenic HPV type or strain (e.g., HPV-16, HPV18, etc.) can be significant different from antibodies induced by other proteins associated with other HPV types.

TABLE 1

| Amino acid sequence homology of L1, E6 and E7 for different HPV Types | | | |
|---|---|---|---|
| | L1 | E6 | E7 |
| HPV 16 v. HPV 18 | 63% | 53% | 42% |
| HPV 16 v. HPV 31 | 81% | 65% | 73% |
| HPV 16 v. HPV 33 | 79% | 62% | 60% |
| HPV 18 v. HPV 31 | 64% | 51% | 38% |
| HPV 18 v. HPV 33 | 65% | 46% | 44% |
| HPV 31 v. HPV 33 | 78% | 57% | 59% |
| HPV 16 v. HPV 6A | 68% | 35% | 56% |
| HPV 16 v. HPV 11 | 68% | 34% | 55% |
| HPV 6A v. HPV 11 | 92% | 81% | 83% |

It is proposed and tested herein that, detection of antibodies or antigens to oncoproteins encoded by early genes, such as E6 or E7 protein from HPV high risk types in serum, body fluid, or cervical tissues could be an indication whether the human subject is at high risk for cervical cancer development. In addition, detection of antibodies or antigens to viral proteins encoded by late genes, such as capsid proteins L1, L2 from HPV high risk types can be used together or independently in the same or different immunological diagnostic assays to further confirm the risk of the subject to develop cervical cancer.

Accordingly, embodiments of the invention also provide immunological assay systems to detect the presence of any HPV-associated proteins, oncoproteins, and/or capsid proteins directly in one or more immunological assays that can be performed concurrently or separately on an obtained clinical sample.

Example 8

Figure 5:
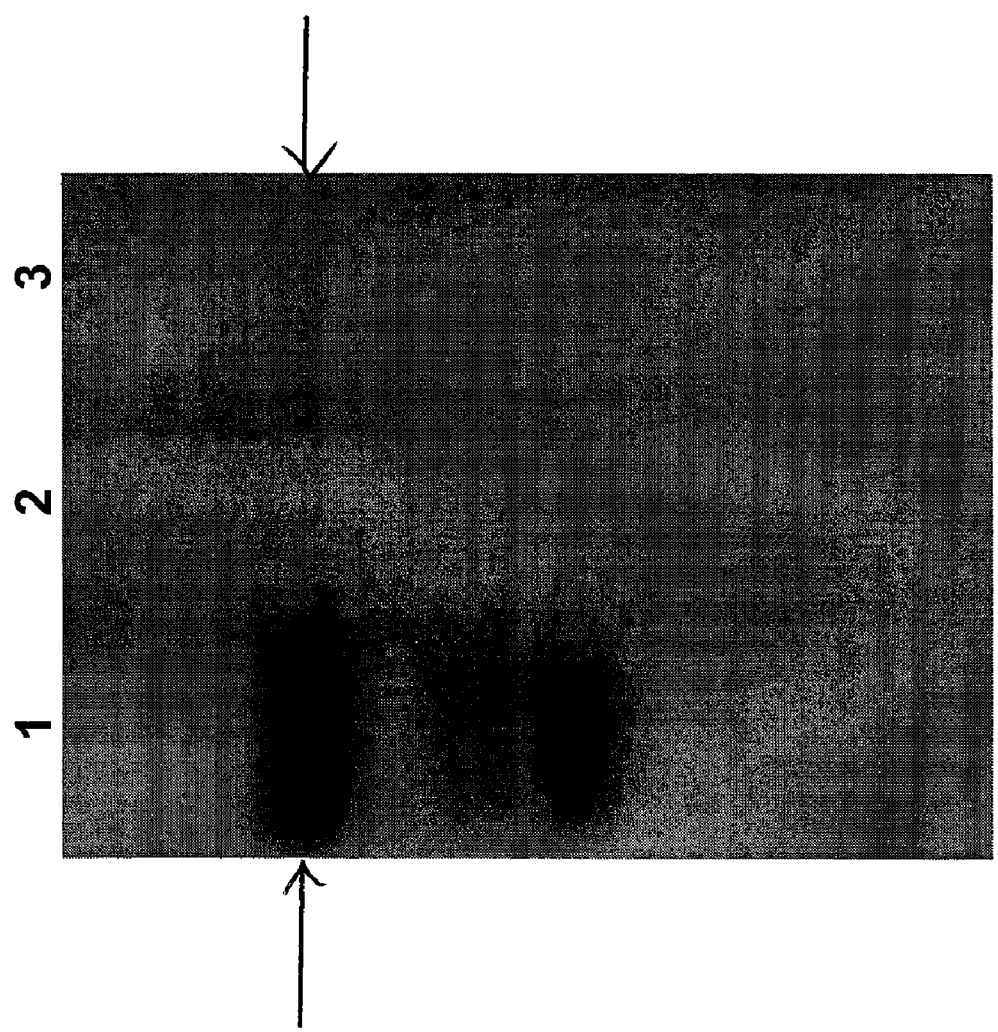
FIG. 5 demonstrates detection of three exemplary purified HPV early gene recombinant proteins with different antibody by Western blotting. Lane 1: HPV-16-E7-His with MAb2-1 (anti-HPV-16-E7 antibody); Lane 2: HPV-16-E7-His with MAb2-2 (anti-HPV-16E7 antibody); Lane 3: HPV-16-E7-His with MAb2-3 (anti-HPV-16-E7 antibody).

Western Blot Analyses for Detection of Purified Recombinant HPV Proteins Encoded by Early Genes FIG. 5 demonstrates the detection of three exemplary purified recombinant proteins encoded by HPV early genes using Western blot analysis. Lane 1 indicates the detection of recombinant proteins, HPV-16-E7-His, and thus binding of the recombinant proteins to a monoclonal antibody, anti-HPV-16-E7 antibody (MAb2-1). Lane 2 indicates the detection of recombinant proteins, HPV-16-E7-His, and thus binding of the recombinant proteins to a monoclonal antibody, anti-HPV16E7 antibody (MAb2-2). Lane 3 indicates the detection of recombinant proteins, HPV-16-E7-His, and thus binding of the recombinant proteins to a monoclonal antibody, anti-HPV-16-E7 antibody (MAb2-3).

Example 8

Figure 6:
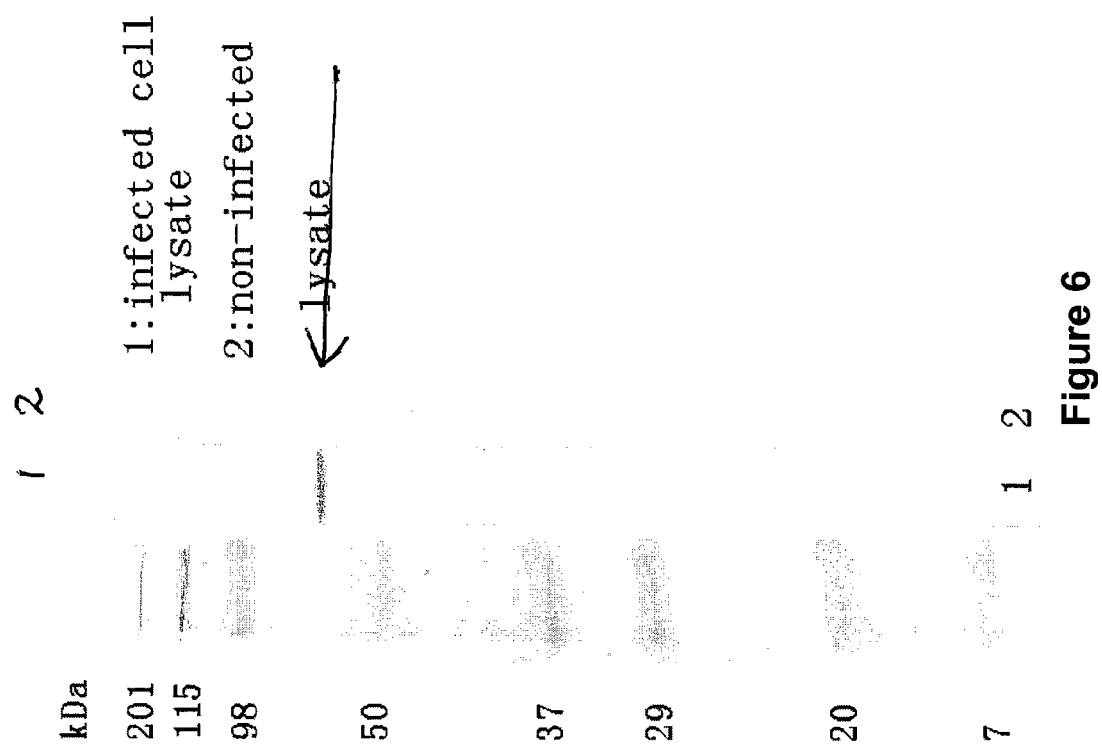
FIG. 6 demonstrates detection of an exemplary purified HPV late gene L1 recombinant protein by Western blotting using anti-his tag antibody and chemilluminescent substrates (visualized by the reaction of NBT and BCIP substrates) according to one or more embodiments of the invention.

Western Blot Analyses for Detection of HPV Associated Antigens and/or Proteins Encoded by Late Genes FIG. 6 demonstrates the detection of an exemplary purified recombinant protein encoded by HPV late genes using Western Blot analysis. Lane 1 is loaded with cell lysate from SF9 cells infected with HPV16 L1 recombinant baculovirus for 72 hrs. Lane 2 is loaded with cell lysate from SF9 cells infected with baculovirus without HPV16 L1 gene for 72 hrs. The single major band visualized by Western blotting using anti-his tag antibody and after the reaction of NBT and BCIP substrates indicates the full-length of recombinant L1 protein at a molecular weight of 64.2 kDa.

Example 9

Non-Radioactive Immunological Assays

Cell suspensions from collected samples were centrifuged, and the supernatant was used to run in the assays by diluting the supernatant 1:10 in specimen dilution buffer. Assays from this invention are non-invasive with little or without instruments. In general, embodiments of the invention provides in vitro enzyme immunological assays which are non-radioactive intended for direct detection of HPV associated proteins and/or antibodies as an indication of HPV infection. The assays as described herein are suitable as adjunct tests in addition to clinical physical examination, Pap smear tests, biopsys and other clinical tests.

An immunological assay can, for example, be performed in a variety of different ways. Detection of the antibodies that have bound to specific antigens can, for example, be achieved with various antibodies to antibodies (anti-antibodies) or other compounds with affinity for antibodies, such as protein A or protein G. These reagents can be labelled in many different ways, for example radioactively (radioimmunoassay), with fluorescein (fluoro-immunoassay), or enzymatically (enzyme-linked immunoassay, ELISA or EIA). A special case of enzymatic immunoassay is when the antigen-antibody complexes are detected on clinical samples or tissue sections. Such a procedure is instead referred to as immunostaining or immuno-histocytochemistry, although the underlying principle is the similar as for ELISA. In addition, the formats of the immunological assays can vary and may include a format in microplate (various number of wells), simple rapid tests, protein chips, and others.

In an alternate embodiment, the purified recombinant proteins can be used in similar immunological assays to detect the presence of antibodies raised against HPV immunotherapy in the serum, or other bodily fluid or tissues, such as those human subjects undergoing anti-HPV vaccine treatment. The detection of the positive results from the samples of a subject undergoing vaccine treatment using the assays as described herein and the purified recombinant proteins is beneficial, for example, can be used to titrate semi-quantitative the serum sample of the subject treated with an anti-HPV vaccine and adjust the dosage of the vaccines.

There are at least three types, but not limited to, of immunological assays depending the target proteins to be detected, including antigen tests, antibody tests, and antigen/antibody immunocomplex tests. For example, a method is provided to detect the presence of antibodies, immunoglobulins, etc., against HPV proteins, such as E6, E7, and/or L1, etc., in a sample from a human subject. The purified recombinant proteins as described herein can be used to detect antibodies against HPV E6, E7, and/or L1 proteins. The method generally includes contacting the purified recombinant proteins with the sample and detecting any binding of the purified recombinant proteins to the sample, wherein binding of the purified recombinant proteins to the sample indicates the presence of HPV-induced or HPV-associated antibodies in the sample and thus possible HPV infection for the subject in the past or current.

The antibodies present in the sample may be antibodies against E6, E7, L1, and other proteins from the same HPV types and strains as the purified recombinant proteins. Alternatively, cross reactivity of the binding of any antibodies in the sample to the purified recombinant proteins may result in the detection of the presence of antibodies from different HPV types or strains and thus indicate HPV infection of different types or strains. However, such cross reactivity need to be confirmed since sequence homology of some of the HPV proteins from different HPV types are low as shown in Table 1.

Similarly, method are provided to detect the presence of antigens, HPV-associated proteins, HPV-induced proteins, such as E6, E7, L1, L2, p53, and/or Rb, etc., in a sample from a human subject. The purified recombinant proteins as described herein can be used, for example, in a sandwiched assay to detect these target proteins or antigens. Alternatively, monoclonal antibody, polyclonal antibodies, and antiserum against the purified recombinant proteins can also be obtained and purified to be used in antigen tests, antibody tests, and antigen/antibody immunocomplex tests to indicate possible HPV infection in the past or current by the same or different types or strains for the subject.

Example 10

Immunological ELISA Antibody Test for Detection of HPV Associated Antibodies

In general, ELISA is performed according to standard procedures. For example, coating of purified recombinant proteins is performed in about 50 µl volume in a 96 well format at 4° C. overnight before blocking the bottoms of a microtiter plate with about 200 µl of a blocking buffer at room temperature for 2 hours. A sample that contains antiserum, monoclonal antibodies, polyclonal antibodies, and other targeted HPV-induced antibodies can be added to react with the recombinant proteins in about 50 μl volume at room temperature before washing with a wash buffer several times. A secondary antibody, anti-human or anti-mouse, etc., that can generically bind to the targeted antibody was used to react with antibodies or immunocomplex bound to the bottom of the microtiter plates. Substrate development is performed and read out in a microtiter plate reader to measure OD absorbance at 450 nm wavelength, $OD_{450}$. In a horseradish peroxidase immunoassay detection system, about 50 μl of 3,3',5,5' tetramethylbenzidine, a substrate for horseradish peroxidase can be added to each well of the microtiter plates and the reaction mixture is incubated at room temperature for about 5-30 minutes or until a visually obvious green-blue color developed before stopping the reaction mixture by adding about 50 μl of 1.5 M $H_2SO_4$ into each well.

An ELISA assay (see, e.g., Harlow and Lane (Antibodies: A Laboratory Manual Cold Spring Harbor Laboratory, Cold Spring Harbor, N.Y. (1989)) generally includes preparing proteins/antigens/antibodies, coating the well of a 96 well multiwell plate (microtiter plate) with the antigens/proteins/antibodies, adding proteins of interest or antibodies of interest or conjugated to a detectable compound such as an enzymatic substrate (e.g., horseradish peroxidase or alkaline phosphatase) to the wells and incubating for a period of time, and detecting the presence of the antigens/proteins/antibodies. In some cases, the antibody of interest does not have to be conjugated to a detectable compound; instead, a second antibody (which recognizes the antibody of interest) conjugated to a detectable compound may be added to the well. Also, instead of coating the well with the antigen, the antibody may be coated to the well. In this case, a second antibody conjugated to a detectable compound may be added following the addition of the antigen of interest to the coated well. One of skills in the art would be knowledgeable as to the parameters that can be modified to increase the signal detected as well as other variations of ELISAs known in the art.

An ELISA procedure can also be carried out in a variety of formats. Methods for enhancement of ELISA sensitivity using several layers of anti-antibodies, avidin-biotin complexes and enzyme-anti-enzyme antibody complexes are well known in the art. The solid support or surface for fixation of antigen is usually plastic, as described here, but a variety of other solid supports such as latex or agarose have been described. It is also not necessary for the antigen to be directly fixed onto the solid support/phase. There is for example a commonly used ELISA format that fixes the specific antigen to the solid support via a solid-phase-fixed antibody to the antigen, so-called catching antibody ELISA or sandwich ELISA. A special case of immunoassay which involves a blotting (transfer) of antigen to a solid support in sheet format is termed immunoblotting. Typically, the solid support is nitrocellulose or nylon membranes/sheets, but other supports have been described. Various binding, mixing, incubating, coating, or blotting interactions are involved in an ELISA assay. Prior to an ELISA assay, the antigens or antibodies can be separated according to their sizes by gel electrophoresis or similar methods. Detection of antibodies bound to the specific antigen on the sheet can be carried out in similar ways as for other immunoassays.

The 96 well format is a high throughput screening format useful to optimize assay procedures and conditions. Other format with different number of wells can also be used. Positive controls and negative controls were also performed on, for example, serum samples from donor subjects that are positive for HPV infection and virgin subjects without HPV infection. The immunological assays were found to result in high sensitivity, for example, in detecting E6, E7 and L1 antibodies. Initial titration curves were performed and ELISA assays conditions were optimized.

Figure 7:
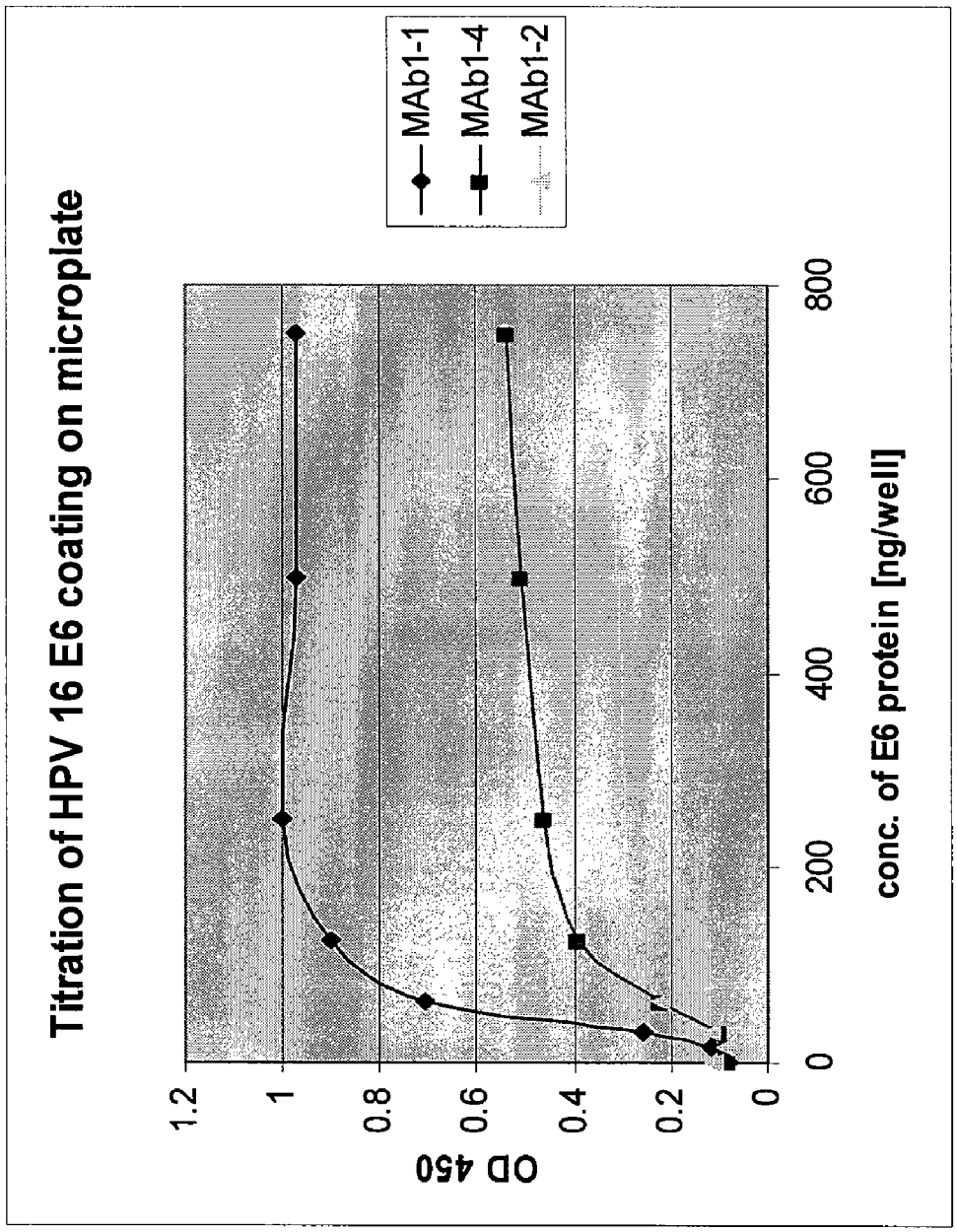
FIG. 7 is a graph showing the results of an exemplary immunological ELISA assay for detecting a monoclonal antibody against E6 oncoprotein on microtiter plates using a purified recombinant protein, recombinant HPV-16 E6 protein, coated on the bottom of the microtiter plates.

FIG. 7 is a graph showing the results of an exemplary immunological ELISA assay for detecting various monoclonal antibodies against E6 protein on microtiter plates using a purified recombinant protein, recombinant HPV-16 E6 protein, coated on the bottom of the microtiter plates. The concentrations of the recombinant HPV-16 E6 proteins used to coat the bottom of the microtiter plates were about 750 ng, 500 ng, 250 ng, 125 ng, 62.5 ng, 31.25 ng per well, respectively, demonstrating the E6 recombinant proteins interact with different monoclonal anti-E6 antibodies with different binding affinities. The results indicate that the purified E6 recombinant protein is capable of specific binding to antibodies against E6 protein, thus suitable for using as a capture agent in an antibody test to detect antibodies from clinical samples of subjects and assay for HPV infection.

As shown in FIG. 7, a dose dependent binding assay for the HPV-16 E6 recombinant protein showed a highest affinity with one antibody, MAb1-1, among the three antibodies tested. The variation in binding affinity could come from different source of immunogens that the three antibodies are originally raised against to. (The purified recombinant proteins as obtained are contemplated to be better immunogens than peptides or other purified HPV proteins). The variation in binding affinity may also indicate that different clinical samples or different subjects of HPV infection may give rise to different immune responses, thus may react differently with the purified recombinant proteins as described herein. Since the E6 recombinant protein binds two out of three antibodies in FIG. 7, the E6 recombinant protein described herein should contain at least two or more active epitopes on the surface of its conformational form for such binding to be detected. The results in FIG. 7 indicate the purified E6 recombinant protein can be used to capture target antibodies from HPV infected subjects.

Figure 8:
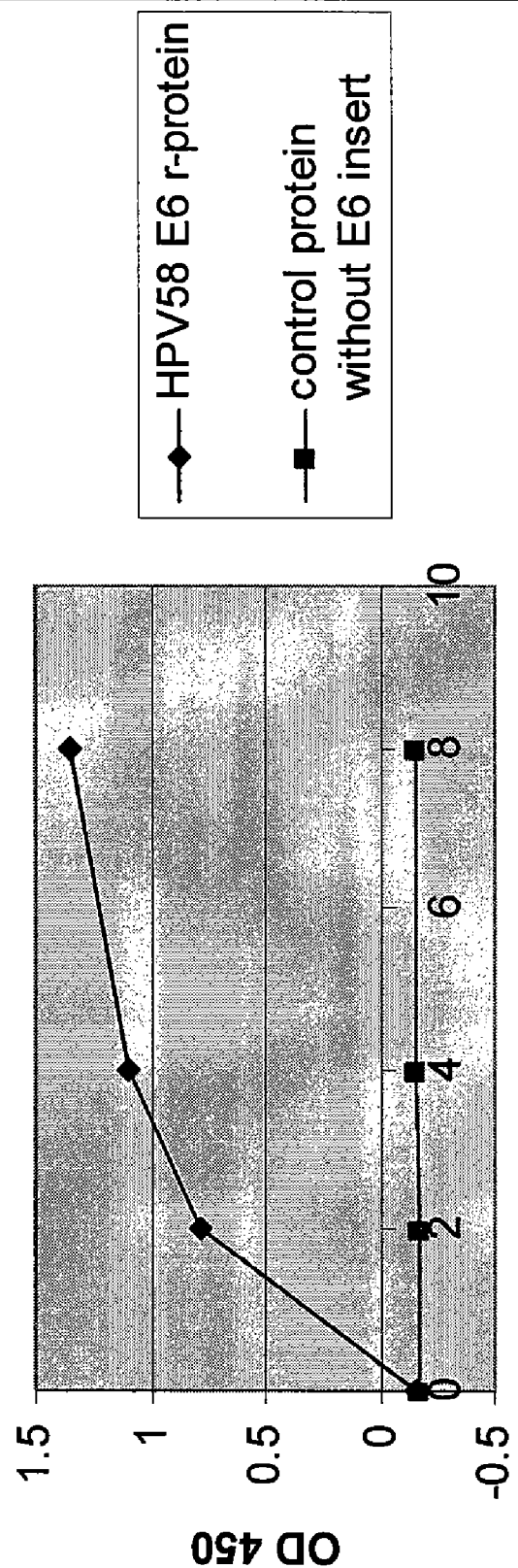
FIG. 8 is a graph showing the results of an ELISA assay for detecting a monoclonal antibody against E6 oncoprotein on microtiter plates using another exemplary purified recombinant protein, a recombinant HPV-58 E6 protein, coated on the bottom of the microtiter plates.

FIG. 8 is a graph showing the results of an ELISA assay for detecting a monoclonal antibody against E6 oncoprotein on microtiter plates using another exemplary purified recombinant protein, a recombinant HPV-58 E6 protein, coated on the bottom of the microtiter plates. The concentrations of the purified recombinant HPV-58 E6 proteins used to coat the bottom of the microtiter plates were about 8 μg/ml, 4 μg/ml, 2 μg/ml per well, respectively, demonstrating specific binding of the E6 recombinant proteins to a monoclonal anti-E6 antibody, MAb1-1, as compared to MBP control protein which showed no binding. The linearity of the titration curve indicates assay sensitivity may be from micrograms to nanograms range, or even picograms or lower range. The results in FIG. 8 confirm that the purified recombinant HPV-58 E6 proteins is active in binding to anti-E6 antibodies, thus suitable for using as a capture agent to detect antibodies from samples from HPV infected subjects.

Figure 9:
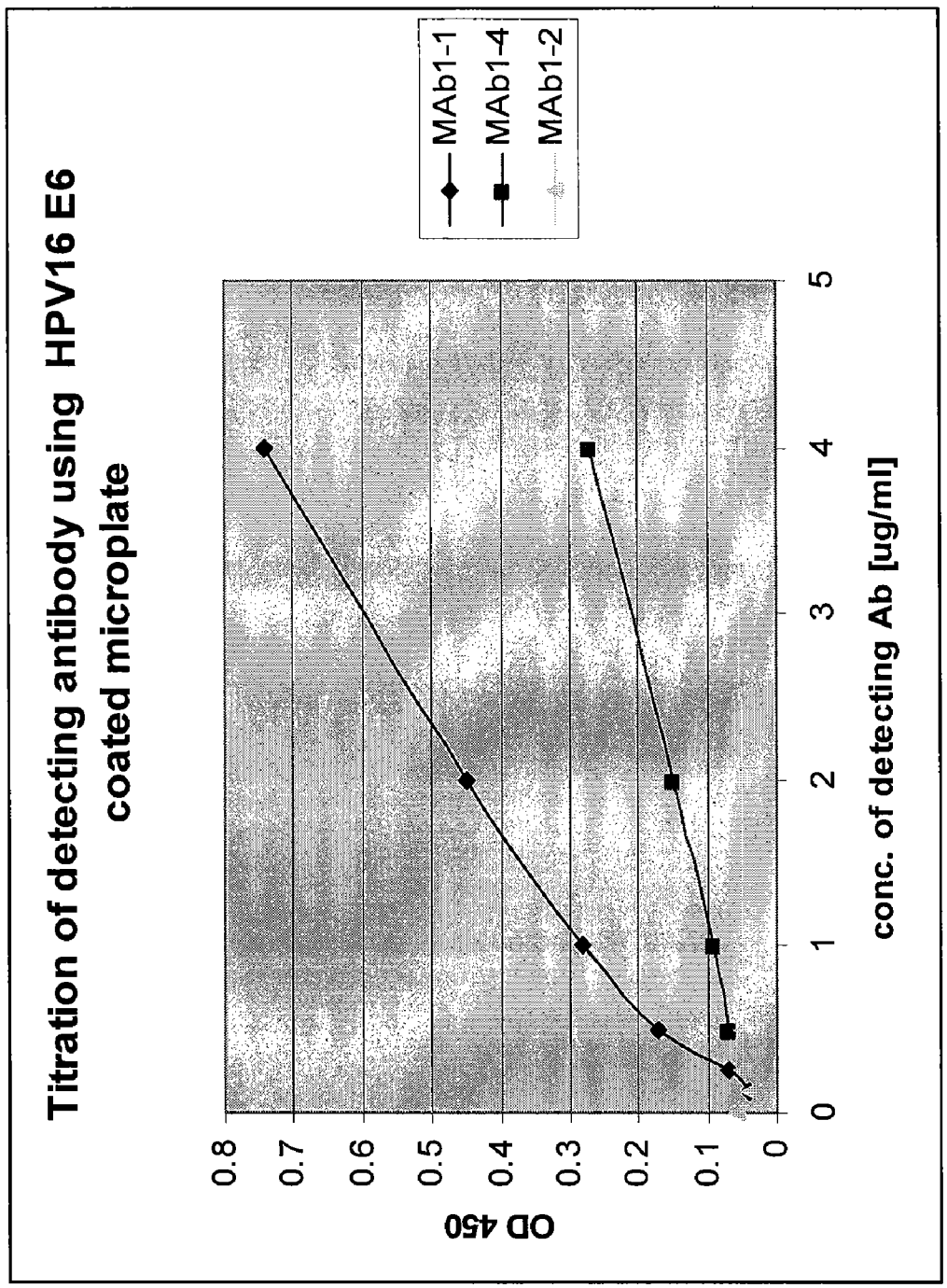
FIG. 9 is an exemplary graph showing the results of an ELISA assay for detecting various monoclonal antibodies (MAb1-1, MAb1-2, and MAb1-4) against E6 oncoprotein on microtiter plates using purified recombinant proteins, recombinant HPV-16 E6 proteins, coated on the bottom of the microtiter plates.

FIG. 9 is an exemplary graph showing the results of an ELISA assay for detecting various monoclonal antibodies (MAb1-1, MAb1-2, and MAb1-4) against E6 oncoprotein on microtiter plates using purified recombinant proteins, recombinant HPV-16 E6 proteins, coated on the bottom of the microtiter plates. The concentrations of the recombinant HPV-16 E6 proteins used to coat the bottom of the microtiter plates were about 8 μg/ml, 4 μg/ml, 2 μg/ml, 1 μg/ml, and 0.5 μg/ml per well, respectively, demonstrating the E6 recombinant proteins interact with different monoclonal anti-E6 antibodies with different binding affinities. The results in FIG. 9 indicate that the purified E6 recombinant protein is capable of specific binding to antibodies against E6 protein, thus suitable for using as a capture agent in an antibody test to detect antibodies from clinical samples of subjects and assay for HPV infection. The linearity of the titration curves indicates assay sensitivity may be micrograms to nanograms range, or even picograms or lower level.

Figure 10:
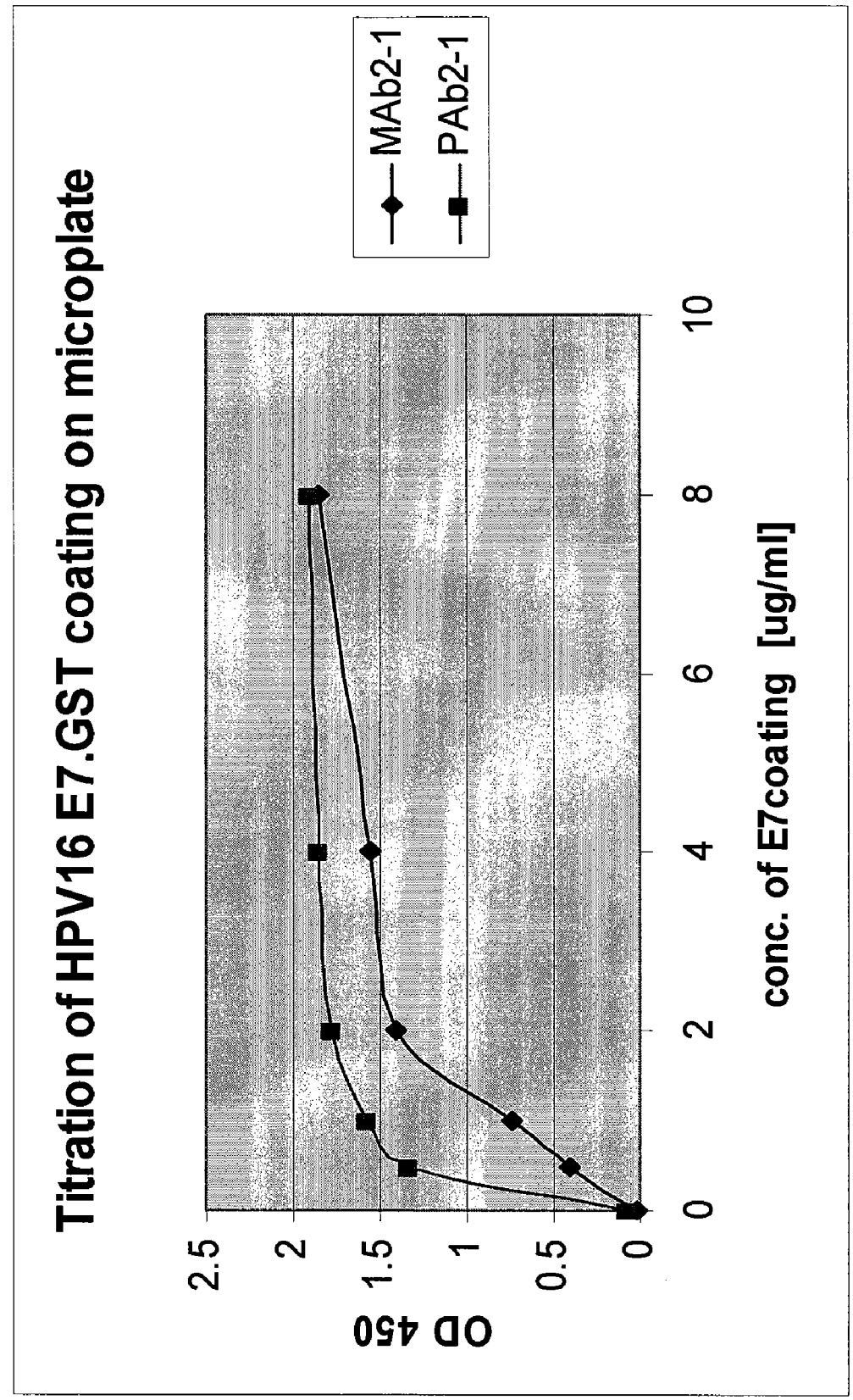
FIG. 10 is another exemplary graph showing the results of an immunological ELISA assay for detecting a monoclonal antibody (MAb2-1) and a polyclonal antibody (PAb2-1) against E7 oncoprotein on microtiter plates using purified recombinant proteins, recombinant HPV-16-E7 fusion proteins, coated on the bottom of the microtiter plates.

FIG. 10 is another exemplary graph showing the results of an immunological ELISA assay for detecting a monoclonal antibody (MAb2-1) and a polyclonal antibody (PAb2-1) against E7 oncoprotein on microtiter plates using purified recombinant proteins, recombinant HPV-16-E7 fusion proteins, coated on the bottom of the microtiter plates. The concentrations of the purified recombinant HPV-16-E7 proteins used to coat the bottom of the microtiter plates were about 8 μg/ml, 4 μg/ml, 2 μg/ml, 1 μg/ml, and 0.5 μg/ml per well, demonstrating the E7 recombinant proteins interact with different monoclonal anti-E7 antibodies with different binding affinities.

Figure 11:
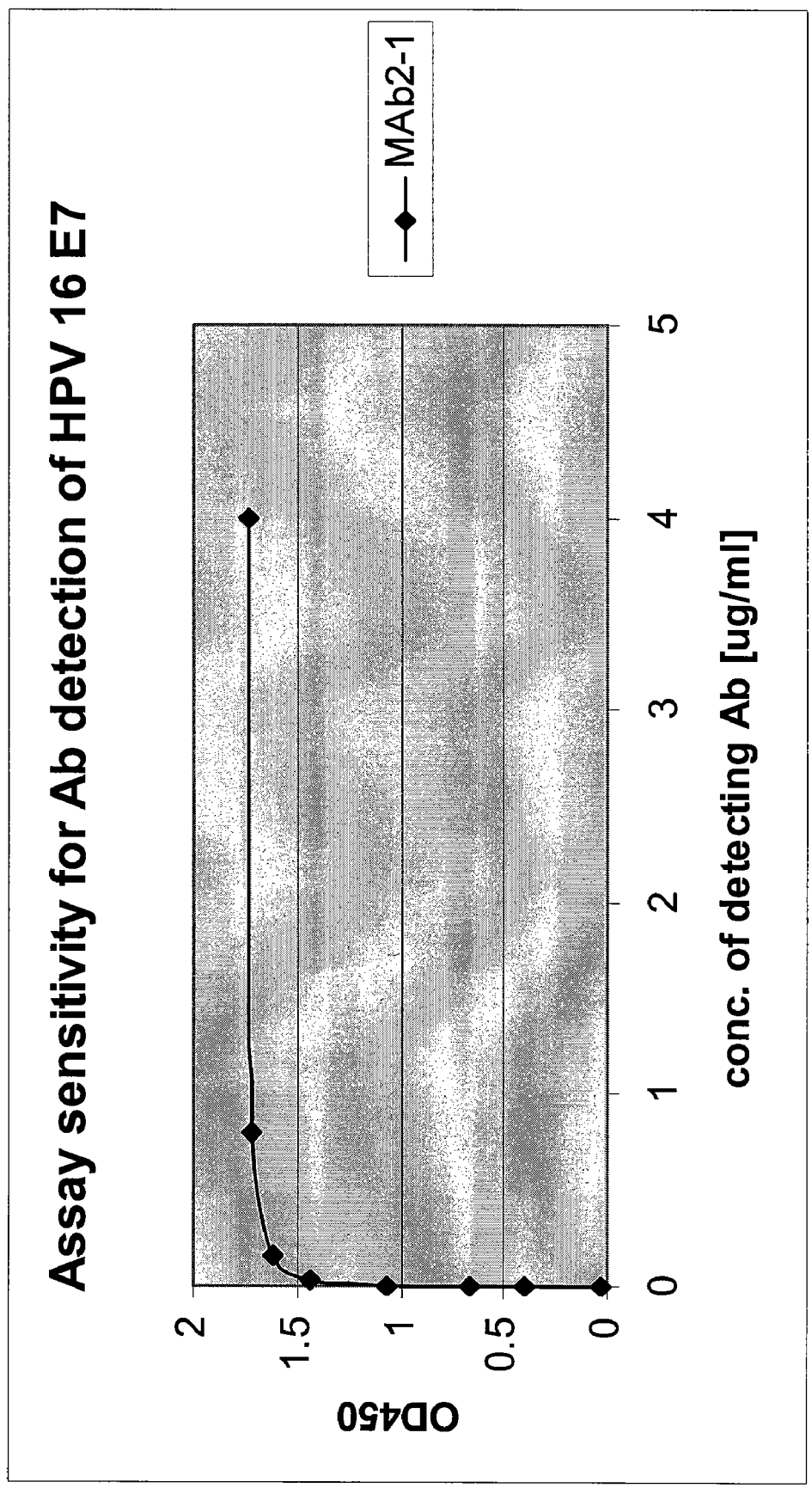
FIG. 11 is another exemplary graph showing the results of an immunological ELISA assay sensitivity for detecting monoclonal antibody (MAb) against E7 oncoprotein using purified recombinant proteins, recombinant HPV-16-E7 fusion proteins, coated on the bottom of the microtiter plates.

FIG. 11 is another exemplary graph showing the results of an immunological ELISA assay for detecting monoclonal antibody (MAb2-1) against E7 oncoprotein using purified recombinant proteins, recombinant HPV-16E7 fusion proteins, coated on the bottom of the microtiter plates. The concentrations of the purified recombinant HPV-16-E7 proteins used to coat the bottom of the microtiter plates were about 4 μg/ml, 1 μg/ml, 0.25 μg/ml, 0.125 μg/ml, 62.5 ng/ml, and 31.25 ng/ml per well, respectively.

TABLE 2

| Subject# | $OD_{450}$ in E6 Ab test | $OD_{450}$ in E7 Ab test |
| --- | --- | --- |
| 12 | 0.41 | 0.30 |
| 1 | 0.40 | 0.37 |
| 20 | 0.94 | 0.60 |
| 3 | 1.40 | 1.34 |
| 57 | 1.38 | 1.12 |
| 40 | 1.56 | 1.47 |
| Mab1-1/Pab2-1 | 0.35 | 0.48 |
| buffer only | 0.10 | 0.09 |

The results in FIGS. 10 and 11 indicate that the purified E7 recombinant protein is capable of specific binding to antibodies against E7 protein, thus suitable for using as a capture agent in an antibody test to detect antibodies from clinical samples of subjects and assay for HPV infection. The linearity of the titration curves indicates assay sensitivity may be micrograms to nanograms range, or even picograms or lower level. Since the purified E7 recombinant proteins bind more than one antibody tested, the E7 recombinant protein described herein should contain at least two, or even more than two active epitopes on the surface of its conformational form for such binding activity to be detected.

Table 2 illustrates the results of various ELISA antibody tests on clinical human subjects on selected samples. The $OD_{450}$ readings for E6 antibody tests and E7 antibody tests are shown.

Example 11

Immunological ELISA Antigen Test for Detection of HPV Associated Antigens or Proteins A pair of antibodies can be used as a capture antibody and a detection antibody in an antigen test. Such as a sandwiched ELISA assay.

Different pairs of antibodies in different combinations of mABs/mABs, polyABs/mABs, mABs/polyABs or polyABs/polyABs were tested as the capture and detection antibodies and the sandwiched ELISA assay conditions were optimized. The capture and detection antibodies are chosen in different monoclonal/polyclonal combination for a secondary antibody to interact and bind to the resulting immunocomplex. If the optimized capture and detection antibodies are both polyclonal antibodies or both monoclonal antibodies, then one of the capture and detection antibodies will be conjugated to be used with immunological assay-derived detection substrates, such as conjugated horse radish peroxidase, and others used in immunological assays. In general, a sandwiched ELISA in an antigen test is performed according to standard procedures.

The purified recombinant proteins were used to raise antiserum, polyclonal and monoclonal antibodies by injecting to animal species and screening with the recombinant proteins for specific binding. Many convenient animals species can be used to prepare the appropriate antisera, and these antisera can be used directly. Suitable animal species include mice, rats, rabbits, guinea pigs, or even larger mammals, such as sheep. For administration to such animals, the recombinant proteins are generally administered in the presence of an adjuvant, usually Freund's complete adjuvant, and the polyclonal sera are harvested periodically by standard techniques.

Monoclonal antibodies may be produced using the method of Kohler and Milstein or by more recent modifications thereof by immortalizing spleen or other antibody-producing cells from injected animals to obtain monoclonal antibody-producing clones. HPV positive and negative human serum samples are useful in screening monoclonal antibody producing hybridoma to ensure the specificity of the monoclonal antibody clones. More than one positive clones reactive with purified E6, E7, and L1 are obtained and further injection of the obtained cell cultures to mice or other animal source can be used to produce ascites for purifying the monoclonal antibodies, such as by protein A affinity column chromatography. The purified antibody will be used as either the capture or detection probes in our ELISA or to be conjugated with detection enzymes, such as (HRP, AP, etc.) for ELISA substrate detection in an absorbent, fluorescent, or chemiluminecence detection system.

The polyclonal and monoclonal antibodies obtained are useful for diagnosis of HPV infection in cervical biopsies, serum or genital swabs specimen and in assessing disease levels in human or other subjects. In particular, diagnosis using the antibodies of the invention permits identification of patients at high risk for malignant transformation as well as identification of the particular phase of CIN associated with the sample. The antibodies can also be used in analysis of serum to detect HPV virus or to detect the virus in metastases of infected tissue, as well as to monitor the progression of HPV immunotherapy, anti-HPV vaccines, or other therapeutic agents directed to control of HPV infection and/or cervical carcinoma.

The 96-well format is a high throughput screening format useful to optimize assay procedures and conditions. Positive controls and negative controls were also performed on, for example, serum samples from donor subjects that are positive for HPV infection and virgin subjects without HPV infection. Initial titration curves were performed and ELISA assays conditions were optimized. The immunological assays were found to result in high sensitivity, for example, in detecting E6, E7 and L1 proteins.

Figure 12:
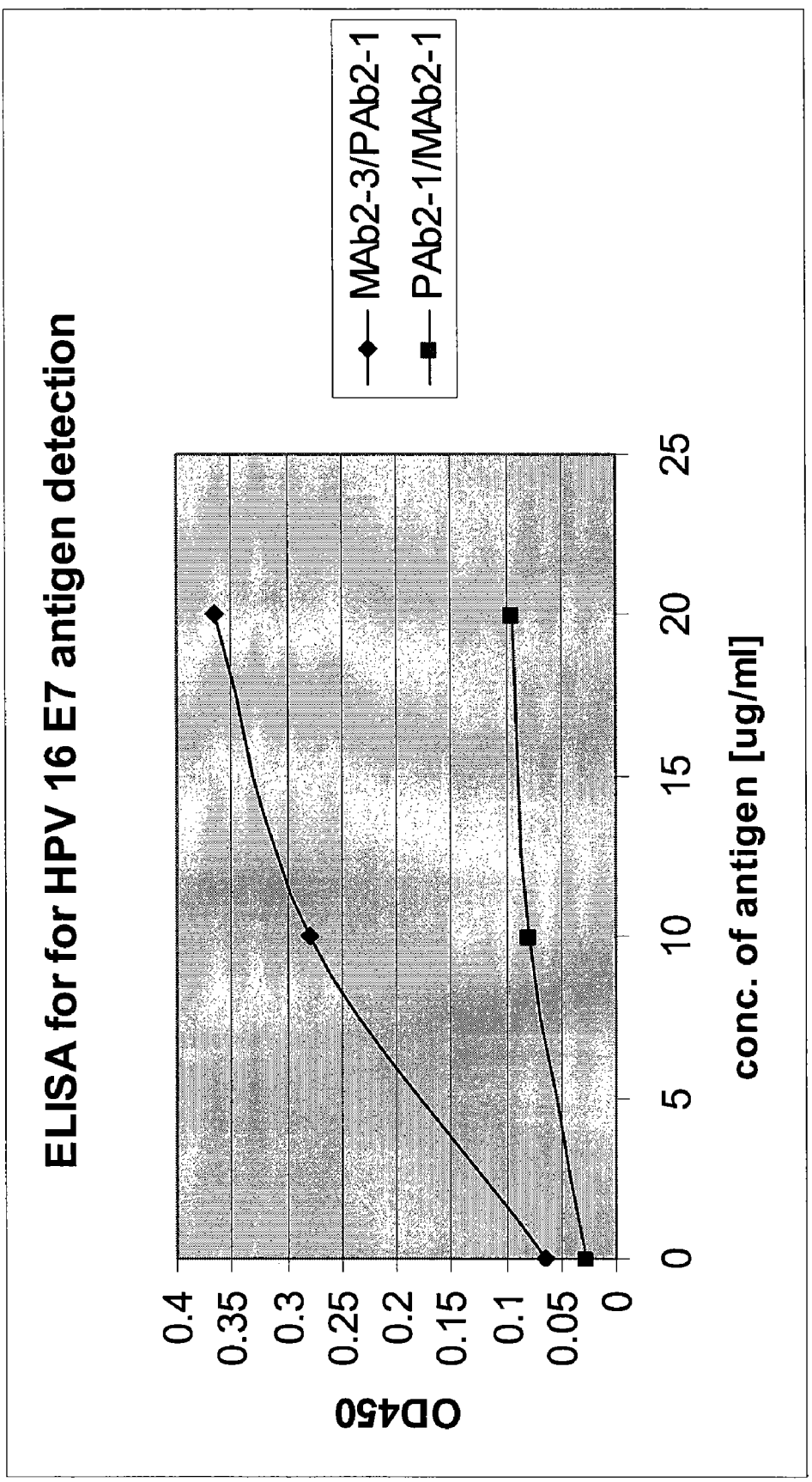
FIG. 12 is a graph showing the results of another exemplary immunological sandwiched ELISA assay for detecting purified recombinant proteins, recombinant HPV-16-E7 fusion proteins, using a combination of two monoclonal-antibodies (MAb2-1, MAb 2-3) and a combination of polyclonal- and monoclonal-antibody (PAb2-1, MAb2-1) against E7 oncoprotein as a pair of capture and detection antibodies for capturing the recombinant proteins and being able to be detected by a detection system.

FIG. 12 is a graph showing the results of an exemplary immunological sandwiched ELISA assay for detecting purified recombinant proteins, recombinant HPV-16-E7 fusion proteins, using a combination of two monoclonal antibodies (MAb2-1, MAb 2-3) and a combination of polyclonal- and monoclonal-antibody (PAb2-1, MAb2-1) against E7 oncoprotein as a pair of capture and detection antibodies.

Anti-E6, anti-E7, and anti-L1 capture antibody were attached to the bottoms of the microtiter plate for coating before the purified recombinant proteins were added. Then a detection antibody is used to detect the captured recombinant protein bound to the capture antibody. Optimized capture and detection antibody concentrations were identified. The concentration of the recombinant proteins in the reaction resulting in linearity in the ELISA assay for antigen detection was determined. These sandwiched ELISA assays were repeated multiple times on the same day, as well as on different days to determine assay reproducibility and reliability. Specificity and sensitivity for each assay were determined. Furthermore, the ELISA assay was shown to have selectivity in detecting cervical cancers versus other cancers, for example, to demonstrate non-cross reactivity with samples from ovarian or endometrial cancers. Since it is known that HPV is found in most if not all cervical cancer cells, but is usually not associated with other cancers, the antigen tests as described herein should not detect antigens associated with other cancers. To test for this selectivity, for example, extracts from tissues of ovarian and endometrial cancer cell lines can be tested and can also serve as negative controls in the antigen tests.

Because most of the samples assayed herein are from genital swabs of a subject, it is possible that the subject may have sexually transmitted disorders and therefore infected with organisms such as *Chlamydia*/Gonorrhea (bacteria) and *Candida* (fungi), non-cross reactivity with antigens from other sexually transmitted organisms or other viruses besides HPV are tested. Human serum samples from HPV infected patients and HPV negative subjects were also tested in the antigen tests. As an example, antigen tests were performed to detect the presence of HPV E6, E7, and L1 proteins in a clinical sample.

Table 3 shows $OD_{450}$ data from ELISA immunoassays, comparing the results of the antigen tests and the antibody tests for different HPV proteins for selected samples.

TABLE 3 results of the ELISA immunoassays and the comparison of antigen tests and antibody tests

| Subject # | $OD_{450}$ in E6 Ab test | | $OD_{450}$ in E7 Ab test | | $OD_{450}$ in E6 Ag test |
|---|---|---|---|---|---|
| | 1:10 | 1:50 | 1:10 | 1:50 | 1:10 |
| 4 | 0.29 | 0.11 | 0.36 | 0.13 | 0.14 |
| 34 | 1.40 | 0.86 | 1.50 | 1.22 | 0.45 |
| 195 | 1.15 | 0.75 | 0.63 | 0.26 | 0.02 |
| 196 | 0.32 | 0.12 | 0.58 | 0.19 | 0.37 |
| 197 | 0.12 | 0.10 | 0.12 | 0.07 | 0.01 |
| 103 | 0.65 | 0.26 | 0.48 | 0.15 | 0.17 |
| 105 | 0.11 | 0.08 | 0.11 | 0.07 | 0.43 |
| 107 | 0.25 | 0.09 | 0.36 | 0.14 | 0.06 |
| 108 | 1.06 | 0.52 | 1.32 | 0.88 | |
| 109 | 0.84 | 0.30 | 1.01 | 0.45 | |
| 119 | 0.11 | 0.06 | 0.10 | 0.09 | |
| MAb1-1/Pab2-1 | 0.34 | | 1.53 | | |
| buffer only | 0.05 | | 0.06 | | |

Example 12

One-Step Rapid Immunological Assay for Detection of HPV Associated Antigens, Proteins, or Antibodies The one-step rapid immunological assay as provided herein is a non-invasive and easy to run assay, similar to the types of over-the-counter pregnancy tests and without the need of any particular test instrument. The one-step rapid immunological assay can be an in vitro immunochromatographic assay for direct, qualitative detection of common HPV antigens, specific antigens for high risk HPV types, or HPV associated antibodies. The one-step rapid Immunological assay can be used as an adjunct test to Pap smear examination, as point-of-care diagnosis, and/or small clinics or labs. The one-step rapid Immunological assay is suitable for testing condition at room temperature to simply add an obtained sample with or without dilution, wait for a reaction time period for the designed reactions to occur, and score the results, for example, visualization of the results.

The one-step rapid immunological assay may be a membrane or stick test striped with a capture agent, e.g., purified HPV antibodies, recombinant proteins, or HPV-associated antibodies and proteins, etc., as described herein to capture a target agent, e.g., HPV-associated antibodies and HPV-associated proteins, etc., in the clinical sample, followed by an immunoassay detection system.

The one-step rapid immunological assay can be performed vertically on a membrane or lateral in a strip. The lateral flow-through or diffusion one-step rapid immunological assays may also be referred to as immunochromatographic strip tests would take about 5-15 minutes to obtain results and is easy to use, requiring limited training and does not require instrumentation. The basic principles of the assay include a solid phase nitrocellulose membrane or strip containing the capture agent to react with a swab sample from a Pap smear. If the patient sample contains the target agent, then the capture agent in the nitrocellulose membrane reacts with the target agent, and a complex is formed and migrates in the nitrocellulose membrane through diffusion or capillary action.

At a set location in the nitrocellulose membrane or strip, colored particles coupled with anti-human (or anti-mouse or anti-rabbit for antigen detection) immunoglobin are disposed. If the samples contain anti-HPV antibody, the color particle coupled with anti-human (or anti-mouse or anti-rabbit for antigen detection) immunoglobin antibody may react with anti-HPV antibody and form a sandwich-type immunocomplex on the solid phase nitrocellulose membrane or strip, resulting in a visible band. If no target agent is present in the samples, there will be no visible band. All tests may or may not include an internal procedural positive and negative control lines used to validate the test results. Appearance of reactive colored lines, therefore, indicates a positive result, while a negative test produces only one or no line. Therefore, the presence of the target agent in samples can be quickly detected. The assay can be very sensitive and the nitrocellulose membranes, strips, or other suitable membranes or strips are generally very stable, for example, may last months if kept dry and away from heat.

The membrane or stick can also be administered to the test human subject during sample collection and/or combined with the cotton swabs, independently or together, to allow the designed immunological reactions to start and thus obtain the test results instantly, fro example, right after insertion of a speculum and the swab into the endocervix of the test human subject. Thus, the one-step rapid immunological assay can serve as a primary screening test. The one-step rapid immunological assay can be performed before additional HPV confirmatory tests, including conventional pap smear cytological tests, the immunological assays and nucleic acid hybridization assays as described herein, or combinations thereof.

Similar procedures and reactions condition as used in the antigen tests and antibody tests as described herein can be employed for the one-step rapid immunological assay. Purified recombinant proteins as provided herein can be used to impregnate a nitrocellulose membrane or strip. To the other end of the strip, colored particles coupled with anti-human immunoglobin antibody can be disposed. Samples can be added and reaction conditions were optimized. Negative controls may include one or positions on the membrane or strip without the purified recombinant proteins or with only BSA, serum proteins, or other negative control proteins. Assay specificity and sensitivity are determined and detection of ng/ml range of the target agent is a good range for commercialization.

Example 13

Protein Chip Immunological Assay for Detection of HPV Associated Antigens Proteins or Antibodies Protein chip immunological assays were developed to detect antibodies using the purified recombinant HPV proteins. In addition, the protein chip immunological assay for detecting HPV-associated proteins, HP-induced antigens, or HPV proteins were performed using purified polyclonal or monoclonal antibodies or antiserum directly or in a sandwiched-type format using a capture antibody and a detection antibody.

For example, protein chips spotted with purified recombinant proteins, such as HPV-16 E6, HPV-16 E7, HPV-16 L1, HPV-18 E6, HPV-18, E7, HPV-18 L1, HPV-58 E6, etc., as well as control proteins, such as BSA were tested. Initially, the conditions were optimized using obtained antibodies, such as mAB 1-1, mAB 1-4, mAB 1-2, mAB 2-1, mAB 2-2, mAB 2-3, polyAB 1-1, poly AB 2-1, etc. and varied concentrations of the purified recombinant proteins spotted on the protein chips to maximize binding. A secondary antibody coupled to, for example, Cys5, can be added to the surface of the protein chips. Assay specificity and sensitivity were obtained. Positive controls and negative controls from cell culture samples or clinical samples are also tested. In addition, commercially available antibody pairs can be used to detect p53 and RB in the tested sample. Accordingly, the protein chip immunological assays provide a simple and easy readout of HPV-related proteins (proteins of the HPV early genes and late genes, L1, E6, and E7, as well as HPY induced p53, RB, p16INK4a and other proteins) to understand consequent altered expressions of cellular regulators induced by HPV infection in the host as a signature of infection by high risk HPV types, which is likely to lead to cervical cancer.

Figure 13:
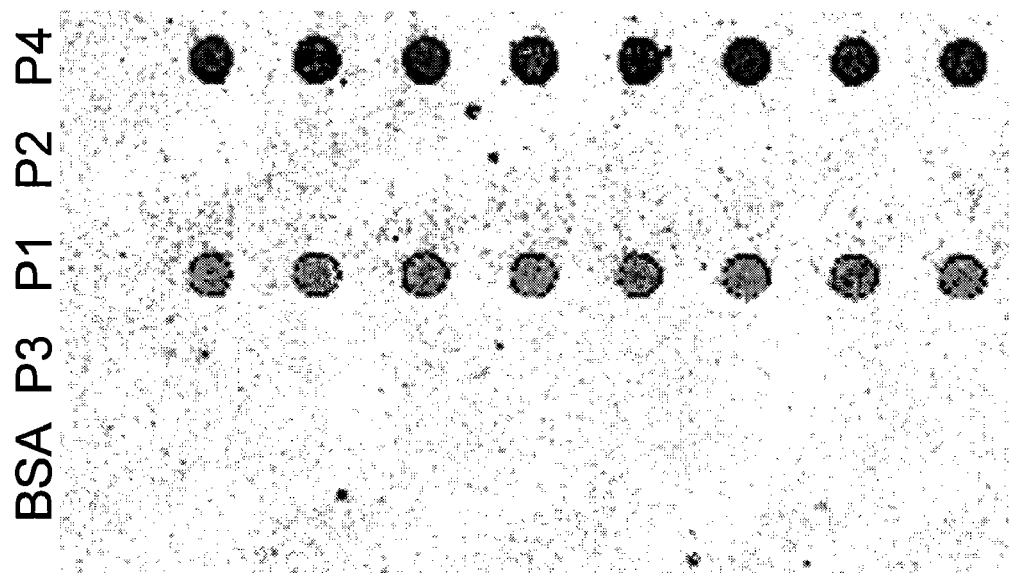
FIG. 13 demonstrates the results of an exemplary immunological protein chip assay for detecting a monoclonal antibody against E6 oncoprotein using purified recombinant proteins coated on a protein chip. P1 indicates recombinant HPV-58 E6-MBP fusion protein. P3 indicates MBP protein as a control. P2 indicates recombinant HPV-16 E7 his tag protein. P4 indicates recombinant HPV-16 E6 his tag protein.

FIG. 13 demonstrates the results of an exemplary immunological protein chip assay for detecting a monoclonal antibody against E6 oncoprotein using purified recombinant proteins coated on a protein chip. As shown in FIG. 13, purified recombinant HPV-16-E6 protein (column P4) and HPV-58-E6 protein (column P1) were spotted onto a glass cover slide at a protein concentration of about 100 µg/ml and a solution of test sample was also spotted for a reaction time of about two hours. As control, purified recombinant HPV-16-E7 protein (column P2), BSA control proteins (column BSA), and recombinant tag-proteins for HPV-58-E6 expression system (column P3) were also attached to the slide. The slide was then reacted with a blocking buffer (PBS/BSA) for 30 min and then reacted with an anti-E6 monoclonal antibody, mAB1-1 (about 5 µgs/ml) for 2 hrs. After the binding reaction, the slide was washed, then dried and reacted with anti-mouse Cy5 (about 4 µgs/ml) for 2 hrs to detect bound mAB1-1. As shown in FIG. 13, the mAB1-1 antibody selectively interacts with the purified recombinant HPV-16-E6 proteins and the purified recombinant HPV-58-E6 (as shown in column P4 and P1, respectively), but not BSA proteins, the purified recombinant HPV-16-E7, nor the recombinant tag-proteins controls (as shown in columns BSA, P3, and P2, respectively). The results indicate that the purified recombinant HPV proteins as provided herein can specifically retain their binding abilities to antibodies in various solid phases and thus feasible to further develop the protein chip technology to detect a desirable target agent bind antibody and is feasible.

V. Comparison of Cytological Analyses with the Results from the Immunological Analyses A large number of clinical samples were obtained for performing immunological assays and/or nucleic acid hybridization assays to screen for HPV infection and the results of the cytological and/or histological assays (such as colposcopy and biopsy) on the obtained clinical samples were also received from hospital collaborators.

Table 4 illustrates the interpretation of Pap Smear scores and related cytological or histological status. Pap scores of one (1) to three (3) are considered as normal and four (4) and above as abnormal. ASCUS: Atypical Squamous Cells of Undetermined Significance; unusual or atypical cells in pap smear, may be inconsequential and significance is underdetermined. AGUS: Atypical Glands of Undetermined Significance. LSIL: Low grade of Squamous Intraepithelial Lesion. HSIL: High grade of Squamous Intraepithelial Lesion. SCC: Squamous Cell Carcinoma. CIN 1: Cervical Intraepithelial Neoplasia, mild cell abnormalities. CIN2: Cervical Intraepithelial Neoplasia with lesions appearing more aggressive. CIN3: Cervical Intraepithelial Neoplasia with aggressive form of dysplasia.

TABLE 4 interpretation of Pap Scores

| Score | Diagnosis status | Status from colposcopy and biopsy |
|---|---|---|
| 4 | ASCUS | |
| 5 | AGUS | |
| 6 | LSIL | CIN 1 |
| | no cytomorphological change of HPV infection | |
| 7 | LSIL | CIN 1 |
| | cytomorphological change due to HPV infection | |
| 8 | HSIL | CIN 2 |
| 9, 10 | high probability of progressing into invasive cancer | CIN 3 |
| 11 | SCC | Invasive carcinoma |
| 12 | Adenocarcinoma | |
| 14 | sampling disqualified for pap smear score too much bleeding due to inflammatory or maybe cancer, less cells, not enough cells to view the morphology | |
| 15 | AGUS, favor neoplasm | |
| 16 | ASCUS, maybe HSIL | |
| 17 | LSIL, not sure about HSIL | |

FIG. 14 illustrates a comparison of the results from E6 antibody test with E7 antibody test. The results from the HPV-16-E6 Ab test correlates well to the results from the HPV-16-E7 Ab test to indicate possible HPV infection. In addition, the results correlate wells with the pap scores. Abnormal pap smear results are also shown as positive in the E6 antibody tests and the E7 antibody tests. Some normal pap smear samples are also shown as positive in the E6 antibody tests and the E7 antibody tests, indicating past HPV infection, current initial or early HPV infection.

FIG. 15 illustrates a comparison of the results from antibody tests with antigen tests. The E6 Ab tests correlates well to the E7 Ab tests and the E6 Ag tests. Subject 107 and subject 195 were not detected as positive in the E6 Ag test and may indicate HPV infection in the past.

Table 5 is a summary of PAP smear results from a total of 896 subjects. Out of 896 tested clinical samples, the samples from 876 subjects were tested to be Pap normal, and the samples from 20 subjects are tested to be PAP abnormal. Thus, about 97.8% in the sample population is tested to be pap normal and about 2.2% in the sample population is tested to be pap abnormal, reflecting a typical rate of pap smear screening in a general population.

TABLE 5 summary of pap smear results for the tested clinical samples

| Pap smear | Subject# | % |
|---|---|---|
| Abnormal | 20 subjects | 2.2% |
| Normal | 876 subjects | 97.8% |
| Total | 896 subjects | 100% |

In addition to antibody tests and antigen tests performed for both HPV proteins encoded by HPV early genes and late genes, PCR nucleic acid hybridization assays were performed. Total of 442 subjects were tested on HPV-16 E6 Ab test/assay, including 282 pap normal, PCR L1 negative subjects and 160 pap normal, PCR L1 positive subjects. The cutoff was determined based on the OD distribution between the groups of PCR positive versus PCR negative. Individual with more than two fold of the $OD_{450}$ value of the average $OD_{450}$ value from the 282 pap normal, PCR L1 negative subjects was set as positive, otherwise are negative as cutoff for the $OD_{450}$ value.

For example, Table 6 shows the results of the samples from the 896 subjects tested for the presence of L1 genes using PCR nucleic acid hybridization assays. Among the 896 obtained sample, 164 samples (18%, 164/896) were tested PCR HPV-L1 positive as an indicator for HPV infection of screening from the general population. Among the 896 obtained, 67 samples (7.5%, 67/896) were tested positive on HPV-16-E6 Ab tests as an indicator for HPV infection of screening from the general population and 58 samples out of the 67 samples (7.5%, 58/67) were confirmed as positive by PCR L1 tests. Among the 896 obtained, 164 samples (18%, 164/896) were tested positive on PCR L1 tests as an indicator for HPV infection of screening from the general population.

TABLE 6 results of the nucleic acid hybridization assays

| | Pap smear | | |
|---|---|---|---|
| | Abnormal | Normal | Total (No. and %) |
| PCR positive | 4 subjects (0.4%) | 160 subjects (17.9%) | 164 subjects (18%) |
| PCR negative | 16 subjects (1.8%) | 716 subjects (79.9%) | 732 subjects (82%) |
| Total | 20 subjects (2.2%) | 876 subjects (97.8%) | 896 subjects (100%) |

Table 7 shows the comparison of antibody tests specific for early and late HPV proteins on 80 selected samples from tested subjects with positive PCR test results.

TABLE 7 the results of antibody tests specific for early and late HPV proteins on 80 selected samples

| Subject # | Pap Smear | PCR test | HPV16 E6 Ab test | HPV L1 Ab test |
|---|---|---|---|---|
| 21 | Normal | positive | negative | positive |
| 22 | Normal | positive | negative | positive |
| 23 | Normal | positive | positive | positive |
| 24 | Normal | positive | positive | positive |
| 25 | Normal | positive | positive | positive |
| 26 | Normal | positive | negative | negative |
| 27 | Normal | positive | negative | positive |
| 28 | Normal | positive | positive | positive |
| 29 | Normal | positive | positive | negative |
| 30 | Normal | positive | negative | positive |
| 31 | Normal | positive | positive | positive |
| 32 | Normal | positive | positive | positive |
| 33 | Normal | positive | negative | negative |
| 34 | Normal | positive | positive | positive |
| 35 | Normal | positive | positive | positive |
| 36 | Normal | positive | positive | positive |
| 37 | Normal | positive | positive | positive |
| 38 | Normal | positive | positive | positive |
| 39 | Normal | positive | negative | negative |
| 40 | Normal | positive | positive | positive |
| 41 | Normal | positive | positive | positive |
| 42 | Normal | positive | positive | positive |
| 43 | Normal | positive | positive | positive |
| 44 | Normal | positive | positive | positive |
| 45 | Normal | positive | positive | positive |
| 46 | Normal | positive | positive | positive |
| 47 | Normal | positive | positive | positive |
| 48 | Normal | positive | positive | positive |
| 49 | Normal | positive | positive | positive |
| 50 | Normal | positive | positive | negative |
| 51 | Normal | positive | negative | negative |
| 52 | Normal | positive | negative | negative |
| 53 | Normal | positive | negative | negative |
| 54 | Normal | positive | positive | positive |
| 55 | Normal | positive | positive | positive |
| 56 | Normal | positive | positive | positive |
| 57 | Normal | positive | positive | positive |
| 58 | Normal | positive | positive | positive |
| 59 | Normal | positive | negative | positive |
| 60 | Normal | positive | negative | positive |
| 61 | Normal | positive | positive | positive |
| 62 | Normal | positive | positive | positive |
| 63 | Normal | positive | negative | positive |
| 64 | Normal | positive | positive | positive |
| 65 | Normal | positive | positive | positive |
| 66 | Normal | positive | negative | positive |
| 67 | Normal | positive | negative | positive |
| 68 | Normal | positive | positive | negative |
| 69 | Normal | positive | negative | positive |
| 70 | Normal | positive | negative | negative |
| 71 | Normal | positive | positive | positive |
| 72 | Normal | positive | positive | positive |

TABLE 7-continued the results of antibody tests specific for early and late HPV proteins on 80 selected samples

| Subject # | Pap Smear | PCR test | HPV16 E6 Ab test | HPV L1 Ab test |
|---|---|---|---|---|
| 73 | Normal | positive | positive | positive |
| 74 | Normal | positive | negative | negative |
| 75 | Normal | positive | positive s | negative |
| 76 | Normal | positive | negative | positive |
| 77 | Normal | positive | negative | negative |
| 78 | Normal | positive | negative | negative |
| 79 | Normal | positive | negative | positive |
| 80 | Normal | positive | positive | positive |
| 81 | Normal | positive | positive | positive |
| 82 | Normal | positive | positive | positive |
| 83 | Normal | positive | positive | positive |
| 84 | Normal | positive | negative | positive |
| 85 | Normal | positive | positive | positive |
| 86 | Normal | positive | positive | positive |
| 87 | Normal | positive | positive | positive |
| 88 | Normal | positive | positive | positive |
| 89 | Normal | positive | positive | positive |
| 90 | Normal | positive | positive | positive |
| 91 | Normal | positive | negative | negative |
| 92 | Normal | positive | negative | positive |
| 93 | Normal | positive | negative | positive |
| 94 | Normal | positive | negative | positive |
| 95 | Normal | positive | positive | positive |
| 96 | Normal | positive | negative | positive |
| 97 | Normal | positive | positive | positive |
| 98 | Normal | positive | positive | positive |
| 99 | Normal | positive | negative | positive |
| 100 | Abnormal | positive | positive | positive |

Table 8 shows the results of antibody tests specific early and late HPV proteins on 94 selected samples from tested subjects with negative PCR test results. In general, the positive results from the HPV-16-E6 Ab test correlates well to the results from the HPV-16-L1 Ab test to indicate/confirm possible HPV infection.

TABLE 8 the results of antibody tests specific for early and late HPV proteins on 94 selected PCR negative samples

| Subject# | Pap Smear | PCR test | HPV-16-E6 Ab test | HPV-16-L1 Ab test |
|---|---|---|---|---|
| 101 | Normal | negative | positive | positive |
| 102 | Normal | negative | negative | positive |
| 103 | Normal | negative | negative | positive |
| 104 | Normal | negative | negative | negative |
| 105 | Normal | negative | negative | negative |
| 106 | Normal | negative | negative | negative |
| 107 | Normal | negative | negative | negative |
| 108 | Normal | negative | positive | negative |
| 109 | Normal | negative | negative | negative |
| 110 | Normal | negative | negative | negative |
| 111 | Normal | negative | negative | negative |
| 112 | Normal | negative | negative | negative |
| 113 | Normal | negative | positive | negative |
| 114 | Normal | negative | negative | negative |
| 115 | Normal | negative | negative | negative |
| 116 | Normal | negative | negative | negative |
| 117 | Normal | negative | negative | negative |
| 118 | Normal | negative | positive | positive |
| 119 | Normal | negative | negative | negative |
| 120 | Normal | negative | negative | negative |
| 121 | Normal | negative | negative | negative |
| 122 | Normal | negative | negative | positive |
| 123 | Normal | negative | negative | negative |
| 124 | Normal | negative | negative | negative |
| 125 | Normal | negative | negative | negative |
| 126 | Normal | negative | negative | negative |
| 127 | Normal | negative | negative | negative |
| 128 | Normal | negative | negative | positive |
| 129 | Normal | negative | negative | negative |
| 130 | Normal | negative | negative | negative |
| 131 | Normal | negative | negative | positive |
| 132 | Normal | negative | negative | negative |
| 133 | Normal | negative | negative | negative |
| 134 | Normal | negative | negative | negative |
| 135 | Normal | negative | negative | negative |
| 136 | Normal | negative | positive | negative |
| 137 | Normal | negative | positive | positive |
| 138 | Normal | negative | negative | positive |
| 139 | Normal | negative | negative | negative |
| 140 | Normal | negative | negative | negative |
| 141 | Normal | negative | negative | negative |
| 142 | Normal | negative | negative | negative |
| 143 | Normal | negative | negative | negative |
| 144 | Normal | negative | negative | negative |
| 145 | Normal | negative | negative | positive |
| 146 | Normal | negative | negative | negative |
| 147 | Normal | negative | negative | negative |
| 148 | Normal | negative | negative | negative |
| 149 | Normal | negative | negative | negative |
| 150 | Normal | negative | negative | negative |
| 151 | Normal | negative | negative | negative |
| 152 | Normal | negative | negative | negative |
| 153 | Normal | negative | negative | negative |
| 154 | Normal | negative | negative | negative |
| 155 | Normal | negative | negative | negative |
| 156 | Normal | negative | negative | negative |
| 157 | Normal | negative | positive | positive |
| 158 | Normal | negative | negative | negative |
| 159 | Normal | negative | negative | positive |
| 160 | Normal | negative | negative | negative |
| 161 | Normal | negative | negative | negative |
| 162 | Normal | negative | negative | positive |
| 163 | Normal | negative | negative | negative |
| 164 | Normal | negative | positive | positive |
| 165 | Normal | negative | negative | positive |
| 166 | Normal | negative | positive | positive |
| 167 | Normal | negative | negative | negative |
| 168 | Normal | negative | negative | negative |
| 169 | Normal | negative | negative | negative |
| 170 | Normal | negative | negative | negative |
| 171 | Normal | negative | negative | negative |
| 172 | Normal | negative | negative | negative |
| 173 | Normal | negative | positive | positive |
| 174 | Normal | negative | negative | positive |
| 175 | Normal | negative | negative | negative |
| 176 | Normal | negative | negative | negative |
| 177 | Normal | negative | negative | negative |
| 178 | Normal | negative | negative | negative |
| 179 | Normal | negative | negative | negative |
| 180 | Normal | negative | negative | negative |
| 181 | Normal | negative | negative | positive |
| 182 | Normal | negative | negative | negative |
| 183 | Normal | negative | negative | negative |
| 184 | Normal | negative | negative | negative |
| 185 | Normal | negative | negative | negative |
| 186 | Normal | negative | positive | negative |
| 187 | Normal | negative | negative | negative |
| 188 | Normal | negative | negative | negative |
| 189 | Normal | negative | negative | positive |
| 190 | Normal | negative | positive | negative |
| 191 | Normal | negative | positive | negative |
| 192 | Normal | negative | positive | negative |
| 193 | Normal | negative | negative | negative |
| 194 | Normal | negative | positive | negative |

Table 9 shows the results of antibody (Ab) tests for selective 160 samples of Pap smear Normal and PCR positive subjects further tested to detect the presence of anti-E6 antibodies in the samples.

TABLE 9 the results of antibody tests specific for E6 HPV proteins on 160 selected samples

| E6 Ab tests | Pap smear Normal and PCR Positive (Total of 160 subjects) | |
| --- | --- | --- |
| positive | 55 subjects | 34.3% |
| negative | 105 subjects | 65.7% |
| Total | 160 subjects | 100% |

Table 10 shows the results of both antigen (Ag) tests and antibody (Ab) tests further tested on selected 160 samples of Pap smear Normal and PCR positive subjects further tested to detect the presence of viral E6 antigens and antibodies in the samples. Strong correlation and between-assay agreement are observed for E6 antigen tests and E6 antibody tests.

TABLE 10 the results of antibody tests and antigen tests specific for E6 early HPV antibodies and proteins on 164 selected samples

| | Pap smear Normal and PCR Positive (Total of 160 subjects) | | |
| --- | --- | --- | --- |
| | E6Ab positive | E6Ab negative | total |
| E6Ag positive | 29 subjects (18.1%) | 30 subjects (18.9%) | 59 subjects (37.8%) |
| E6Ag negative | 26 subjects (16.2%) | 75 subjects (46.3%) | 101 subjects (62.2%) |
| total | 55 subjects (34.3%) | 105 subjects (65.2%) | 160 subjects (100%) |

Table 11 shows the results of antibody (Ab) tests from the 164 PCR positive subjects out of the total collected 896 subjects further tested to detect the presence of viral E6 antibodies in these samples.

TABLE 11 the results of antibody tests specific for early E6 HPV proteins on 164 selected samples

| E6 Ab test | PCR Positive (Total of 164 subjects) | |
| --- | --- | --- |
| positive | 57 subjects | 34.8% |
| negative | 107 subjects | 65.2% |
| Total | 164 subjects | 100.0% |

Table 12 shows the results both antigen (Ag) tests and antibody (Ab) tests tested on the 164 PCR positive subjects out of the total collected 896 subjects further tested to detect the presence of viral E6 antigens and antibodies in the samples.

TABLE 12 the results of antibody tests and antigen tests specific for E6 early HPV proteins on 160 selected samples

| | PCR Positive (Total of 164 subjects) | | |
| --- | --- | --- | --- |
| | E6 Ab test positive | E6 Ab test negative | total |
| E6 Ag test positive | 31 subjects (18.9%) | 31 subjects (18.9%) | 62 subjects (37.8%) |
| E6 Ag test negative | 26 subjects (15.9%) | 76 subjects (46.3%) | 102 subjects (62.2%) |
| total | 57 subjects (34.8%) | 107 subjects (65.2%) | 164 subjects (100%) |

Table 13 shows the results of antibody (Ab) tests from 80 selected samples which were tested as PCR positive subjects to further detect the presence of antibodies specific for HPV early proteins and late proteins in these samples. These selected 80 samples are tested on antibody tests for both E6 and L1. Strong correlation and between-assay agreement are observed for E6 antibody tests and L1 antibody tests. Therefore, one of the two assays can be used as a confirmatory check for the other assay and vice versa. For example, out of the 80 samples, 47 subjects (58.8%) are double positive for both assays and 11 subjects (13.8%) are double negative. Among the 80 samples, 69 subjects (86.2%) are positive from either L1 or E6 test. Out of the 80 samples, 47 samples are positive on both E6 and L1 Ab tests, demonstrating very well correlated assay results and confirmed cases of HPV infection. In addition, 27 out of the 47 E6 positive L1 positive samples also were tested to be E6 antigen positive. In general, L1 Ab test is able to detect 92% (47 out of 51) of E6 Ab positive samples (51 samples) and E6 Ab test is able to detect 72% (47 out of 65) of L1 Ab positive samples (65 samples).

TABLE 13 the results of antibody tests specific for early and late HPV proteins on 80 selected samples

| | PCR Positive (Total of 80 subjects) | | |
| --- | --- | --- | --- |
| | E6 Ab test positive | E6 Ab test negative | total |
| L1 Ab test positive | 47 subjects (58.8%) | 18 subjects (22.5%) | 65 subjects (81.2%) |
| L1 Ab test negative | 4 subjects (5%) | 11 subjects (13.8%) | 15 subjects (18.8%) |
| total | 51 subjects (63.8%) | 29 subjects (36.3%) | 80 subjects (100%) |

Table 14 shows the results of both E6 antigen (Ag) tests and E6 antibody (Ab) tests further tested on these selected 80 samples to detect the presence of both E6 antigens and antibodies in these samples.

TABLE 14 the results of antibody tests and antigen tests specific for early E6 HPV proteins on 80 selected samples

| | PCR Positive (Total of 80 subjects) | | |
| --- | --- | --- | --- |
| | E6 Ab test positive | E6 Ab test negative | total |
| E6 Ag test positive | 29 subjects (36.3%) | 14 subjects (17.5%) | 43 subjects (53.8%) |

TABLE 14-continued the results of antibody tests and antigen tests specific for
early E6 HPV proteins on 80 selected samples PCR Positive (Total of 80 subjects)

|  | E6 Ab test positive | E6 Ab test negative | total |
|---|---|---|---|
| E6 Ag test negative | 22 subjects (27.5%) | 15 subjects (18.8%) | 37 subjects (46.3%) |
| total | 51 subjects (63.8%) | 29 subjects (36.3%) | 80 subjects (100%) |

In addition, selected PCR negative samples were also tested on antibody tests and antigens tests for E6, E7, and/or L1. Table 15 shows the results of antibody (Ab) tests on 282 samples which were also tested as PCR negative and Pap normal. The majority of the 282 samples (about 85%) are also negative on E6 Ab tests.

TABLE 15 the results of antibody tests specific for early and late HPV
proteins on 282 selected samples

|  | Pap smear Normal and PCR Negative (only 282 subjects out of 716 subjects analyzed) | |
|---|---|---|
| E6 Ab test positive | 43 subjects | 15% |
| E6 Ab test negative | 239 subjects | 85% |
| Total | 282 subjects | 100% |

Table 16 shows the results of antibody (Ab) tests for both viral early and late proteins on selected 94 samples out of these 282 PCR negative and Pap normal to further detect the presence of both E6 and L1 antibodies in these samples. Out of these PCR negative and Pap normal samples, the majority of the samples were negative on both E6 Ab test and/or L1 Ab test. Only a low percentage of 7 samples (7.4%) are both positive on E6 Ab test and/or L1 Ab test. In addition, among these Pap normal, PCR negative samples, only 28 samples (7+9+12=28/94; 29.8%) are positive to either E6 Ab test and/or L1 Ab test. For the total obtained 896 clinical samples, randomly selected samples were tested on antibody tests for interaction/binding to antibodies specific for HPV early E6 proteins and HPV late L1 proteins as well as PCR nucleic acid hybridization assays.

Table 17 shows the results for antibody tests for E6 and L1 and PCR test on selected 173 (79+94) samples with normal pap smear scores. FIG. 16 illustrates the results from E6 Ab tests, L1 Ab tests, and PCR tests performed on selected 173 subjects with normal pap smear scores. Out of these 173 pap normal samples, 46 samples (26.6%) are positive on all three tests and 53 samples (30.6%) are positive on both E6 Ab test and L1 Ab test, demonstrating that high level of correlation and assay specificity and sensitivity and indicating or even confirming HPV infection, and thus high risk for cervical cancer development in the future if the HPV infection is not treated, even though pap smear were tested negative (normal).

TABLE 16 the results of antibody tests specific for early and late HPV
proteins on 94 selected samples Pap smear Normal and PCR Negative
(Total of 94 subjects)

|  | E6 Ab test positive | E6 Ab test negative | total |
|---|---|---|---|
| L1 Ab test positive | 7 subjects (7.4%) | 13 subjects (13.8%) | 20 subjects (21.2%) |
| L1 Ab test negative | 8 subjects (8.5%) | 66 subjects (70.3%) | 74 subjects (78.8%) |
| total | 15 subjects (15.9%) | 79 subjects (84.1%) | 94 subjects (100%) |

TABLE 17 the results of antibody tests specific for early and late HPV
proteins on 173 (79 + 94) selected samples

| HPV-16-L1 Ab test | PCR L1 positive (selected 79 subject) HPV-16-E6 Ab test | | PCR L1 negative (selected 94 subjects) HPV-16-E6 Ab test | |
|---|---|---|---|---|
|  | positive | negative | positive | negative |
| positive | 46 | 18 | 7 | 13 |
| negative | 4 | 11 | 8 | 66 |
| total | 50 | 29 | 15 | 79 |

Out of these 173 pap normal samples, 79 samples (45.7%) are negative on all three tests and 108 samples (62.4%) are negative on both E6 Ab test and L1 Ab test, demonstrating that high level of correlation of these developed assays and assay specificity and sensitivity. The results further confirm negative HPV infection, and thus low risk for cervical cancer development in the future, consistent with the negative (normal) pap smear results.

Table 18 shows some possible interpretation for comparing the results of antibody tests specific for early and late HPV proteins.

TABLE 18

Assay results and possible interpretations

| HPV immunoassays | interpretation |
|---|---|
| E6 Ab positive, L1 Ab positive | HPV infection, HPV16 related, or at high risk of progression |
| E6 Ab positive, L1 Ab negative | HPV infection, HPV16 related, maybe at risk of early stage of progression |
| E6 Ab negative, L1 Ab positive | HPV past infection, HPV16 related, may not be at risk of progression |
| E6 Ab negative, L1 Ab negative | No HPV infection |

Of the 896 obtained clinical samples, 20 pap abnormal samples were further tested on antibody tests and antigen tests and PCR tests. Table 19 illustrates the results of PCR analyses and E6 Ab test on these 20 pap abnormal subjects.

TABLE 19 the results of PCR analyses 20 Pap abnormal samples

| | Pap smear Abnormal | | |
|---|---|---|---|
| | PCR Positive | PCR Negative | Total |
| E6 Ab positive | 3 subjects (15%) | 9 subjects (45%) | 12 subjects (60%) |
| E6 Ab negative | 1 subjects (5%) | 7 subjects (35%) | 8 subjects (40%) |
| Total | 4 subjects (20%) | 16 subjects (80%) | 20 subjects (100%) |

FIG. 17 illustrates the results of the E6 Ab tests, E6 Ag tests, E7 Ab tests, and PCR L1 tests for these 20 subjects with abnormal pap smear scores. Blank indicates test results not yet available. The positive results from the E6 antibody tests correlate well with the positive results of the E6 antigen tests. All five samples tested so far on E7 Ab tests were positive and also positive on E6 Ab tests.

Overall assay agreement between the E6 Ab test and the L1 Ab test among PCR positive samples (80/164) is 72.5% (58/85). Positive and negative agreements are 92% (47/51) and 38% (11/29), respectively, with positive predictive value (PPV) of about 72.3% (47/65) and negative predictive value (NPV) of about 73.3% (11/15).

Overall assay agreement between the E6 Ab test and the L1 Ab test among PCR negative samples (94/282) is 78% (73/94). Positive and negative agreements are 47% (7/15) and 84% (66/79), respectively, with PPV of about 35% (7/20) and NPV of about 89% (66/74).

Overall assay agreement between the E6 Ab test and PCR L1 test among pap normal samples (442/876) is 66.5% (294/442). Positive and negative agreement are 34% (55/160) and 85% (239/282), respectively, with PPV of about 56% and NPV of about 70%.

Kits can be developed for performing the methods and assays provided herein. Recombinant proteins, antiserum, and antibodies are also provided for developing these assay kits and screening for infection with HPV-16, 18, 31, 33, 35, 45, 52, 58, 59, 66, 68b, 69, 70, 73, 82, etc., types. The kits, the immunological assays, the recombinant proteins, antiserum, and antibodies, etc., as provided herein are useful for a variety of diagnostic analyses, for example, for diagnosing infection by non-oncogenic or oncogenic HPV types or HPV strains in an individual; for determining the likelihood of having cervical cancer, for determining a patient's response to treatment for HPV, for determining the severity of HPV infection in an individual, and for monitoring the progression of HPV in an individual, among others. The kits, the immunological assays, the recombinant proteins, antiserum, and antibodies, etc., as provided herein are useful in the diagnosis of infection with an oncogenic HPV type or a strain of HPV associated with cancers, including cervical, ovarian, breast, anus, penis, prostate, larynx and the buccal cavity, tonsils, nasal passage, skin, bladder, head and neck squamous-cell, occasional peri-ungal carcinomas, as well as benign anogenital warts. The kits, the immunological assays, the recombinant proteins, antiserum, and antibodies, etc., as provided herein are useful in the diagnosis of infection with an oncogenic or a non-oncogenic type or strain of HPV associated with Netherton's syndrome, epidermolysis verruciformis, endometriosis, and other disorders The kits, the immunological assays, the recombinant proteins, antiserum, and antibodies, etc., as provided herein are useful in the diagnosis of infection with an oncogenic or a non-oncogenic HPV type or HPV strain in adult women, adult men, fetuses, infants, children, and immunocompromised individuals.

The kits as described herein can further include, if desired, one or more of various conventional components, such as, for example, containers with one or more buffers, detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized. Exemplary embodiments of the diagnostic methods of the invention are described above in detail.

In a subject kit, the HPV E6, E7, and/or L1 detection reaction may be performed using an aqueous or solid substrate, where the kit may include reagents for use with several separation and detection platforms such as test strips, sandwich assays, etc. In many embodiments of the test strip kit, the test strip has bound thereto recombinant protein or antibody specific for HPV proteins, and captures HPV induced or HPV associated proteins or antibodies on the solid support. The kit usually includes one or more primary or secondary antibodies for detection, which is either directly or indirectly detectable. The kit may also include components for conducting western blots (e.g., pre-made gels, membranes, transfer systems, etc.); components for carrying out ELISAs (e.g., 96-well plates); components for carrying out immunoprecipitation (e.g. protein A); columns, especially spin columns, for affinity or size separation of proteins or antibodies from a sample. The kit may also contain control samples containing oncogenic or non-oncogenic E6 and/or E7, and/or a dilution series of oncogenic E6 and/or E7, where the dilution series represents a range of appropriate standards with which a user of the kit can compare their results and estimate the level of oncogenic E6 and/or E7 in their sample. Such a dilution series may provide an estimation of the progression of any cancer in a patient. Fluorescence, color, or autoradiogram development results may also be compared to standard curves of fluorescence, color or film density provided by the kit.

Assay conditions suitable for binding are those conditions (in terms of salt concentration, pH, detergent, protein concentration, temperature, etc.) which allow for binding to occur, for example, between a capture agent and a target agent, between a primary antibody and a secondary antibody, between a recombinant protein and a protein or antibody that can bind to the recombinant protein, etc., in solid support or in solution. Such conditions, particularly with respect to antibodies and their antigens, are well known in the art (see, e.g., Harlow and Lane (Antibodies: A Laboratory Manual Cold Spring Harbor Laboratory, Cold Spring Harbor, N.Y. (1989)). Conditions suitable for specific binding typically permit binding partners or pairs that have a dissociation constant ($K_D$) of less than about $10^{-6}$ M to bind to each other selectively.

While the foregoing is directed to embodiments of the present invention, other and further embodiments of the invention may be devised without departing from the basic scope thereof, and the scope thereof is determined by the claims that follow.

The invention claimed is:

1. A method of making a composition comprising a recombinant HPV protein selected from the group consisting of a papillomavirus E6 gene product, a papillomavirus E7 gene product, a papillomavirus L1 gene product, and a papillomavirus L2 gene product, comprising the steps of:
   providing a recombinant construct encoding a fusion protein comprising said papillomavirus gene product and an affinity tag selected from the group consisting of a HIS tag, a GST tag, and an MBP tag, wherein said construct does not encode a chaperone;
   expressing said recombinant construct in a host cell;
   incubating an extract prepared from said host cell with an affinity resin under conditions in which said affinity resin specifically binds said affinity tag; and
   eluting said recombinant HPV protein from said affinity resin, wherein said expressing of said recombinant construct in said host cell results in a level of protein expression such that said eluting produces a composition comprising said recombinant HPV protein at a concentration of from 1 mg/L to 10 mg/L, wherein said recombinant HPV protein is present in said composition at a purity of at least 90% as determined by SDS PAGE, and wherein said recombinant HPV protein is present in said composition in a substantially soluble, monomeric form, as determined by size-exclusion chromatography.

2. The method of claim 1, wherein said recombinant HPV protein is present in said composition in a native conformation.

3. The method of claim 1, wherein said recombinant protein is capable of specifically binding to an antibody present in a sample obtained from a mammalian subject infected by a papillomavirus encoding said E6 gene product, said E7 gene product, said L1 gene product, or said L2 gene product.

4. The method of claim 1, wherein said papillomavirus is selected from the group consisting of HPV-6, HPV-11, HPV-16, HPV-18, HPV-31, HPV-33, HPV-35, HPV-39, HPV-42, HPV-43, HPV-44, HPV-45, HPV-51, HPV-52, HPV-53, HPV-54, HPV-55, HPV-56, HPV-58, HPV-59, and HPV-66.

5. A method for assessing risk for developing cervical cancer in a human subject, comprising:
   obtaining a sample from said subject, said sample comprising antibodies produced by said subject;
   contacting said sample with one or more recombinant HPV proteins selected from the group consisting of a papillomavirus E6 gene product, a papillomavirus E7 gene product, a papillomavirus L1 gene product, and a papillomavirus L2 gene product, wherein each of said one or more recombinant HPV proteins is isolated according to the method of claim 1, and wherein each of said one or more recombinant HPV proteins is capable of specific binding to an antibody produced by a human infected with a papillomavirus encoding said E6, E7, L1, or L2 gene product, wherein said contacting takes place under conditions that permit the specific binding of said antibody to said one or more recombinant HPV proteins;
   determining the presence, absence, or amount of one or more antibodies in said sample that specifically binds to said one or more recombinant HPV; and
   assessing the risk for developing cervical cancer in said subject based on the determined presence, absence, or amount of said one or more antibodies in said sample.

6. The method of claim 5, wherein said papillomavirus is selected from the group consisting of HPV-6, HPV-11, HPV-16, HPV-18, HPV-31, HPV-33, HPV-35, HPV-39, HPV-42, HPV-43, HPV-44, HPV-45, HPV-51, HPV-52, HPV-53, HPV-54, HPV-55, HPV-56, HPV-58, HPV-59, and HPV-66.

* * * * *